US012698487B2

(12) United States Patent
Cheng et al.

(10) Patent No.: US 12,698,487 B2
(45) Date of Patent: Aug. 4, 2026

(54) SOLUBLE ENPP1 PROTEINS AND USES THEREOF

(71) Applicants:Inozyme Pharma, Inc., Boston, MA (US); Yale University, New Haven, CT (US)

(72) Inventors: Zhiliang Cheng, Boston, MA (US); Demetrios Braddock, Guilford, CT (US); Paul Stabach, New Haven, CT (US); Steven Jungles, Key West, FL (US)

(73) Assignees: BIOMARIN PHARMACEUTICAL INC., Novato, CA (US); Yale University, New Haven, CT (US)

( * ) Notice: Subject to any disclaimer, the term of this patent is extended or adjusted under 35 U.S.C. 154(b) by 689 days.

(21) Appl. No.: 18/063,263

(22) Filed: Dec. 8, 2022

(65) Prior Publication Data
US 2023/0313158 A1      Oct. 5, 2023

Related U.S. Application Data

(63) Continuation of application No. PCT/US2021/036494, filed on Jun. 8, 2021.

(60) Provisional application No. 63/036,833, filed on Jun. 9, 2020.

(51) Int. Cl.
*C12N 9/16*        (2006.01)
*A61P 43/00*        (2006.01)

(52) U.S. Cl.
CPC ................ *C12N 9/16* (2013.01); *A61P 43/00* (2018.01); *C12Y 301/04001* (2013.01)

(58) Field of Classification Search
None
See application file for complete search history.

(56) References Cited

U.S. PATENT DOCUMENTS

| | | |
|---|---|---|
| 4,751,180 A | 6/1988 | Cousens et al. |
| 4,935,233 A | 6/1990 | Bell et al. |
| 5,418,618 A | 5/1995 | Kagawa et al. |
| 5,428,130 A | 6/1995 | Capon et al. |
| 5,804,413 A | 9/1998 | DeLuca |
| 5,808,656 A | 9/1998 | Goldmann |

(Continued)

FOREIGN PATENT DOCUMENTS

| | | |
|---|---|---|
| DE | 20121960 U1 | 1/2004 |
| EP | 2368999 B1 | 3/2014 |

(Continued)

OTHER PUBLICATIONS

International Preliminary Report on Patentability for International Application No. PCT/US2021/036494, issued Dec. 13, 2022, 18 pages.

(Continued)

*Primary Examiner* — David W Berke-Schlessel
(74) *Attorney, Agent, or Firm* — MARSHALL, GERSTEIN & BORUN LLP

(57) ABSTRACT
In certain aspects, the present invention provides novel soluble ENPP1 or ENPP3 polypeptides, as well as compositions and methods for using those variants to treat an indication associated an ENPP1 or ENPP3 deficiency. The compositions and methods provided herein are useful in treating diseases associated with an ENPP1 or ENPP3 deficiency such as pathological calcification or pathological ossification.

6 Claims, 13 Drawing Sheets

Specification includes a Sequence Listing.

Human Enpp1

(56) References Cited

U.S. PATENT DOCUMENTS

| | | | |
|---|---|---|---|
| 5,837,532 | A | 11/1998 | Preston et al. |
| 5,846,782 | A | 12/1998 | Wickham et al. |
| 5,968,508 | A | 10/1999 | Goldfine et al. |
| 6,001,650 | A | 12/1999 | Colosi |
| 6,043,056 | A | 3/2000 | Yue et al. |
| 6,156,303 | A | 12/2000 | Russell et al. |
| 6,358,923 | B1 | 3/2002 | Yue et al. |
| 6,455,495 | B1 | 9/2002 | Orgel et al. |
| 6,498,617 | B1 | 12/2002 | Shida et al. |
| 6,596,535 | B1 | 7/2003 | Carter |
| 6,730,822 | B1 | 5/2004 | Ivarie et al. |
| 6,825,396 | B2 | 11/2004 | MacArthur |
| 6,875,588 | B2 | 4/2005 | Harvey et al. |
| 7,125,717 | B2 | 10/2006 | Carter |
| 7,294,507 | B2 | 11/2007 | Harvey et al. |
| 7,312,374 | B2 | 12/2007 | Rapp et al. |
| 7,318,919 | B2 | 1/2008 | Gregory et al. |
| 7,323,542 | B2 | 1/2008 | Balian |
| 7,456,683 | B2 | 11/2008 | Takano et al. |
| 7,507,873 | B2 | 3/2009 | Harvey et al. |
| 7,521,591 | B2 | 4/2009 | Ivarie et al. |
| 7,531,167 | B2 | 5/2009 | Glorioso et al. |
| 7,534,929 | B2 | 5/2009 | Ivarie et al. |
| 7,858,297 | B2 | 12/2010 | Girard et al. |
| 7,888,372 | B2 | 2/2011 | Millan et al. |
| 7,902,151 | B2 | 3/2011 | Gorczynski et al. |
| 7,960,529 | B2 | 6/2011 | Crine et al. |
| 8,519,214 | B2 | 8/2013 | Ivarie et al. |
| 8,846,603 | B2 | 9/2014 | Quinn et al. |
| 9,540,621 | B2 | 1/2017 | Quinn et al. |
| 9,642,869 | B2 | 5/2017 | Reddy et al. |
| 9,642,896 | B1 | 5/2017 | Braddock et al. |
| 9,744,219 | B2 | 8/2017 | Braddock et al. |
| 9,867,870 | B2 | 1/2018 | Braddock et al. |
| 9,913,881 | B2 | 3/2018 | Braddock et al. |
| 10,011,847 | B2 | 7/2018 | Aranda et al. |
| 10,052,367 | B2 | 8/2018 | Braddock et al. |
| 10,064,917 | B2 | 9/2018 | Braddock et al. |
| 10,213,483 | B2 | 2/2019 | Otterlei et al. |
| 10,213,484 | B2 | 2/2019 | Braddock et al. |
| 10,357,541 | B2 | 7/2019 | Braddock et al. |
| 10,493,135 | B2 | 12/2019 | Quinn et al. |
| 10,517,927 | B2 | 12/2019 | Braddock et al. |
| 10,583,170 | B2 | 3/2020 | Braddock et al. |
| 10,624,958 | B2 | 4/2020 | Braddock et al. |
| 10,960,050 | B2 | 3/2021 | Braddock et al. |
| 11,266,722 | B2 | 3/2022 | Braddock et al. |
| 2001/0020086 | A1 | 9/2001 | Hubbell et al. |
| 2001/0051065 | A1 | 12/2001 | Togami |
| 2002/0108132 | A1 | 8/2002 | Rapp |
| 2003/0190311 | A1 | 10/2003 | Dall'Acqua et al. |
| 2004/0166521 | A1 | 8/2004 | Boyd et al. |
| 2004/0224893 | A1 | 11/2004 | Wang et al. |
| 2006/0074255 | A1 | 4/2006 | Takayama et al. |
| 2007/0004913 | A1 | 1/2007 | Challita-Eid et al. |
| 2007/0015145 | A1 | 1/2007 | Woolf et al. |
| 2008/0273206 | A1 | 11/2008 | Genge et al. |
| 2009/0180989 | A1 | 7/2009 | Harvey |
| 2009/0253176 | A1 | 10/2009 | Parker et al. |
| 2009/0296167 | A1 | 12/2009 | Motoyama |
| 2009/0298167 | A1 | 12/2009 | Bloom et al. |
| 2010/0184672 | A1 | 7/2010 | McCarty et al. |
| 2010/0203076 | A1 | 8/2010 | Fotin-Mleczek et al. |
| 2010/0240583 | A1 | 9/2010 | Tada et al. |
| 2012/0009592 | A1 | 1/2012 | Froguel et al. |
| 2013/0012574 | A1 | 1/2013 | Monahan et al. |
| 2014/0154774 | A1 | 6/2014 | Quinn et al. |
| 2014/0349369 | A1 | 11/2014 | Buechler et al. |
| 2014/0377859 | A1 | 12/2014 | Quinn et al. |
| 2015/0024460 | A1 | 1/2015 | Quinn et al. |
| 2015/0359858 | A1 | 12/2015 | Braddock et al. |
| 2016/0184458 | A1 | 6/2016 | Heartlein |
| 2017/0096684 | A1 | 4/2017 | Alton et al. |
| 2017/0145393 | A1 | 5/2017 | Quinn et al. |
| 2017/0204386 | A1 | 7/2017 | Vitalis et al. |
| 2017/0290926 | A1 | 10/2017 | Smith et al. |
| 2017/0340713 | A1 | 11/2017 | Braddock et al. |
| 2017/0340714 | A1 | 11/2017 | Braddock et al. |
| 2017/0354719 | A1 | 12/2017 | Braddock et al. |
| 2018/0042738 | A1 | 2/2018 | Sun et al. |
| 2018/0057821 | A1 | 3/2018 | Braddock et al. |
| 2018/0318400 | A1 | 11/2018 | Quinn et al. |
| 2018/0340187 | A1 | 11/2018 | Rodino-Klapac |
| 2018/0371434 | A1 | 12/2018 | Braddock et al. |
| 2019/0022286 | A1 | 1/2019 | Schneiderman |
| 2020/0138905 | A1 | 5/2020 | Braddock et al. |
| 2020/0263153 | A1 | 8/2020 | Khan et al. |
| 2020/0306349 | A1 | 10/2020 | Yan et al. |

FOREIGN PATENT DOCUMENTS

| | | | | |
|---|---|---|---|---|
| EP | 3298140 | A1 | 3/2018 | |
| JP | H04292169 | A | 10/1992 | |
| JP | 2008188015 | A | 8/2008 | |
| JP | 2014-509851 | A | 4/2014 | |
| JP | 2014509617 | A | 4/2014 | |
| JP | 2016530899 | A | 10/2016 | |
| JP | 2018-511346 | A | 4/2018 | |
| JP | 2018-527882 | A | 9/2018 | |
| JP | 6894664 | B2 | 6/2021 | |
| RU | 2272841 | C2 | 3/2006 | |
| RU | 2013142583 | A | 4/2015 | |
| WO | 91/02788 | A1 | 3/1991 | |
| WO | 96/04394 | A1 | 2/1996 | |
| WO | 98/15637 | A1 | 4/1998 | |
| WO | 99/06583 | A1 | 2/1999 | |
| WO | 1999/019495 | A1 | 4/1999 | |
| WO | 2000/032217 | A1 | 6/2000 | |
| WO | 0239994 | A2 | 5/2002 | |
| WO | 2002092020 | A2 | 11/2002 | |
| WO | 03/040340 | A2 | 5/2003 | |
| WO | 2006039480 | A2 | 4/2006 | |
| WO | 2006059113 | A2 | 6/2006 | |
| WO | 2006/135925 | A2 | 12/2006 | |
| WO | 2006135935 | A1 | 12/2006 | |
| WO | 2008/065225 | A2 | 6/2008 | |
| WO | 2008/105911 | A2 | 9/2008 | |
| WO | 2011113027 | A2 | 9/2011 | |
| WO | 2012/125182 | A1 | 9/2012 | |
| WO | 2014126965 | A2 | 8/2014 | |
| WO | 2016100803 | A2 | 6/2016 | |
| WO | 2016187408 | A1 | 11/2016 | |
| WO | 2017/087936 | A1 | 5/2017 | |
| WO | 2017/191274 | A2 | 11/2017 | |
| WO | 2017218786 | A1 | 12/2017 | |
| WO | 2018/027024 | A1 | 2/2018 | |
| WO | 2018/157165 | A1 | 8/2018 | |
| WO | 2019067502 | A1 | 4/2019 | |
| WO | 2019217373 | A1 | 11/2019 | |
| WO | 2020047520 | A1 | 3/2020 | |
| WO | 2020/150716 | A1 | 7/2020 | |
| WO | WO-2020206302 | A1 * | 10/2020 | ............... C12N 9/16 |
| WO | 2021/252549 | A1 | 12/2021 | |
| WO | 2022/076848 | A1 | 4/2022 | |

OTHER PUBLICATIONS

International Search Report and Written Opinion for International Application No. PCT/US2021/036494, mailed Feb. 12, 2021, 28 pages.

Jansen , et al., "ABCC6 prevents ectopic mineralization seen in pseudoxanthoma elasticum by inducing cellular nucleotide release", Proc Natl Acad Sci U S A. 110(50), 2013, 20206-20211.

Jansen , et al., "ABCC6-mediated ATP secretion by the liver is the main source of the mineralization inhibitor Inorganic pyrophosphate in the systemic circulation-brief report", Arterioscler Thromb Vasc Biol. 34(9), 2014, 1985-1989.

Jansen , et al., "Proteolytic maturation and activation of autotaxin (NPP2), a secreted metastasis-enhancing lysophospholipase D", J Cell Sci. 118(Pt 14), 2005, 3081-3089.

(56) References Cited

OTHER PUBLICATIONS

Jansen, et al., "Structure of NPP1, an ectonucleotide pyrophosphatase/phosphodiesterase involved in tissue calcification", Structure. 20(11), 2012, 1948-1959.

Jia, et al., "A novel model of adenine-induced tubulointerstitial nephropathy in mice", BMC Nephrology 2013, 14: 116.

Jiang, et al., "Aberrant Mineralization of Connective Tissues in a Mouse Model of Pseudoxanthoma Elasticum: Systemic and Local Regulatory Factors", Journal of Investigative Dermatology 2007, 127(6): 1392-1402.

Jin-Hua, et al., "Molecular Cloning and Chromosomal Localization of PD-Iβ (PDNP3), a New Member of the Human Phosphodiesterase I Genes," Genomics 45, 1997, 412-415.

Johnson, et al., "Matrix vesicle plasma cell membrane glycoprotein-1 regulates mineralization by murine osteoblastic MC3T3 cells", J Bone Miner Res. 14(6), Jun. 1999, 883-892.

Johnson, et al. "The nucleoside triphosphate pyrophosphohydrolase isozyme PC-1 directly promotes cartilage calcification through chondrocyte apoptosis and increased calcium precipitation by mineralizing vesicles." The Journal of Rheumatology 28.12 (2001): 2681-2691.

Johnson, et al., "Chondrogenesis Mediated by PPi Depletion Promotes Spontaneous Aortic Calcification in NPP1-/-mice" Arteriosclerosis Thrombosis, and Vascular Biology, 25: 686-691 (2005).

Johnson, et al., "Differential mechanisms of inorganic pyrophosphate production by plasma cell membrane glycoprotein-1 and B10 in chondrocytes", Arthritis Rheum. 42(9), 1999, 1986-1997.

Johnson, et al., "Kabat database and its applications: 30 years after the first variability plot," Nucleic Acids Res. 28(1), Jan. 2000, 214-218.

Johnson, et al., "Linked deficiencies in extracellular PP(i) and osteopontin mediate pathologic calcification associated with defective PC-1 and ANK expression", J Bone Miner Res. 18(6), 2003, 994-1004.

Kashioulis et al. 2018; Adenine-diced chronic renal failure in rates: A model of chronic renocardiac syndrome with left ventricular diastolic dysfunction by preserved ejection fraction. Kidney & Blood Pressure Research. 43: 1053-1064.

Kato, et al., "Crystal structure of Enpp1, an extracellular glycoprotein involved in bone mineralization and insulin signaling", Proc Natl Arad Sci U S A. 109(42), Oct. 2012, 16876-16881.

Khan, et al., "Experimental Induction of Calcium Oxalate Nephrolithiasis in Mice", The Journal of Urology 2010, vol. 184, Issue 3, 1189-1196.

Khan, et al., "Ultrastrucural Investigation of Crystal deposits in Npt2a knockout mice: Are they similar to Human Randall's plaques?" J Urol. 2011, 186(3): 1107-1113.

Khan, T. et al., "ENPP1 enzyme replacement therapy improves blood pressure and cardiovascular function in a mouse model of generalized arterial calcification of infancy," Disease Models & Mechanisms, 11(10):dmm035691, 14 pages (2018).

Kober, et al., "Optimized Signal Peptides for the Development of High Expressing CHO Cell Lines", Biotechnology and Bioengineering, 2013, 110(4): 1164-1173.

Lee, et al., "Cloning' chromosomal localization, and tissue expression of autotaxin from human teratocarcinoma ;ells", Biochem Biophys Res Commun. 218(3, 1996, 714-719.

Levy-Litan, et al., "Autosomal-Recessive Hypophosphatemic Rickets Is Associated with an Inactivation Mutation in the ENPP1 Gene", The American Journal of Human Genetics 86, 273-278, 2010.

Li, et al., "Inhibition of Tissue-Nonspecific Alkaline Phosphatase Attenuates Ectopic Mineralization in the Abcc6 -/- Mouse Model of PXE but Not in the Enpp1 Mutant Mouse Models of GACI", J Invest Dermatol. 139(2), Feb. 2019, 360-368.

Li, et al., "Response of Npt2a knockout mice to dietary calcium and phosphorus", PLoS One. 12(4), 2017, e0176232.

Li, et al. "Serum phosphate concentration and incidence of stroke: a systemic review and meta-analysis." Neurological sciences 35.12 (2014): 1877-1882.

Li, et al., "Mutant Enpp1 asj mice as a model for generalized arterial calcification of infancy", Disease Models & Mechanisms 6, 1227-1235 (2013).

Li, Q., et al., "Spontaneous asj-2J mutant mouse as a model for generalized arterial calcification of infancy: a large deletion/insertion mutation in the Enpp1 gene," PLoS ONE, vol. 9, No. 12, Dec. 5, 2014, pp. e113542.

Liang, et al., "Survey of the Enthesopathy of X-Linked Hypophosphatemia and Its Characterization in Hyp Mice", Calcif. Tissue Int. 2009, 85(3): 235-46.

Lieben, et al., "Normocalcemia is maintained in mice under conditions of calcium malabsorption by vitamin D-induced inhibition of bone mineralization", J Clin Invest. 122(5), 2012, 1803-1805.

Lock, et al., "Characterization of a Recombinant Adeno-Associated Virus Type 2 Reference Standard Material", Human Gene Therapy 21: 1273-1285 (2010).

Lomashvili, et al., "Phosphate-induced vascular calcification: role of pyrophosphate and osteopontin," Journal of American Society of Nephrology, 1392-1401, Mar. 4, 2004.

Lust, et al., "A rapid, enzymatic assay for measurement of inorganic pyrophosphate in biological samples", Clinica Chimica Acta 66, 1976, 241-249.

MacKenzie et al. 2012; New insights into NPP1 function: Lessons from clinical and animal studies. Bone. 51:961-968.

MacKenzie, et al., "Altered Bone Development and an Increase in FGF-23 Expression in Enpp1 -/- Mice", PLoS one 2012, 7(2): e32177.

Millán, et al., "Enzyme replacement therapy for murine hypophosphatasia", J Bone Miner Res. 23(6), Jun. 2008, 777-787.

Morrison, et al., "Experimentally Induced Chronic Renal Insufficiency in the Rat", Laboratory Investigation vol. 11, 1962, 321-332.

Murphy, et al., "Synthesis and in vitro hydroxyapatite binding of peptides conjugated to calcium-binding moieties," Biomacromolecules, 8:2237-2243 (2007).

Mus musculus domesticus ecto-nucleotide pyrophosphatase/phosphodiesterase-1 mRNA, complete cds, GenBank J027002, Aug. 12, 2020 searched.

Nagase, et al., Uniprot Submission Accession No. Q9Y6X5 (online at <www.uniprot.org/uniprot/Q9Y6X5.txt?uersion=66>), 2011.

Nakamura, et al., "Association of the human NPPS gene with ossification of the posterior longitudinal ligament of the spine (OPLL)", Human Genetics, 1999, 104(6): 492-497.

Nakanishi, et al. "Development and therapeutic application of transposon-based vectors." Yakugaku Zasshi: Journal of the Pharmaceutical Society of Japan 129.12 (2009): 1433-1443.

Nishioka, et al., "Enhancement of drug delivery to bone: characterization of human tissue-nonspecific alkaline phosphatase tagged with an acidic oligopeptide," Molecular Genetics and Metabolism vol. 88, Issue 3, Jul. 2006, pp. 244-255.

Nitschke, Y et al., "Npp1 promotes atherosclerosis in ApoE knockout mice," Journal of Cellular and Molecular Medicine, vol. 15(11):2273-2283 (2011).

Nitschke, Y., et al., "ENPP1-Fc prevents neointima formation in generalized arterial calcification of infancy through the generation of AMP," Experimental and Molecular Medicine, Oct. 2018, vol. 50, No. 10, Article 139, 12 pages.

Nitschke, Y., et al., "Generalized arterial calcification of infancy and pseudoxanthoma elasticum: two sides of the same coin," Frontiers in Genetics 2012, vol. 3 302, 3 pages.

O'Neill, et al., "Treatment with pyrophosphate inhibits uremic vascular calcification," International Society of Nephrology, 512-517, Mar. 2011.

Oganesyan, et al., "Structural characterization of a human Fc fragment engineered for extended serum half-life," Molecular Immunology vol. 46, No. 8-9, 2009, pp. 1750-1755.

Ogilvie, et al., Identification and partial characterization of an adenosine(5')tetraphospho(5')adenosine hydrolase on intact bovine aortic endothelial cells, Biochem J. 259(1), 1989, 97-103.

Okawa, et al., "Mutation in Npps in a mouse model of ossification of the posterior longitudinal ligament of the spine", Nat Genet. 19(3), Jul. 1998, 271-273.

(56) References Cited

OTHER PUBLICATIONS

Chen, et al., "Fusion Protein Linkers: Property, Design and Functionality", Adv Drug Deliv Rev., 65 (10), pp. 1357-1369, Oct. 15, 2013 (Oct. 15, 2013).

Ferreira, C., et al., "Prospective phenotyping of long-term survivors of generalized arterial calcification of infancy (GACI)," Genet Med. Feb. 2021;23(2):396-407.

Genbank Accession No. XP _006144365.1, Retrieved from the Internet «https://www.ncbi.nlm.nih.gov/protein/XP_006144365.1? report=genbank&log$=protalign&blast_rank=92&RI D=X9E 1 SC3Z016», Retrieved on Feb. 20, 2024.

Goding , et al., "Ecto-phosphodiesterase/pyrophosphatase of lymphocytes and non-lymphoid cells: Structure and function of the PC-1 family," Immunological Reviews, 161: 11-26 (1998).

Kassim, et al. (Clinical Advances in Hematology & Oncology vol. 14, Issue 5 May 2016 pp. 307-309).

Koike, et al., "The N-terminal hydrophobic sequence of autotaxin (ENPP2) functions as a signal peptide", Genes to Cells, 11 (2), pp. 133-142, Jan. 4, 2006.

Luthje, et al., Diadenosine triphosphate (Ap3A) mediates human platelet aggregation by liberation of ADP, Biochem Biophys Res Commun. 118(3) , 1984 , 704-709.

NCBI Accession No. NM_006208, Mar. 2001.

Nitschke, Y., et al., "Generalized arterial calcification of infancy and pseudoxanthoma elasticum can be caused by mutations in either ENPP1 or ABCC6," Am J Hum Genet. Jan. 13, 2012;90(1):25-39.

Nitschke, Y., et al., "Inherited Arterial Calcification Syndromes: Etiologies and Treatment Concepts," Curr Osteoporos Rep. Aug. 2017;15(4):255-270.

Okada, et al., "Scalable purification of adeno-associated virus serotype 1 (AAV1) and AAV8 vectors, using dual ion-exchange adsorptive membranes", Human Gene Therapy vol. 20, 2009, 1013-1021.

Printout of bleeding disorders from the American Society of Hematology, downloaded Sep. 11, 2017 from world wide web.iematology. org/Patients?Bleeding.aspx, 5 pages.

Yin, et al. "Glycoengineering of Chinese hamster ovary cells for enhanced erythropoietin N-glycan branching and sialylation." Biotechnology and bioengineering 112.11 (2015): 2343-2351.

Otero, J., et al., "Severe Skeletal Toxicity From Protracted Etidronate Therapy for Generalized Arterial Calcification of Infancy," Journal of Bone and Mineral Research, 2013, vol. 28, No. 2, pp. 419-430.

Papadakis, et al., "Promoters and Control Elements: Designing Expression Cassettes for Gene Therapy", Current Gene Therapy, 2004, 4, 89-113.

Parati et al. 2016; "Hypertension in chronic kidney disease Part 1." Hypertension. 67(6): 1093-1101.

Parfitt, et al., "Bone histomorphometry: Standardization of nomenclature, symbols, and units: Report of the asbmr histomorphometry nomenclature committee", Journal of Bone and Mineral Research vol. 2, 1987, 595-610.

Pharmacokinetic Control of Biopharmaceuticals, Journal of Pharmaceutical Science and Technology, Japan, 2014, 27-32 (Partial Translation).

Rashdan, N.A. et al., "New perspectives on rare connective tissue calcifying diseases," Current Opinion in Pharmacology, 28:14-23 (2016).

Rath, et al. "Fc-fusion proteins and FcRn: structural insights for longer-lasting and more effective therapeutics." Critical reviews in biotechnology 35.2 (2015): 235-254.

Ratkalkar, et al., "Mechanisms of Stone Formation", Clin Rev Bone Miner Metab. 9(3-4), 2011, 187-197.

Rezg, R., et al., "Inhibitors of Vascular Calcification as Potential Therapeutic Targets", J. Nephrol, Jul.-Aug. (2011), vol. 24, No. 4: pp. 416-427.

Robbie, et al. "A novel investigational Fc-modified humanized monoclonal antibody, motavizumab-YTE, has an axtended half-life in healthy adults." Antimicrobial agents and chemotherapy 57.12 (2013): 6147-6153.

Rogers, et al. "Recombinant human serum albumin fusion proteins and novel applications in drug delivery and therapy." Current pharmaceutical design 21.14 (2015): 1899-1907. Abstract.

Rosenfeld, et al., "Adenovirus-Mediated Transfer of a Recombinant Alpha 1-Antitrypsin Gene to the Lung Epithelium in Vivo", Science vol. 252, 1991, 431-434.

Rosenfeld, et al., "In Vivo Transfer of the Human Cystic Fibrosis Transmembrane Conductance Regulator Gene to the Airway Epithelium", 1992, Cell 68: 143-155.

Rutsch, et al., "Mutations in ENPP1 are associated with 'idiopathic' infantile arterial calcification," Nature Genetics, 34: (4) 379-381 (2003).

Rutsch, F. et al., "Genetics in Arterial Calcification Pieces of a Puzzle and Cogs in a Wheel," Circulation Research, vol. 109:578-592 (2011).

Rutsch, F. et al., "Hypophosphatemia, Hyperphosphaturia, and Bisphosphonate Treatment Are Associated With Survival Beyond Infancy in Generalized Arterial Calcification of Infancy," Circ Cardiovasc Genet., vol. 1(2): 133-140 (2008).

Sahota, et al., "Novel cystine ester mimics for the treatment of cystinuria-induced urolithiasis in a knockout mouse model", Urology 2014, 84(5): 1249 e9-15.

Sakagami, et al., Biochemical and molecular characterization of a novel choline-specific glycerophosphodiester phosphodiesterase belonging to the nucleotide pyrophosphatase/phosphodiesterase family, J Biol Chem. 280 ,24) ,2005 ,23084-23093.

Saunders, et al., "Identification of small-molecule inhibitors of autotaxin that inhibit melanoma cell migration and invasion" Mol. Cancer Ther. 7(10): 3352-62 (2008).

Saunders, et al., Kinetic analysis of autotaxin reveals substrate-specific catalytic pathways and a mechanism for lysophosphatidic acid distribution, J Biol Chem. 286(34), 2011,30130-30141.

Sayer "Progress in understanding the genetics of calcium-containing nephrolithiasis." Journal of the American Society of Nephrology 28.3 (2017): 748-759.

Schetter, et al., "Nucleoporins NPP-1, NPP-3, NPP-4, NPP-11 and NPP-13 are required for proper spindle orientation in C. elegans", Dev Biol. 289(2), Jan. 15, 2006, 360-371.

Schmidt, "Fusion Proteins as Biopharmaceuticals—Applications and Challenges," Current Opinion in Drug Discovery & Development, 12:1-12 (2009).

Schwartz, et al., "Clinical Evaluation of Live, Oral Types 1,2, and 5 Adenovirus Vaccines", American Review of Respiratory Disease vol. 109, 1974, 233-238.

Serrano, R. et al., "Mono-allelic and bi-allelic ENPP1 deficiency promote post-injury neointimal hyperplasia associated with increased C/EBP homologous protein expression", Atherosclerosis, vol. 233 (2):493-502 (2014).

Shankar , et al., "Progeria-A Brief Review", International Journal of Pharma and Bio Sciences 2, 2010, 1-14.

Shaw, G., et al., "Preferential transformation of human neuronal cells by human adenoviruses and the origin of HEK 293 cells," FASEB J. 16, 2002, 19 pages.

Sheehan , et al., "Genetic modifiers of sickle cell anemia in the BABY HUG cohort: influence on laboratory and clinical phenotypes", Am J Hematol. 88(7), 2013, 571-576.

Shimamura, et al., "A Progressive Glomerulosclerosis Occuring in Partial Five-sixths Nephrectomized Rats", Am. J. Pathol. 1975, 79(1): 95-106.

Silcox , et al., "Measurement of inorganic pyrophosphate in biological fluids. Elevated levels in some patients with Ostecorthritis, pseudogout, acromegaly, and uremia", J Clin Invest. 52(8), Aug. 1973, 1863-1870.

Singer, M., et al., Genes and Genomes, "Mir", Moscow, 1998, vol. 1, pp. 1-369, in Russian. English translation of relevant parts.

Siu, S., et al., "Variable patterns of ectopic mineralization in Enpp1asj-2J mice, a model for generalized arterial calcification of infancy," Oncotarget, 2016, vol. 7, No. 51, pp. 83837-83842.

Stefan , et al., "NPP-type ectophosphodiesterases: unity in diversity. ", Trends Biochem Sci. 30(10), Oct. 2005, 542-550.

(56) References Cited

OTHER PUBLICATIONS

Terkeltaub , "Physiologic and pathologic functions of the NPP nucleotide pyrophosphatase/phosphodiesterase family focusing on NPP1 in calcification.", Purinergic Signal. 2(2), Jun. 2, 2006, 371-377.

Tsai , et al., "The Ectoenzyme E-NPP3 Negatively Regulates ATP—Dependent Chronic Allergic Responses by basophils and Mast Cells", Immunity 42, Feb. 2015, 279-293.

UniProt Accession No. O14638, ENPP3 Human, Jan. 7, 2015 [online]. [Retrieved on Jan. 19, 2017]. Retrieved from the internet <URL: http://www.uniprot.org/uniprot/O14638.txt?version=133>.

Uniprot, Accession No. P22413, 2009, www.uniprot.org. (Year: 2009).

Van Meeteren , et al., "Inhibition of autotaxin by lysophosphatidic acid and sphingosine 1-phosphate", J Biol Chem. 280(22), Jun. 2005, 21155-21161.

Villa-Bellosta, et al., "Defective Extracellular Pyrophosphate Metabolism Promotes Vascular Calcification in a Mouse Model of Hutchinson-Gilfrd Progeria Syndrome That is Ameliorated on Pyrophosphate Treatment", Circulation vol. 127, Issue 24, 2013, 2442-2451.

Virag, et al., " Producing Recombinant Adeno-Associated Virus in Foster Cells: Overcoming Production Limitations Using a Baculovirus-Insect Cell Expression Strategy", Human Gene Therapy 20: 807-817 (2009).

Vollmayer, et al., Hydrolysis of diadenosine polyphosphates by nucleotide pyrophosphatases/phosphodiesterases, Eur J Biochem. 270(14) ,2003 ,2971-2978.

Wagner, et al., "Nucleotide sequence of the thymidine kinase gene of herpes simplex virus type 1", Proc. Natl. Acad. Sci. USA vol. 78, No. 3, 1981, 1441-1445.

Wang, et al., "Pharmacokinetic and Biodistribution Studies of a Bone-targeting Drug Delivery System Based on N-(2-Hydroxypropyl)methacrylamide (HPMA) Copolymers," Molecular Pharmaceutics 3(6): 717-725 (2006).

Ware, et al., "Targeted disruption of the low-affinity leukemia inhibitory factor receptor gene causes placental, skeletal, neural and metabolic defects and results in perinatal death", Development 121, 1283-1299 (1995).

Whisstock, et al., "Prediction of proteinfunction fromprotein sequence and structure", Quarterly Reviews of Biophysics 36, 3 (2003), pp., 2003, 307-340.

Witkowski , et al., "Conversion of a Beta-Ketoacyl Synthase to a Malonyl Decarboxylase by Replacement of the Active-Site Cysteine With Glutamine", Biochemistry 38(36), Sep. 1999, 11643-11650.

Wu, et al., "Hyperuricemia and urate nephropathy in urate oxidase-deficient mice", Proc. Natl. Acad. Sci. USA vol. 91, 742-746 (1994).

Wu, et al., "Interstitial Calcinosis in Renal Papillae of Genetically Engineered Mouse Models: Relation to Randall's Plaques", Urolithiasis 43, 65-76 (2015).

Yamamoto, et al., "Identification of a Functional Promoter in the Long Terminal Repeat of Rous Sarcoma Virus", Cell vol. 22, 1980, 787-797.

Zee, et al., "α-Lipoic acid treatment prevents cystine urolithiasis in a mouse model of cystinuria", Nat Med. 2017, 23(3): 288-290.

Zettervall, S., et al., "Association of arterial calcification with chronic limb ischemia in patients with peripheral artery disease," Journal of Vascular Surgery, Feb. 2018, vol. 67, No. 2, pp. 507-513.

Zhang , et al., "The interaction of cationic polymers and their bisphosphonate derivatives with hydroxyapatite", Macromol Biosci. 7(5), May 10, 2007, 656-670 (Abstract Only).

Zhang, et al., "Adenovirus-Adeno-Associated Virus Hybrid for Large-Scale Recombinant Adeno-Associated Virus Production", Human Gene Therapy 2009, vol. 20, No. 9, 922-929.

Zhang, et al., Investigation of the role of ENPP1 and TNAP genes in chondrocalcinosis, Rheumatology, vol. 46, Issue 4, Apr. 2007, pp. 586-589.

Japan Patent Office, Notice of Reasons for Refusal for Japanese Patent Application No. 2022-575745, dated May 21, 2025 with English translation, 10 pages.

[No Author Listed] "Breeding Strategies for Maintaining Colonies of Laboratory Mice: A Jackson Laboratory Resource Manual", 2007, 1-29.

Agapov, et al., "Noncytopathic Sindbis virus RNA vectors for heterologous gene expression", Proc. Natl. Acad. Sci. USA vol. 95, 1998, 12989-12994.

Albright, et al., "ENPP1-Fc prevents mortality and vascular calcifications in rodent model of generalized arterial calcification of infancy", Nat Commun. 6, 2015, 10006.

Albright, et al., "Molecular basis of purinergic signal metabolism by ectonucleotide pyrophosphatase/phosphodiesterases 4 and 1 and implications in stroke", J Biol Chem. 289(6) ,2014 , 3294-3306.

Albright, et al., "NPP4 is a procoagulant enzyme on the surface of vascular endothelium", Blood. 120(22) ,2012 , 4432-4440.

Altschul, et al., "Basic Local Alignment Search Tool", Journal of Molecular Biology, vol. 215, Issue 3, 1990, 403-410.

Anonymous , "UPI000511D809", Retrieved from the Internet Mar. 7, 2019, <https://www.uniprot.org/uniparc/UPI000 511D809>, Oct. 2014.

Apschner, A., et al., "Pathological mineralization in a zebrafish enpp1 mutant exhibits features of Generalized Arterial Calcification of Infancy (GACI) and Pseudoxanthoma Elasticum (PXE)", Disease Models & Mechanisms, Jul. 1, 2014, 21 pages.

Ayuso, et al., Production, Purification and Characterization of Aden-Associated Vectors, Current Gene Therapy 2010, 10:423-436.

Baheti et al., "Excipients used in lyophilization of small molecules" IPEC-Americas Inc., p. 41-54, Jun. 2010.

Beck et al., "Therapeutic Fc-fusion Proteins and Peptides as Successful Alternatives to Antibodies," 3:5, 415-416 (2011).

Belisário , et al., "Association between ENPP1 K173Q and stroke in a newborn cohort of 395 Brazilian children with sickle cell anemia", Blood. 126(10), 2015, 1259-1260.

Belli, et al., "Identification and characterization of a soluble form of the plasma cell membrane glycoprotein PC-1 (5'-nucleotide phosphodiesterase)," European Journal of Biochemistry, 217, 421-428, Feb. 1993.

Benoist, et al., "In vivo sequence requirements of the SV40 early promoter region", Nature 290, 1981, 304-310.

Bertrand, et al., "Decreased levels of nucleotide pyrophosphatase phosphodiesterase 1 are associated with cartilage calcification in osteoarthritis and trigger osteoarthritic changes in mice", Annals of the Rheumatic Diseases vol. 71, 2012, 1249-1253.

Blytt, et al., "Assay of Covalent Intermediate of 5'—Nucleotide Phosphodiesterase" Analytical Biochemistry vol. 147, Issue 2, 1985, 517-520.

Boshart, et al., "A Very Strong Enhancer Is Located Upstream of an Immediate Early Gene of Human Cytomegalovirus," Cell vol. 41, Issue 2, 1985, 521-530.

Braddock, et al., "Protein Engineering and Glycan Optimization Improves Pharmicokinetics of an Enzyme Biologic 10-fold," FASEB Journal vol. 33, No. Suppl. 1, 2019, p. 801.1 (Abstract).

Buckley , et al., "Plasma cell membrane glycoprotein PC-1. cDNA cloning of the human molecule, amino acid sequence, and chromosomal location", J Biol Chem. 265(29), Oct. 1990, 17506-17511.

Caballero , et al., "Impaired urinary osteopontin excretion in Npt2a-/-mice", Am J Physiol Renal Physiol. 312(1), 2017, F77-F83.

Casales, et al., "Development of a new noncytopathic Semliki Forest virus vector providing high expression levels and stability", Virology 376 (2008) 242-251.

Chamow, S. M. et al., "Immunoadhesins: Principles and Applications," Trends Biotechnol., 14(2); 52-60 (1996).

Cheung, et al., "Analysis of Inorganic Pyrophosphate at the Picomole Level", Analytical Biochemistry vol. 83, 1977, 61-63.

"Chronic Renal Failure: From the Perspective of Internal Medicine", Clinical Imagiology 21(11), 2005, 1142-1149 Partial Translation).

Cimpean, et al., "Substrate-specifying determinants of the nucleotide pyrophosphatases/phosphodiesterases NPP1 and NPP2", Biochem J. 381(Pt 1) ,2004, 71-77.

Colella, et al., "Emerging Issues in AAV-Mediated In Vivo Gene Therapy", Molecular Therapy: Methods & Clinical Development vol. 8, 2018, 87-104.

(56) References Cited

OTHER PUBLICATIONS

Dabisch-Ruthe, M., et al., "Pyrophosphates as a major inhibitor of matrix calcification in Pseudoxanthoma elasticum," Journal of Dermatological Science, Elsevier, Amsterdam, NL, vol. 75, No. 2, May 17, 2014, pp. 109-120.

Dabisch-Ruthe, M., et al., "Variants in genes encoding pyrophosphate metabolizing enzymes are associated with Pseudoxanthoma eslasticum," Clinical Biochemsitry, 2014, vol. 47, No. 15, pp. 60-67.

Dall'Acqua, et al. "Increasing the affinity of a human IgG1 for the neonatal Fc receptor: biological consequences." The Journal of Immunology 169.9 (2002): 5171-5180.

Dasgupta , et al., "Mutations in SLC34A3/NPT2c are associated with kidney stones and nephrocalcinosis", J Am Sac Nephrol. 25(10), 2014, 2366-2375.

Di Lullo et al. 2015; Left ventricular hypertrophy in chronic kidney disease patients: From pathophysiology to treatment. CardioRenal Medicine. 5: 254-266.

Dimatteo, et al., "Role of somatomedin-B-like domains on ENPP1 inhibition of insulin signaling," Biochimica et Biophysica Acta (BBA)—Molecular Cell Research vol. 1833, No. 3, 2012, pp. 552-558.

Dohler, et al. "Crystal structure and substrate binding mode of ectonucleotide phosphodiesterase/pyrophosphatase-3 (NPP3)," Scientific reports 8.1 (2018): 1-13.

Eller, et al. "Impact of ENPP1 genotype on arterial calcification in patients with end-stage renal failure", Nephrol Dial Transplant. 23(1), 2008, 321-327.

Fang, L., et al., "Pdgf C Is A Selective alpha Platelet-Derived Growth Factor Receptor Agonist That Is Highly Expressed in Platelet alpha Granules and Vascular Smooth Muscle," Arterioscler. Thromb. Vasc. Biol. 24, 2004, 787-92.

Flanagan , et al., "Genetic mapping and exome sequencing identify 2 mutations associated with stroke protection in pediatric patients with sickle cell anemia", Blood. 121(16), 2013, 3237-3245.

Flanagan, et al., "Soluble Fc fusion proteins for biomedical research," in Monoclonal Antibodies, Methods and Protocols, et. By Albitar, Methods in Molecular Biology, (2007) vol. 378, 33-52.

Fleisch , et al., "Inhibitors and promoters of stone formation", Kidney Int. 13(5), 1978, 361-371.

Frolov, et al., "Selection of RNA Replicons Capable of Persistent Noncytopathic Replication in Mammalian Cells", Journal of Virology, 1999, 3854-3865.

Gijsbers , et al., "Functional characterization of the non-catalytic ectodomains of the nucleotide pyrophosphatase/phosphodiesterase NPP1", Biochem J. 371(Pt 2), Apr. 15, 2003, 321-330.

Gijsbers , et al., "The hydrolysis of lysophospholipids and nucleotides by autotaxin (NPP2) involves a single catalytic site," FEBS Letters, 538:60-64 (2003).

Gijsbers, et al., "Structural and Catalytic Similarities between Nucleotide Pyrophosphatases/Phosphodiesterases and Alkaline Phosphatases", The Journal of Biological Chemistry vol. 276, No. 2, 2001, 1361-1368.

Goding , et al., "Physiological and pathophysiological functions of the ecto-nucleotide pyrophosphatase/phosphodiesterase family", Biochim Biophys Acta. 1638(1), 2003, 1-19.

Goldman, et al., Hydrolysis of diadenosine $5',5''-P',PА$-triphosphate (Ap3A) by porcine aortic endothelial cells, Circ Res. 59(3) , 1986 , 362-366.

Green, et al., "Analysis of human tonsil and cancer DNAs and RNAs for DNA sequences of group C (serotypes 1, 2, 5, and 6) human adenoviruses", Proc. Natl. Acad. Sci. USA 1979, vol. 76, No. 12, 6606-6610.

Guan, et al., "Peptide-Targeted Polyglutamic Acid Doxorubicin Conjugates for the Treatment of αvB6-Positive Cancers," Bioconjug Chem., 19:1813-1821 (2008).

Guanabens, N., et al., "Calcific Periarthritis as the Only Clinical Manifestation of Hypophosphatasia in Middle-Aged Sisters," Journal of Bone ande Mineral Research, 2014, vol. 29, No. 4, pp. 929-934.

Guo et al., "Clinical outcomes of various continued antiplatelet therapies in patients who were administered DAPT following the implantation of drug-eluting stents and developed gastrointestinal hemorrhage", Exp Ther Med. 12(2), Aug. 2016, 1125-1129.

Halbert, et al., "AAV-Mediated Gene Transfer to Mouse Lungs", Methods in Molecular Biology, vol. 246, 2004, 201-212.

Huang, "Receptor-Fc Fusion Therapeutics, traps, and MIMETIBODY Technology," Current Opinion in Biotechnology, 20:692-699 (2009).

Pakula et al., Genetic analysis of protein stability and function, Ann. Rev. Genet., 23: 289-310 (Dec. 1989).

Keskin et al., A new, structurally nonredundant, diverse data set of protein-protein interfaces and its implications, Protein Sci., 13(4): 1043-1055 (Apr. 2004).

* cited by examiner

```
  1 MERDGCAGGG SRGGEGGRAP REGPAGNGRD RGRSHAAEAP GDPQAAASLL
 51 APMDVGEEPL EKAARARTAK DPNTYKVLSL VLSVCVLTTI LGCIFGLKPS
101 CAKEVKSCKG RCFERTFGNC RCDAACVELG NCCLDYQETC IEPEHIWTCN
151 KFRCGEKRLT RSLCACSDDC KDKGDCCINY SSVCQGEKSW VEEPCESINE
201 PQCPAGFETP PTLLFSLDGF RAEYLHTWGG LLPVISKLKK CGTYTKNMRP
251 VYPTKTFPNH YSIVTGLYPE SHGIIDNKMY DPKMNASFSL KSKEKFNPEW
301 YKGEPIWVTA KYQGLKSGTF FWPGSDVEIN GIFPDIYKMY NGSVPFEERI
351 LAVLQWLQLP KDERPHFYTL YLEEPDSSGH SYGPVSSEVI KALQRVDGMV
401 GMLMDGLKEL NLHRCLNLIL ISDHGMEQGS CKKYIYLNKY LGDVKNIKVI
451 YGPAARLRPS DVPDKYYSFN YEGIARNLSC REPNQHFKPY LKHFLPKRLH
501 FAKSDRIEPL TFYLDPQWQL ALNPSERKYC GSGFHGSDNV FSNMQALFVG
551 YGPGFKHGIE ADTFENIEVY NLMCDLLNLT PAPNNGTHGS LNHLLKNPVY
601 TPKHPKEVHP LVQCPFTRNP RDNLGCSCNP SILPIEDFQT QFNLTVAEEK
651 IIKHETLPYG RPRVLQKENT ICLLSQHQFM SGYSQDILMP LWTSYTVDRN
701 DSFSTEDFSN CLYQDFRIPL SPVHKCSFYK NNTKVSYGFL SPPQLNKNSS
751 GIYSEALLTT NIVPMYQSFQ VIWRYFHDTL LRKYAEERNG VNVVSGPVFD
801 FDYDGRCDSL ENLRQKRRVI RNQEILIPTH FFIVLTSCKD TSQTPLHCEN
851 LDTLAFILPH RTDNSESCVH GKHDSSWVEE LLMLHRARIT DVEHITGLSF
901 YQQRKEPVSD ILKLKTHLPT FSQED (SEQ ID NO: 1)
```

FIGURE 1

Human Enpp1
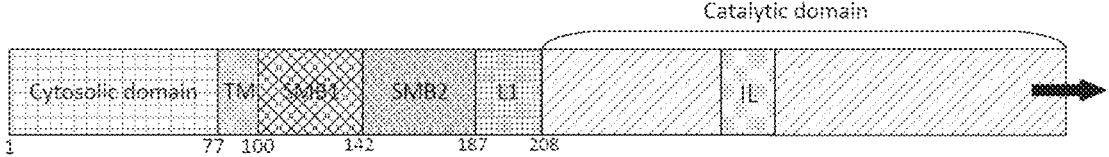
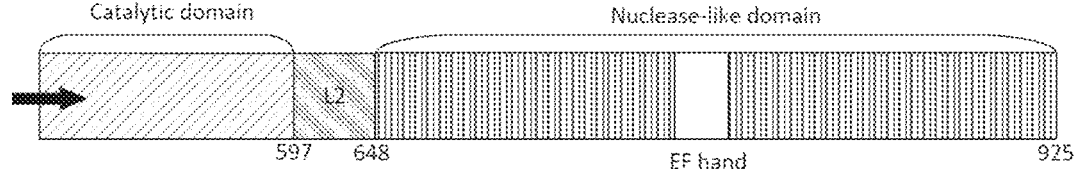
FIGURE 2

```
  1  PSCAKEVKSC  KGRCFERTFG  NCRCDAACVE  LGNCCLDYQE  TCIEPEHIWT
 51  CNKFRCGEKR  LTRSLCACSD  DCKDKGDCCI  NYSSVCQGEK  SWVEEPCESI
101  NEPQCPAGFE  TPPTLLFSLD  GFRAEYLHTW  GGLLPVISKL  KKCGTYTKNM
151  RPVYPTKTFP  NHYSIVTGLY  PESHGIIDNK  MYDPKMNASF  SLKSKEKFNP
201  EWYKGEPIWV  TAKYQGLKSG  TFFWPGSDVE  INGIFPDIYK  MYNGSVPFEE
251  RILAVLQWLQ  LPKDERPHFY  TLYLEEPDSS  GHSYGPVSSE  VIKALQRVDG
301  MVGMLMDGLK  ELNLHRCLNL  ILISDHGMEQ  GSCKKYIYLN  KYLGDVKNIK
351  VIYGPAARLR  PSDVPDKYYS  FNYEGIARNL  SCREPNQHFK  PYLKHFLPKR
401  LHFAKSDRIE  PLTFYLDPQW  QLALNPSERK  YCGSGFHGSD  NVFSNMQALF
451  VGYGPGFKHG  IEADTFENIE  VYNLMCDLLN  LTPAPNNGTH  GSLNHLLKNP
501  VYTPKHPKEV  HPLVQCPFTR  NPRDNLGCSC  NPSILPIEDF  QTQFNLTVAE
551  EKIIKHETLP  YGRPRVLQKE  NTICLLSQHQ  FMSGYSQDIL  MPLWTSYTVD
601  RNDSFSTEDF  SNCLYQDFRI  PLSPVHKCSF  YKNNTKVSYG  FLSPPQLNKN
651  SSGIYSEALL  TTNIVPMYQS  FQVIWRYFHD  TLLRKYAEER  NGVNVVSGPV
701  FDFDYDGRCD  SLENLRQKRR  VIRNQEILIP  THFFIVLTSC  KDTSQTPLHC
751  ENLDTLAFIL  PHRTDNSESC  VHGKHDSSWV  EELLMLHRAR  ITDVEHITGL
801  SFYQQRKEPV  SDILKLKTHL  PTFSQED  (SEQ ID NO: 2)
```

FIGURE 3

```
  1 WVEEPCESIN EPQCPAGFET PPTLLFSLDG FRAEYLHTWG GLLPVISKLK
 51 KCGTYTKNMR PVYPTKTFPN HYSIVTGLYP ESHGIIDNKM YDPKMNASFS
101 LKSKEKFNPE WYKGEPIWVT AKYQGLKSGT FFWPGSDVEI NGIFPDIYKM
151 YNGSVPFEER ILAVLQWLQL PKDERPHFYT LYLEEPDSSG HSYGPVSSEV
201 IKALQRVDGM VGMLMDGLKE LNLHRCLNLI LISDHGMEQG SCKKYIYLNK
251 YLGDVKNIKV IYGPAARLRP SDVPDKYYSF NYEGIARNLS CREPNQHFKP
301 YLKHFLPKRL HFAKSDRIEP LTFYLDPQWQ LALNPSERKY CGSGFHGSDN
351 VFSNMQALFV GYGPGFKHGI EADTFENIEV YNLMCDLLNL TPAPNNGTHG
401 SLNHLLKNPV YTPKHPKEVH PLVQCPFTRN PRDNLGCSCN PSILPIEDFQ
451 TQFNLTVAEE KIIKHETLPY GRPRVLQKEN TICLLSQHQF MSGYSQDILM
501 PLWTSYTVDR NDSFSTEDFS NCLYQDFRIP LSPVHKCSFY KNNTKVSYGF
551 LSPPQLNKNS SGIYSEALLT TNIVPMYQSF QVIWRYFHDT LLRKYAEERN
601 GVNVVSGPVF DFDYDGRCDS LENLRQKRRV IRNQEILIPT HFFIVLTSCK
651 DTSQTPLHCE NLDTLAFILP HRTDNSESCV HGKHDSSWVE ELLMLHRARI
701 TDVEHITGLS FYQQRKEPVS DILKLKTHLP TFSQED (SEQ ID NO: 3)
```

FIGURE 4

```
Mouse    WVEETCESIDTPECPAEFESPPTLLFSLDGFRAEYLHTWGGLLPVISKLKNCGTYTKNMR      60
Cow      WAEEECDSIDEPQCPAGFETPPTLLFSLDGFRAEYLHTWGGLLPVISKLKTCGTYTKNMR      60
Rabbit   WVEETCENINEPQCPEGFENPPTLLFSLDGFRAEYLHTWGGLLPVISKLKKCGTYAKNMR      60
Human    WVEEPCESINEPQCPAGFETPPTLLFSLDGFRAEYLHTWGGLLPVISKLKKCGTYTKNMR      60
Baboon   WVEEPCESINEPQCPAGFETPPTLLFSLDGFRAEYLHTWGGLLPVISKLKKCGTYTKNMR      60
         * .** *:.*; *;** .** ******************** .****:.****

Mouse    PRYPTKTFPNHYSIVTGLYPESHGIIDNKMYDPKMNASFSLKSKEKFNPLWYKGQPIWVT     120
Cow      PVYPTKTFPNHYSIVTGLYPESHGIIDNNIYDPQMNANFALKNKEKFNPEWYKGEPIWLT     120
Rabbit   PVYPTKTFPNHYSIVTGLYPESHGIIDNKMYDPKMNASFGLKSKEKFNPEWYKGEPIWLT     120
Human    PVYPTKTFPNHYSIVTGLYPESHGIIDNKMYDPKMNASFSLKSKEKFNPEWYKGEPIWVT     120
Baboon   PVYPTKTFPNHYSIVTGLYPESHGIIDNKMYDPKMNASFSLKSKELFNPEWYKGEPIWVT     120
         *:*********************** .:****.*** *;.** :****** ****;****;*

Mouse    ANHQEVKSGTYFWPGSDVEIDGILPDIYKVYNGSVPFEERILAVLEWLQLPSHERPHFYT     180
Cow      AKYQGLKTGTFFWPGSDVKINGIFPDIYKIYNVSVPFEERILAILKWLQLPKDERPHFYT     180
Rabbit   AKYQGLRSGTFFWPGSDVKINGIFPDIYKIYNGSVPFEERILAILKWLRLPKDERPHFYT     180
Human    AKYQGLKSGTFFWPGSDVEINGIFPDIYKMYNGSVPFEERILAVLQWLQLPKDERPHFYT     180
Baboon   AKYQGLKSGTFFWPGSDVEINGIFPDIYKMYNGSVPFEERILAVLQWLQLPKDERPHFYT     180
         *;:*  ;;:**;*****:*;**;*****;** ********:**:**;;*****;*******

Mouse    LYLEEPDSSGHSHGPVSSEVIKALQKVDRLVGALMDGLKDLGLDKCLNLILISDHGMEQG     240
Cow      LYLEEPDSSGHSYGPVSSEVIKALQRVDNMVGMLMDGLKELNLHRCLNLILISDHGMEQG     240
Rabbit   LYLEEPDSSGHSYGPVSSEVIKALQRVDNMVGMLMDGLKELNLHQCLNLILISDHGMEQG     240
Human    LYLEEPDSSGHSYGPVSSEVIKALQRVDGMVGMLMDGLKELNLHRCLNLILISDHGMEQG     240
Baboon   LYLEEPDSSGHSYGPVSSEVIKALQRVDNMVGMLMDGLKELNLHRCLNLILVSDHGMEQG     240
         ***********;*********;*** :** ;***********;*,*;;******;*******

Mouse    SCKKYVYLNKYLGDVNRVKVVYSPAARLRPTDVPETYYSFNYEALAKNLSCREPNQHFRP     300
Cow      SCKKYVYLNKYLGDTIDYKVVYGPAARLRPSDVPDKYYSFDYEGIAKNLSCQEPNQHFKP     300
Rabbit   SCKKYIYLNKYLGDTKNIKVIYGPAARLRPSDVPEKYYSFNYENIARNLSCREPNQHFKP     300
Human    SCKKYIYLNKYLGDVKNIKVIYGPAARLRPSDVPDKYYSFNYEGIARNLSCREPNQHFKP     300
Baboon   SCKKYIYLNKYLGDVKNIKVIYGPAARLRPSDVPDKYYSFNYEGIARNLSCREPNQHFKP     300
         *****;*******;; ;; **;**********;***;;****;** ;**;****;*******;

Mouse    YLKPFLPKRLHFAKSDRIEPLTFYLDPQWQLALNPSERKYCGSGFHGSDNLFSNWQALFI     360
Cow      YLKHFLPKRLHPAKNDRIERLTFYLDPQWQLALNPSERKYCGSGFHGSDNTLNMQALFI     360
Rabbit   YLKHFLPKRLHFAKSDRIEPLTFYLDPQWQLALSPSERKYCGSGFHGSDNVFSNWQALFV     360
Human    YLKHFLPKRLHFAKSDRIEPLTFYLDPQWQLALNPSERKYCGSGFHGSDNVFSNWQALFV     360
Baboon   YLKHFLPKRLHFAKSDRIEPLTFYLDPQWQLALNPSERKYCGSGFHGSDNIFSNWQALFV     360
         ***.*********;**** ;**.*********;*****;*;****** . *.******;
```

FIGURE 5A

```
Mouse   GYGPAFKHGAEVDSFENIEVYNLMCDLLGLIPAPNNGHGSLNHLLKKPIYNPSHPKEEG   428
Cow     GYGPGFKHGTEVDSFENIEVYNLMCDLLNLTPAPNNGTHGSLNHLLSNPVYTPKHPKEVR   428
Rabbit  GYGPGFQHGIEVDSFENIEVYNLMCDLLNLTPAPNNGTHGSLNHLLKNPIYTPKHPKEVQ   428
Human   GYGPGFKHGIEADTFENIEVYNLMCDLLNLTPAPNNGTHGSLNHLLKNPVYTPKHPKEVH   428
Baboon  GYGPGFKHGIEVDTFENIEVYNLMCDLLNLTPAPNNGTHGSLNHLLKNPVYTPKHPKEVH   428
        **** . * . * . *. * . ********** . * ****** . ******** . . * . * . * . ****

Mouse   FLSQCPIKST-SNDLGCTCDPVIVPIKDFEKQLNLTTEDVDDIYH*TVPYGRPRILLKQH   479
Cow     PLVQCPFTRAPRESLDCSCDPSILPIVDFQTQLNLTPAEEKTIKRGALPYGRPRVLQN-S   479
Rabbit  PSVQCPLAGSPRDSLGCSCNPSILPIVDFQTQFNLTTAEEKNINRASLPYGRPRLLQKKS   480
Human   PLVQCPFTRNPRDNLGCSCNPSILPIEDFQTQFNLTVAEEKIIKHETLPYGRPRVLQYEN   480
Baboon  PLIQCPFTRNPRDNLGCSCNPSILPIEDFQTQFNLTVAEEKNIKHETLPYGRPRVLQKFN   480
         ****. .  . * . * . * . * * . ** ** . * . ***  . . * . *  . . . ****** . * .  .

Mouse   RVCLLQQQQFLTGYSLDLLMPLWASYTFLSNDQFSRDDFSNCLYQDLRIPLSPVHKCSYY   539
Cow     TVCLLYQHQFVSGYSRDILMPLWTSYTIGRNDSFSTEDFSNCLYQDLRIPLSPVHKCSFY   539
Rabbit  SVCLLYQHQFVGGYSHDVLMPLWTSYTVNRNDSFSTEDFSNCLYQDLRISFSPIHNCSFY   540
Human   TICLLSQHQFMSGYSQDILMPLWTSYTVDRNDSFSTEDFSNCLYQDFRIPLSPVHKCSFY   540
Baboon  TICLLSQHQFMSGYSQDILMPLWTSYTVDRNDSFSTEDFSNCLYQDFRISLSPVHKCSFY   540
         . *** . * . ** . * . ** * . ***** . *** .  . ** . ** . * . ******* . ** . * . * . * . *

Mouse   KSNSKLSYGFLTPPRLNRVSNHIYSEALLTSNIVPMYQSFQVIWHYLHDTLLQRYAHERN   599
Cow     KNNAKLSYGLLSPPQLHKGSSQVVSEALLTTNIVPMYQSFQVIWHYLHGTLLQRYAEERN   599
Rabbit  KNNAKLSYGFLSPPQLSKDSSQIYSEALLTSNIVPMYQSFQVIWRYFHDTLLQRYAEERN   600
Human   KNNTKVSYGFLSPPQLNKNSGGIYSEALLTTNIVPMYQSFQVIWRYFHDTLLRKYAEERN   600
Baboon  KNNTKVSYGFLSPPQLNKNSAGIYSEALLTTNIVPMYQSFQVIWRYFHDTLLRKYAEERN   600
         * . * . *** . * . * . * . . *  . ** . *** . ***** . ***** . * . * . *** . . * . ***

Mouse   GINVVSGPVFDFDYDGRYDSLEILKQNSRVIRSQEILIPTHFFIVLTSCKQLSETPLECS   659
Cow     GLNVVSGPVFDSDYDGRYDSLETLKQNSKIIRNLEVLIPTHFFLVLTSCKNTSQTPLQCE   659
Rabbit  SINVVSGPVFDSDYDGRYDSSEALKRNRKVIRNQEILIPTHFFIVITSCKNTSQTPLQCD   660
Human   GVNVVSGPVFDFDYDGRKDSLENLRQKRVIRNQEILIPTHFFIVLTSCKDTSQTPLHCE   660
Baboon  GVNVVSGPVFDFDYDGRYDSLEILRQKRAVIRNQEILIPTHFFIVLTSCKDASQTPLHCE   660
         . . ********* ***** ** . *  . . .  . . ** .  . . ***** . *  . ** . . * . ***** . * .

Mouse   ALESSAYILPHRPDNIESCTHGKRESSWVEELLTLHRARVTDVELITGLSFYQDRQESVS   719
Cow     NLDANAFILPHKTDNSESCAHGKHESLWVEELLKLHTARITDVEHITGLSFYQERKEPIS   719
Rabbit  NLDPLAFILPHRSDNSESCVHEKRESSWIEELLMHRARIMDVEHITGLSFYQERKEPVS   720
Human   NLDTLAFILPHRTDNSESCVHGKHDSSWVEELLMLHRARITDVEHITGLSFYQQRKEPVS   720
Baboon  NLDTLAFILPHRTDNSESCLHGKHESSWVEELLMLHRARITDVEHITGLSFYQQRKEPVS   720
          * .  . * . ****** . ** *** *  * . . * .  . * . **** . * ** . *** . ******* . * .  . * .

Mouse   ELLRLKTHLPIFSQED   735
Cow     DILKLKTHLPTPNQED   735
Rabbit  DILKLKTHLPTVSQED   736
Human   DILKLKTHLPTFSQED   736
Baboon  DILKLKTHLPTFSQED   736
         . . * . ****** * .  . . ***
```

FIGURE 5B

```
  1 MESTLTLATE QPVKKNTLKK YKIACIVLLA LLVIMSLGLG LGLGLRKLEK QGSCRKKCFD
 61 ASFRGLENCR CDVACKDRGD CCWDFEDTCV ESTRIWMCNK FRCGETRLEA SLCSCSDDCL
121 QRKDCCADYK SVCQGETSWL EENCDTAQQS QCPEGFDLPP VILFSMDGFR AEYLYTWDTL
181 MPNINKLKTC GIHSKYMRAM YPTKTFPNHY TIVTGLYPES HGIIDNNMYD VNLNKNFSLS
241 SKEQNNPAWW HGQPMWLTAM YQGLKAATYF WPGSEVAING SFPSIYMPYN GSVPFEERIS
301 TLLKWLDLPK AERPRFYTMY FEEPDSSGHA GGPVSARVIK ALQVVDHAFG MLMEGLKQRN
361 LHNCVNIILL ADHGMDQTYC NKMEYMTDYF PRINFFYMYE GPAPRIRAHN IPHDFFSFNS
421 EEIVRNLSCR KPDQHFKPYL TPDLPKRLHY AKNVRIDKVH LFVDQQWLAV RSKSNTNCGG
481 GNHGYNNEFR SMEAIFLAHG PSFKEKTEVE PFENIEVYNL MCDLLRIQPA PNNGTHGSLN
541 HLLKVPFYEP SHAEEVSKFS VCGFANPLPT ESLDCFCPHL QNSTQLEQVN QMLNLTQEEI
601 TATVKVNLPF GRPRVLQKNV DHCLLYHREY VSGFGKAMPM PMWSSYTVPQ LGDTSPLPPT
661 VPDCLRADVR VPPSESQKCS FYLADKNITH GFLYPPASNR TSDSQYDALI TSNLVPMYEE
721 FRKMWDYFHS VLLIKHATER NGVNVVSGPI FDYNYDGHFD APDEITKHLA NTDVPIPTHY
781 FVVLTSCKNK SHTPENCPGW LDVLPFIIPH RPTNVESCPE GKPEALWVEE RFTAHIARVR
841 DVELLTGLDF YQDKVQPVSE ILQLKTYLPT FETTI (SEQ ID NO: 116)
```

FIGURE 6

Human Enpp3
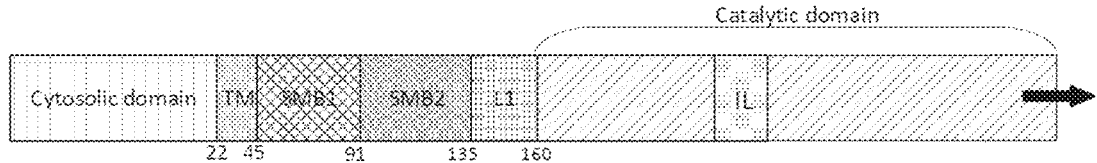
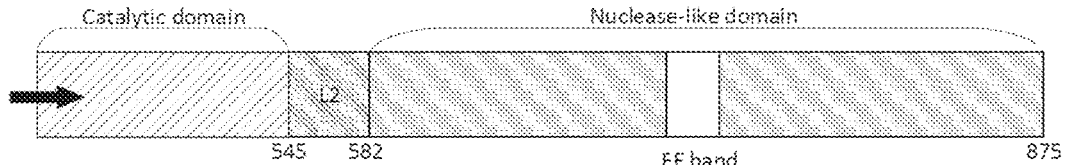
FIGURE 7

SOLUBLE ENPP1 PROTEINS AND USES THEREOF

CROSS-REFERENCE TO RELATED APPLICATIONS

This U.S. Patent application is a continuation of International Patent Application No. PCT/US2021/036494, filed Jun. 8, 2021, which claims the benefit of priority to U.S. provisional application Ser. No. 63/036,833, filed on Jun. 9, 2020. The disclosures of the foregoing applications are hereby incorporated by reference in their entireties.

FEDERAL FUNDING LEGEND

This invention was made with government support under DK121326 awarded by National Institutes of Health. The government has certain rights in the invention.

SEQUENCE LISTING

This application contains a Sequence Listing which has been submitted electronically as a WIPO Standard ST.26 XML file via Patent Center, created on Dec. 7, 2022, is entitled "4427-11400.xml" and is 190.319 bytes in size. The sequence listing is incorporated herein by reference in its entirety.

BACKGROUND OF THE INVENTION

The human ectonucleotide pyrophosphatase (ENPP) protein family comprises seven extracellular, glycosylated proteins (i.e., ENPP1-ENPP7) that hydrolyze phosphodiester bonds. ENPPs are cell-surface enzymes, with the exception of ENPP2, which is exported to the plasma membrane but is cleaved by furin and released into the extracellular fluid. The ENPP enzymes have high degrees of sequence and structural homology, but exhibit a diverse substrate specificity encompassing nucleotides to lipids.

ENPP1 (also known as PC-1) and ENPP3 are type 2 extracellular membrane-bound glycoproteins located on the mineral-depositing matrix vesicles of osteoblasts and chondrocytes, and hydrolyze extracellular nucleotides (principally ATP) into adenosine monophosphate (AMP) and inorganic pyrophosphate (PPi). PPi functions as a potent inhibitor of ectopic tissue mineralization by binding to nascent hydroxyapatite (HA) crystals, thereby preventing the future growth of these crystals. ENPP1 generates PPi via hydrolysis of nucleotide triphosphates (NTPs), Progressive Ankylosis Protein (ANK) transports intracellular PPi into the extracellular space, and Tissue Non-specific Alkaline Phosphatase (TNAP) removes PPi via direct hydrolysis of PPi into Pi.

Ectopic tissue mineralization is associated with numerous human diseases, including chronic joint disease and acutely fatal neonatal syndromes. To prevent unwanted tissue calcification, factors that promote and inhibit tissue mineralization must be kept in tight balance. The balance of extracellular inorganic pyrophosphate (PPi) and phosphate (Pi) is an important regulator of ectopic tissue mineralization. The activity of the three extracellular enzymes— TNAP, ANK, and ENPP1—tightly control the concentration of Pi and PPi in mammals at 1-3 mM and 2-3 pM respectively. PPi is a regulator of biomineralization, inhibiting the formation of basic calcium phosphate from amorphous calcium phosphate.

SUMMARY OF THE INVENTION

The present disclosure is based, at least in part, on the discovery that a large percentage of anti-drug antibodies are generated by mammals against an ENPP1 containing fusion protein bound to a Somatomedin B (SMB) domain of ENPP1. As described in the working examples, following administration of an ENPP1-containing fusion protein to mice and non-human primates, the anti-drug antibodies recovered from these animals primarily recognized the SMB domain region of ENPP1. The disclosure is also based, in part, on the discovery that variant forms of ENPP1 polypeptides, and fusion proteins containing such polypeptides, that lack any SMB domain are enzymatically active, demonstrate enhanced stability over the corresponding SMB domain-containing polypeptides and/or fusion proteins, and are useful for, among other things, inhibiting unwanted calcification in soft tissues.

Somatomedin B is a cysteine-rich peptide that is liberated by proteolysis from Vitronectin. &e, e.g., Leavesley et al. (2013) IUBMB Life 65(10):807-818. The SMB domain contains eight cysteine residues, which form four disulfide bonds, which, based on three-dimensional structure, are buried within the domain forming a covalently bonded core. Id See also Kamikubo et al. (2004) Biochemistry 43:6519-6534. While the disclosure is not bound by any particular theory or mechanism of action, heterogeneity and/or interchangeable or interchanging disulfide bond formation within the SMB structure may be, in part, responsible for the increased propensity for immunogenicity as well as reduced stability observed for ENPP1-containing fusion proteins.

In addition to ENPP1 and Vitronectin, the SMB domain is also found in proteins such as ENPP2, ENPP3, and Placental Protein 11 (PPI 1). Thus, the disclosure features variant forms of SMB domain-containing polypeptides that do not contain the SMB domain(s). In some embodiments, the variant polypeptide is not a variant of a Vitronectin polypeptide. In some embodiments, the variant polypeptide is a variant of ENPP1 (e.g., a variant of a soluble form of ENPP1). In some embodiments, the variant polypeptide is a variant of ENPP2. In some embodiments, the variant is a variant of ENPP3. In some embodiments, the variant is a variant of PP 11. Also featured is a fusion protein comprising one or more of the variant polypeptides and a heterologous protein and/or a conjugate comprising one or more of the variant polypeptides and a heterologous moiety.

In yet another aspect, the disclosure features a soluble ENPP1 polypeptide that lacks both the Somatomedin B (SMB) domain 1 and the SMB domain 2 of ENPP1. In some embodiments, the soluble ENPP1 polypeptide lacks a negatively-charged bone-targeting domain.

In some aspects, the disclosure provides soluble ENPP1 polypeptides. In some aspects, the disclosure provides a soluble ENPP1 polypeptide that lacks both SMB domain 1 and SMB domain 2 of ENPP1. In some aspects, the disclosure provides a soluble ENPP1 polypeptide that lacks both SMB domain 1 and SMB domain 2 of ENPP1, wherein the soluble ENPP1 polypeptide lacks a negatively-charged bone-targeting domain. In some aspects, the disclosure provides a soluble ENPP1 polypeptide that is at least 90% identical to amino acids 190 to 925 of SEQ ID NO: 1, wherein the polypeptide lacks both SMB domain 1 and SMB domain 2 of ENPP1, and wherein the soluble ENPP1 polypeptide lacks a negatively-charged bone-targeting domain. In some embodiments, the soluble ENPP1 polypeptide has a reduced ability to homodimerize as compared to the corresponding wild-type soluble ENPP1 polypeptide.

In some embodiments, the soluble ENPP1 polypeptide comprises one or more amino acid modifications that reduce homodimerization of the ENPP1 polypeptide as compared to the corresponding wild-type soluble ENPP1 polypeptide. In some embodiments, the one or more amino acid modifications reduce homodimerization by at least 1%, 2%, 3%, 4%, 5%, 6%, 7%, 8%, 9%, 10%, 15%, 20%, 30%, 40%, 50%, 60%, 70%, 80%, 90% or 100%. In some embodiments, the polypeptide has reduced affinity for the human insulin receptor (IR) as compared to the corresponding wild-type soluble ENPP1 polypeptide. In some aspects, the disclosure provides a soluble ENPP1 polypeptide comprising an amino acid substitution at at least one of position 816, 817, or 818 relative to SEQ ID NO: 1, wherein the ENPP1 polypeptide demonstrates greater proteolytic resistance to a protease than the corresponding wild-type soluble ENPP1 polypeptide. In some aspects, the disclosure provides a soluble ENPP1 polypeptide comprising a polypeptide that lacks both the SMB domain 1 and the SMB domain 2 of ENPP1, wherein the polypeptide further comprises an amino acid substitution at at least one of position 816, 817, or 818 relative to SEQ ID NO: 1. In some aspects, the disclosure provides a soluble ENPP1 polypeptide comprising an amino acid sequence that is at least 75%, 80%, 85%, 90%, 91%, 92%, 93%, 94%, 95%, 96%, 97%, 98%, 99%, or 100% identical to an amino acid sequence comprising amino acids 190 to 925 of SEQ ID NO: 1, wherein the polypeptide comprises one or more amino acid substitutions at a position of SEQ ID NO: 1 selected from the group consisting of position 816, 817, or 818 relative to SEQ ID NO: 1. In some aspects, the disclosure provides a soluble ENPP1 polypeptide that is at least 90% identical to amino acids 190 to 925 of SEQ ID NO: 1, wherein at least the arginine (R) at position 818 is substituted for another amino acid. In some embodiments, the polypeptide further comprises one or more amino acid substitutions at a position of SEQ ID NO: 1 selected from the group consisting of position 816, 817, or 818 relative to SEQ ID NO: 1. In some embodiments, the ENPP1 polypeptide demonstrates greater proteolytic resistance to a protease than the corresponding wild-type soluble ENPP1 polypeptide. In some embodiments, the greater proteolytic resistance of the ENPP1 polypeptide provides a homogenous composition with protein purity increased by about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, or 300% as compared to a corresponding wild-type soluble ENPP1 polypeptide. In some embodiments, the greater proteolytic resistance of the ENPP1 polypeptide decreases protein cleavage by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, or 300%. In some embodiments, the protease is selected from the group consisting of trypsin or trypsin-like proteases. In some embodiments, the substitution is at position 818 relative to SEQ ID NO: 1. In some embodiments, the arginine (R) at position 818 is substituted with histidine (H). In some embodiments, the amino acid at any one of positions 816. 817, or 818 relative to SEQ ID NO: 1 is substituted with histidine (H). In some embodiments, the soluble ENPP1 polypeptide comprises one or more amino acid substitution with respect to the amino acid sequence of SEQ ID NO: 1 selected from the group consisting of: K816R, K816H, R817H, R817K, R818H, or R818K. In some embodiments, the ENPP1 polypeptide comprises the phosphodiesterase catalytic domain of ENPP1. In some embodiments, the ENPP1 polypeptide lacks one or both of SMB domains 1 and 2. In some embodiments, the polypeptide is at least 90% identical to amino acids 190 to 925 of SEQ ID NO: 1. In some embodiments, the polypeptide is at least 95% identical to amino acids 190 to 925 of SEQ ID NO: 1. In some embodiments, the polypeptide is at least 99% identical to amino acids 190 to 925 of SEQ ID NO: 1. In some embodiments, the polypeptide comprises amino acids 190 to 925 of SEQ ID NO: 1. In some embodiments, the polypeptide is a fusion protein comprising a soluble ENPP1 polypeptide domain and one or more heterologous protein portions. In some embodiments, the heterologous protein portion increases the circulating half-life of the soluble ENPP1 polypeptide in a mammal as compared to the corresponding wild-type soluble ENPP1 polypeptide. In some embodiments, the heterologous protein portion comprises an Fc domain. In some embodiments, the Fc domain comprises an amino acid sequence that is at least 75%, 80%, 85%, 90%, 91%, 92%, 93%, 94%, 95%, %%, 97%, 98%, 99%, or more identical to the amino acid sequence of SEQ ID NO: 13. In some embodiments, the Fc domain comprises the M252Y, S254T, and T256E amino acid substitutions, wherein the amino acid residues are numbered according to the EU index as in Kabat. In some embodiments, the Fc domain comprises at least one amino acid substitution selected from the group consisting of: M252Y, S254T, T256E, N434S, M428L, V259I, T250I, and V308F, wherein the amino acid residues are numbered according to the EU index as in Kabat. In some embodiments, the Fc domain has a higher affinity for FcRn than a wild-type IgG constant domain. In some embodiments, the polypeptide is an ENPP1-Fc fusion protein. In some embodiments, the ENPP1-Fc fusion protein comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 10. In some embodiments, the ENPP1-Fc fusion protein comprises an amino acid sequence that is at least 70%, 75%, 80%, 85%, 86%, 87%, 88%, 89%, 90%, 91%, 92%, 93%, 94%, 95%, %%, 97%, 98%, 99%, or 100% identical to SEQ ID NO: 11. In some embodiments, the ENPP1-Fc fusion protein comprises an amino acid sequence that is at least 70%, 75%, 80%, 85%, 86%, 87%, 88%, 89%, 90%, 91%, 92%, 93%, 94%, 95%, %%, 97%, 98%, 99%, or 100% identical to SEQ ID NO: 12. In some embodiments, the ENPP1-Fc fusion protein comprises an amino acid sequence that is at least 70%, 75%, 80%, 85%, 86%, 87%, 88%, 89%, 90%, 91%, 92%, 93%, 94%, 95%, %%, 97%, 98%, 99%, or 100% identical to SEQ ID NO: 121. In some embodiments, the ENPP1-Fc fusion protein comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 122. In some embodiments, the ENPP1-Fc fusion protein comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 127. In some embodiments, the ENPP1-Fc fusion protein comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 128. In some embodiments, the soluble ENPP1 polypeptide comprises an N-terminal leader sequence (e.g., MTRLTVLALLAGL-LASSRA) (SEQ ID NO. 129). In some embodiments, the soluble ENPP1 polypeptide further comprises an N-terminal extension of one or more amino acids at the N-terminus of the ENPP1 polypeptide. In some embodiments, the N-terminal extension is S or KS. In some embodiments, the soluble ENPP1 polypeptide further comprises a heterologous moiety. In some embodiments, the heterologous moiety is selected from the group consisting of a glycosylated amino acid, a PEGylated amino acid, a farnesylated amino acid, an acetylated amino acid, a biotinylated amino acid, and a lipid moiety. In some embodiments, amino acid residue 332 with respect to SEQ ID NO: 1 comprises an I332T substitution.

In some aspects, the disclosure provides soluble ENPP3 polypeptides. In some aspects, the disclosure provides a soluble ENPP3 polypeptide that lacks both SMB domain 1 and SMB domain 2 of ENPP3. In some aspects, the disclosure provides a soluble ENPP3 polypeptide that lacks both SMB domain 1 and SMB domain 2 of ENPP3, wherein the soluble ENPP3 polypeptide lacks a negatively charged bone targeting domain. In some aspects, the disclosure provides a soluble ENPP3 polypeptide that is at least 90% identical to amino acids 136 to 875 of SEQ ID NO: 116, wherein the polypeptide lacks both SMB domain 1 and SMB domain 2 of ENPP3. In some embodiments, the polypeptide has reduced ability to homodimerize as compared to the corresponding wild-type soluble ENPP3 polypeptide. In some embodiments, the polypeptide comprises one or more amino acid modifications that reduce homodimerization of the ENPP3 polypeptide as compared to the corresponding wild-type soluble ENPP3 polypeptide. In some embodiments, the one or more amino acid modifications reduce homodimerization by at least 1%, 2%, 3%, 4%, 5%, 6%, 7%, 8%, 9%, 10%, 15%, 20%, 30%, 40%, 50%, 60%, 70%, 80%, 90% or 100%. In some embodiments, the polypeptide has reduced affinity for the human insulin receptor (IR) as compared to the corresponding wild-type soluble ENPP3 polypeptide. In some embodiments, the ENPP3 polypeptide comprises the phosphodiesterase catalytic domain of ENPP3. In some embodiments, the ENPP3 polypeptide lacks one or both of SMB domains 1 and 2. In some embodiments, the polypeptide is at least 90% identical to amino acids 136-875 of SEQ ID NO: 116. In some embodiments, the polypeptide is at least 95% identical to amino acids 136-875 of SEQ ID NO: 116. In some embodiments, the polypeptide is at least 99% identical to amino acids 136-875 of SEQ ID NO: 116. In some embodiments, the polypeptide comprises amino acids 136-875 of SEQ ID NO: 116. In some embodiments, the polypeptide is a fusion protein comprising a soluble ENPP3 polypeptide domain and one or more heterologous protein portions. In some embodiments, the heterologous protein portion increases the circulating half-life of the soluble ENPP3 polypeptide in a mammal as compared to the corresponding wild-type soluble ENPP3 polypeptide. In some embodiments, the heterologous protein portion comprises an Fc domain. In some embodiments, the Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 13. In some embodiments, the Fc domain comprises the M252Y, S254T, and T256E amino acid substitutions, wherein the amino acid residues are numbered according to the EU index as in Kabat. In some embodiments, the Fc domain comprises at least one amino acid substitution selected from the group consisting of: M252Y, S254T, T256E, N434S, M428L, V2591, T2501, and V308F, wherein the amino acid residues are numbered according to the EU index as in Kabat. In some embodiments, the Fc domain has a higher affinity for FcRn than a wild-type IgG constant domain. In some embodiments, the polypeptide is an ENPP3-Fc fusion protein. In some embodiments, the soluble ENPP3 polypeptide further comprises a heterologous moiety. In some embodiments, the heterologous moiety is selected from the group consisting of a glycosylated amino acid, a PEGylated amino acid, a farnesylated amino acid, an acetylated amino acid, a biotinylated amino acid, and a lipid moiety.

In some aspects, the disclosure provides an ENPP1 fusion protein. In some aspects, the disclosure provides an ENPP3 fusion protein. In some aspects, the disclosure provides a fusion protein comprising: (a) a soluble ENPP1 polypeptide portion which lacks both a SMB domain 1 and SMB domain 2, wherein the soluble ENPP1 polypeptide lacks a negatively-charged bone-targeting domain and (b) a heterologous protein portion. In some aspects, the disclosure provides a fusion protein comprising: (a) a soluble ENPP3 polypeptide portion which lacks both a SMB domain 1 and SMB domain 2 and (b) a heterologous protein portion. In some aspects, the disclosure provides a fusion protein comprising: (a) a soluble ENPP1 polypeptide portion which comprises an amino acid substitution at at least one of position 816, 817, or 818 relative to SEQ ID NO: 1, wherein the ENPP1 polypeptide demonstrates greater proteolytic resistance to a protease than the corresponding wild-type soluble ENPP1 polypeptide and (b) heterologous protein portion. In some embodiments, the fusion protein comprises an amino acid sequence that is at least 90% identical to SEQ ID NO: 9. In some embodiments, the fusion protein comprises an amino acid sequence that is at least 90% identical to SEQ ID NO: 11. In some embodiments, the soluble ENPP1 polypeptide portion comprises an amino acid sequence that is at least 90% identical to amino acids 190 to 925 of SEQ ID NO: 1. In some embodiments, the soluble ENPP1 polypeptide portion comprises an amino acid sequence that is at least 95% identical to amino acids 190 to 925 of SEQ ID NO: 1. In some embodiments, the soluble ENPP1 polypeptide portion comprises an amino acid sequence that is at least 99% identical to amino acids 190 to 925 of SEQ ID NO: 1. In some embodiments, the soluble ENPP1 polypeptide portion comprises amino acids 190 to 925 of SEQ ID NO: 1. In some embodiments, the soluble ENPP3 polypeptide portion comprises an amino acid sequence that is at least 90% identical to amino acids 136 to 875 of SEQ ID NO: 116. In some embodiments, the soluble ENPP3 polypeptide portion comprises an amino acid sequence that is at least 95% identical to amino acids 136 to 875 of SEQ ID NO: 116. In some embodiments, the soluble ENPP3 polypeptide portion comprises an amino acid sequence that is at least 99% identical to amino acids 136 to 875 of SEQ ID NO: 116. In some embodiments, the soluble ENPP3 polypeptide portion comprises amino acids 136 to 875 of SEQ ID NO: 116. In some embodiments, the heterologous protein portion increases the circulating half-life of the soluble ENPP1 polypeptide in a mammal as compared to the corresponding wild-type soluble ENPP1 polypeptide. In some embodiments, the heterologous protein portion increases the circulating half-life of the soluble ENPP3 polypeptide in a mammal as compared to the corresponding wild-type soluble ENPP3 polypeptide. In some embodiments, the heterologous protein portion comprises an Fc domain. In some embodiments, the Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 13. In some aspects, the disclosure provides a conjugate comprising an ENPP1 polypeptide, an ENPP3 polypeptide, or a fusion protein. In some aspects, the disclosure provides a conjugate comprising: (a) the soluble ENPP1 polypeptide as used herein, the soluble ENPP3 polypeptide as used herein, or the ENPP1 or ENPP3 fusion protein as used herein; and (b) a heterologous moiety. In some embodiments, the heterologous moiety is selected from the group consisting of a glycosylated amino acid, a PEGylated amino acid, a farnesylated amino acid, an acetylated amino acid, a biotinylated amino acid, and a lipid moiety. In some aspects, the disclosure provides a pharmaceutical composition comprising: (a) the soluble ENPP1 polypeptide as used herein, the soluble ENPP3 polypeptide as used herein, the ENPP1 or ENPP3 fusion protein as used herein, or the conjugate as used herein, and (b) a pharmaceutically acceptable carrier.

In some aspects, the disclosure provides a method for reducing and/or ameliorating ectopic calcification in a subject. In some embodiments the disclosure provides a method for reducing and/or ameliorating ectopic calcification in a subject, comprising administering to the subject a therapeutically effective amount of the soluble ENPP1 polypeptide as used herein, the soluble ENPP3 polypeptide as used herein, the ENPP1 or ENPP3 fusion protein as used herein, the conjugate as used herein, or the pharmaceutical composition as used herein, thereby reducing and/or ameliorating ectopic calcification in the subject. In some embodiments, the ectopic calcification is selected from the group consisting of soft tissue calcification, arterial calcification, and vascular calcification. In some embodiments, the subject has a disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, autosomal recessive hypophosphatemic rickets type 2 (ARHR2), osteoarthritis, aging related hardening of arteries, idiopathic infantile arterial calcification (IIAC), Generalized Arterial Calcification of Infancy (GACI), and calcification of atherosclerotic plaques. In some embodiments, the soft tissue is selected from the group consisting of atherosclerotic plaques, muscular arteries, joint, spine, articular cartilage, vertebral disk cartilage, vessels, and connective tissue. In some embodiments, the subject is ENPP1 deficient. In some embodiments, the subject is ENPP3 deficient. In some embodiments, the subject has pseudoxanthoma elasticum (PXE). In some embodiments, the subject has a pathogenic mutation in ABCC6 gene. In some aspects, the disclosure provides a method for treating a subject having ENPP1 deficiency disorder, the method comprising: administering to the subject a therapeutically effective amount of the soluble ENPP1 polypeptide as used herein, the soluble ENPP3 polypeptide as used herein, the fusion protein as used herein, the conjugate as used herein, or the pharmaceutical composition as used herein, to thereby treat the subject. In some aspects, the disclosure provides a method for treating a subject having ENPP3 deficiency disorder, the method comprising: administering to the subject a therapeutically effective amount of the soluble ENPP1 polypeptide as used herein, the soluble ENPP3 polypeptide as used herein, the fusion protein as used herein, the conjugate as used herein, or the pharmaceutical composition as used herein, to thereby treat the subject. In some embodiments, the subject has a disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, autosomal recessive hypophosphatemic rickets type 2 (ARHR2), osteoarthritis, aging related hardening of arteries, idiopathic infantile arterial calcification (IIAC), Generalized Arterial Calcification of Infancy (GACI), and calcification of atherosclerotic plaques. In some embodiments, the subject has ectopic calcification. In some embodiments, the ectopic calcification is selected from the group consisting of soft tissue calcification, arterial calcification, and vascular calcification. In some embodiments, the subject has pathological ossification.

In some aspects, the disclosure provides an isolated polynucleotide comprising a coding sequence for the soluble ENPP1 polypeptide as used herein. In certain embodiments, the isolated polynucleotide comprises a sequence of any one of SEQ ID NOs: 14 or 15. In some aspects, the disclosure provides an isolated polynucleotide comprising a coding sequence for the soluble ENPP3 polypeptide as used herein. In some aspects, the disclosure provides a recombinant polynucleotide comprising a promoter sequence operably linked to the polynucleotide. In some aspects, the disclosure provides a cell transformed with the recombinant polynucleotide. In some embodiments, the cell is a mammalian cell. In some embodiments, the cell is a CHO cell or a human cell. In some aspects, the disclosure provides a method of making a soluble ENPP1 polypeptide, comprising: a) culturing a cell transformed with a recombinant polynucleotide under conditions suitable for expression of the soluble ENPP1 polypeptide; and b) recovering the soluble ENPP1 polypeptide so expressed. In some embodiments, the method further comprises formulating the soluble ENPP1 polypeptide with a pharmaceutically acceptable carrier, diluent, and/or excipient to produce a pharmaceutical composition. In some aspects, the disclosure provides a method of making a soluble ENPP3 polypeptide, comprising: a) culturing a cell transformed with a recombinant polynucleotide under conditions suitable for expression of the soluble ENPP3 polypeptide; and b) recovering the soluble ENPP3 polypeptide so expressed. In some embodiments, the method further comprises formulating the soluble ENPP3 polypeptide with a pharmaceutically acceptable carrier, diluent, and/or excipient to produce a pharmaceutical composition.

BRIEF DESCRIPTION OF THE DRAWINGS

FIG. 1 shows the full, unprocessed amino acid sequence of wild-type ENPP1 precursor protein (SEQ ID NO: 1). The cytosolic and transmembrane regions are underlined. Potential N-glycosylation sites are in bold. PSCAKE (residues 99-104; boxed) is the start of soluble ENPP1 protein portion which includes SMB1 (residues 104-144) and SMB2 (residues 145-189).

FIG. 2 illustrates certain domains of human ENPP1.

FIG. 3 shows the amino acid sequence of a soluble wild-type ENPP1 polypeptide (SEQ ID NO: 2).

FIG. 4 shows the amino acid sequence of a soluble wild-type ENPP1 polypeptide lacking both SMB1 and SMB2 (SEQ ID NO: 3).

FIG. 5A and FIG. 5B show a multiple sequence alignment of various vertebrate soluble ENPP1 polypeptides and human soluble ENPP1 polypeptide (SEQ ID NOs: 4-8). The various soluble ENPP1 polypeptides correspond to the following species and represent regions of the specific NCBI accession number: Mouse (NCBI accession NP_001295256.1; SEQ ID NO:4), Cow (NCBI accession NP_001193141; SEQ ID NO: 5), Rabbit (NCBI 1I accession NP_001162404.1; SEQ ID NO:6). Human (NCBI accession NP_006199.2; SEQ ID NO: 7), and Baboon (NCBI accession NP_001076211.2; SEQ ID NO: 8).

FIG. 6 shows the full, unprocessed amino acid sequence of wild-type ENPP3 precursor protein (SEQ ID NO: 116).

The cytosolic and transmembrane regions are underlined. The soluble ENPP3 protein portion includes SMB1 and SMB2.

FIG. 7 illustrates certain domains of human ENPP3.

Figure 8:
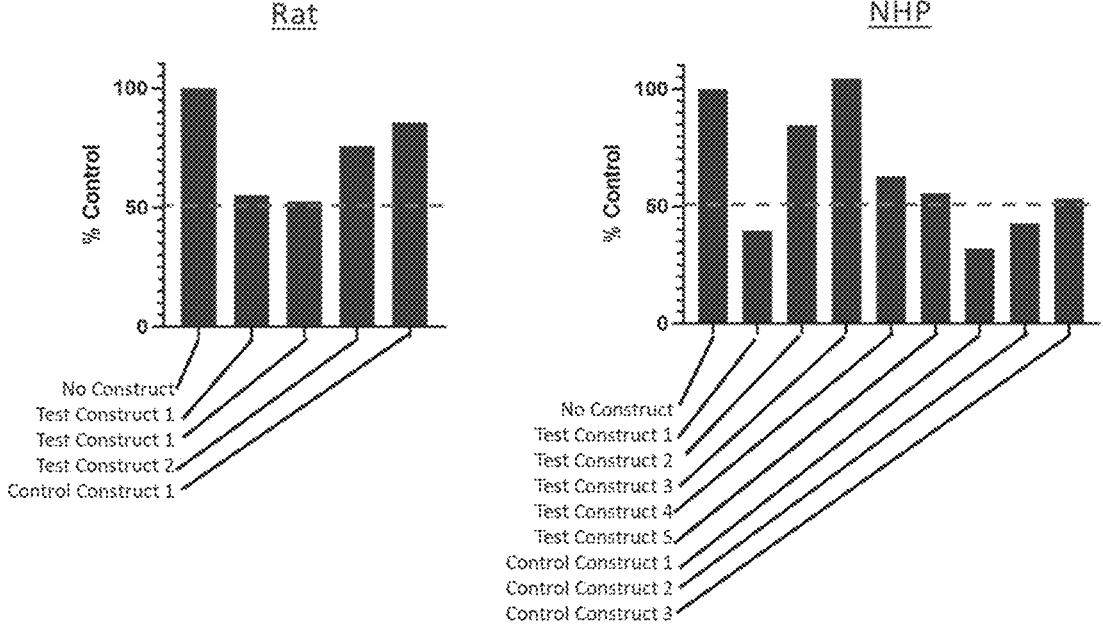

FIG. 8 is a bar graph illustrating the results of an anti-drug antibody (ADA) ELISA competition assay performed on rat and non-human primate (NHP) samples. Serum and plasma samples containing ADAs generated during animal studies were added to an ENPP1-Fc-treated assay plate and treated with competitors. Changes in the ELISA signals were measured, and are shown as a percentage relative to the control signal. Competitors used in the assay include: (a) Construct 1: an ENPP1-Fc construct containing the entire extracellular domain of human ENPP1. (b) Construct 2: an ENPP1-Fc construct comprising a variant form of the extracellular domain of human ENPP1 that lacks the SMB1 and SMB2 domains of ENPP1, (c) Construct 3: an ENPP1-Fc construct comprising a soluble human ENPP1 in which the catalytic domain was substituted with the catalytic domain from the corresponding domain of Cynomolgus monkey ENPP1. (d) Construct 4: an ENPP1-Fc construct comprising a soluble human ENPP1 in which the nuclease-like domain was substituted with the corresponding domain of the cynomolgus monkey ENPP1, (e) Construct 5: an ENPP1-Fc construct in which the soluble ENPP1 portion of the construct is linked to the Fc portion of the construct via the following amino acid linker sequence: GGGGS (SEQ ID NO:63), (f) Control Construct 1 comprising just human IgG1, (g) Control Construct 2: an ENPP1-Fc construct of Construct 1 that has been treated with PNGase F(deglycosylated ENPP1-Fc), and (h) Control Construct 3: a mock treated version of Control Construct 2. A dashed line is shown representing 50% of the ELISA signal relative to the control sample.

Figure 9A:
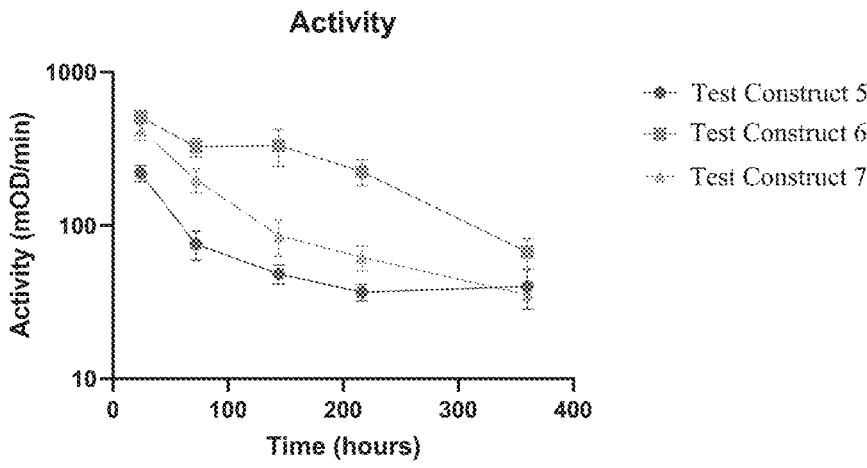
Figure 9B:
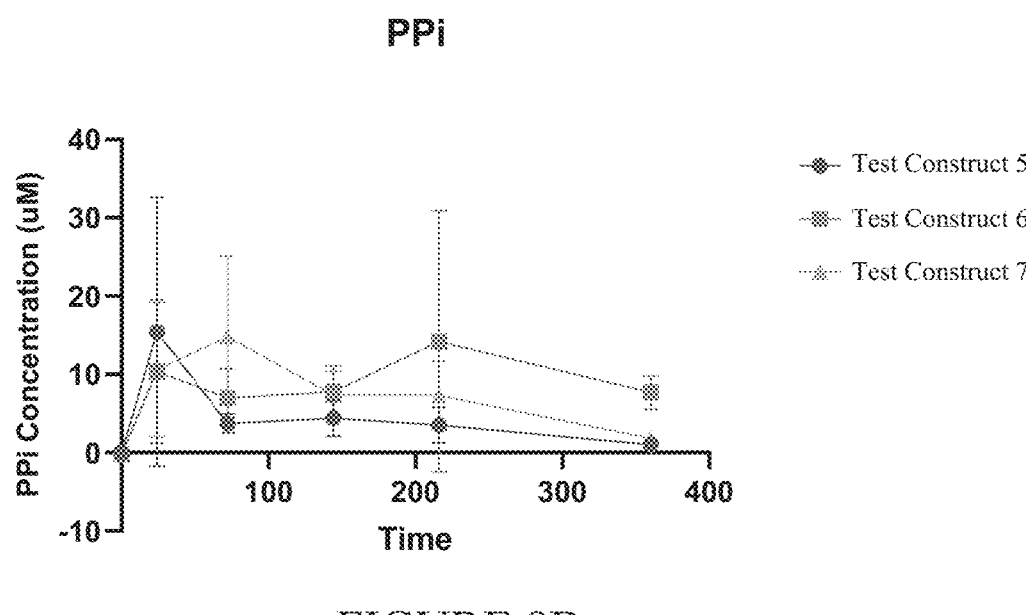

FIG. 9A and FIG. 9B are bar graphs illustrating the activity of various ENPP1-Fc constructs and associated PPi levels in vivo. FIG. 9A shows activity levels of Test Construct 5, Test Construct 6, and Test Construct 7 in vivo over 360 days. FIG. 9B shows PPi levels in mice treated with Test Construct 5, Test Construct 6, or Test Construct 7 over the test period. Test Construct 5 comprises an ENPP1-Fc construct in which the soluble ENPP1 portion of the construct is linked to the Fc portion of the construct via the following amino acid linker sequence: GGGGS (SEQ ID NO:63) (SEQ ID NO: 119). Test Construct 6 comprises an ENPP1-Fc construct comprising a variant form of the extracellular domain of human ENPP1 in which the catalytic domain of the ENPP1 portion comprises an 1332T substitution and the Fc domain comprises a triple mutation (M252Y, S254T, T256E) (SEQ ID NO: 120). Test Construct 7 comprises an ENPP1-Fc construct comprising a variant form of the extracellular domain of human ENPP1 that lacks the SMB1 and SMB2 domains, and in which the catalytic domain of the ENPP1 portion comprises a 1332T substitution and the Fc domain comprises a triple mutation (M252Y, S254T, T256E) (SEQ ID NO: 121).

Figure 10A:
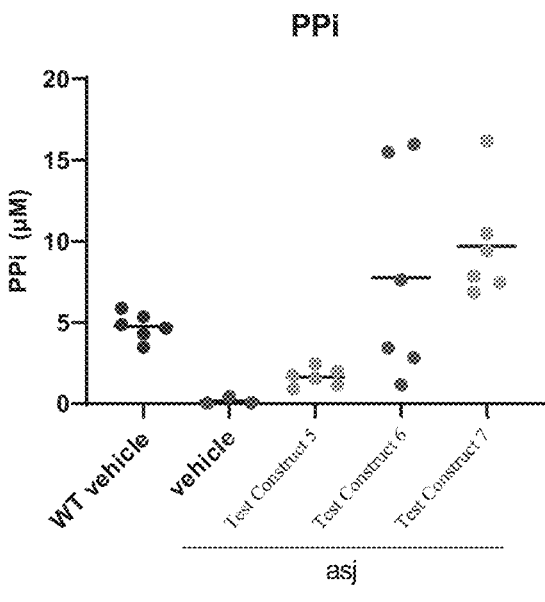

FIG. 10A-D show graphs of PPi levels and tissue calcification of the heart, aorta, kidney, and spleen in mice treated with vehicle or various ENPP1-Fc constructs (Test Construct 5, Test Construct 6, or Test Construct 7). FIG. 10A shows PPi levels in mice treated with either vehicle or Test Construct 5, Test Construct 6, or Test Construct 7. Mice were treated with either vehicle or Test Construct 5, Test Construct 6, or Test Construct 7, and tissue calcification of heart and aorta (FIG. 10B), kidney (FIG. 10C), and spleen (FIG. 10D) were measured. Test Construct 5 comprises an ENPP1-Fc construct in which the soluble ENPP1 portion of the construct is linked to the Fc portion of the construct via the following amino acid linker sequence: GGGGS (SEQ ID NO:63). (SEQ ID NO: 119). Test Construct 6 comprises an ENPP1-Fc construct comprising a variant form of the extracellular domain of human ENPP1 in which the catalytic domain of the ENPP1 portion comprises an I332T substitution and the Fc domain comprises a triple mutation (M252Y, S254T, T256E). (SEQ ID NO: 120). Test Construct 7 comprises an ENPP1-Fc construct comprising a variant form of the extracellular domain of human ENPP1 that lacks the SMB1 and SMB2 domains, and in which the catalytic domain of the ENPP1 portion comprises a I332T substitution and the Fc domain comprises a triple mutation (M252Y, S254T, T256E). (SEQ ID NO: 121).

Figure 11:
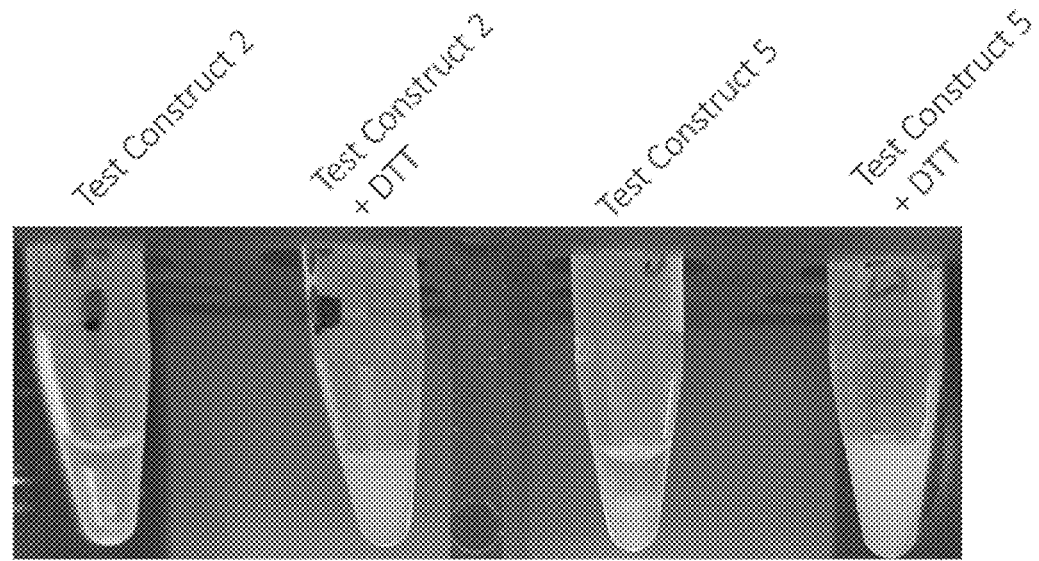

FIG. 11 shows aggregation of ENPP1-Fc polypeptides comprising SMB domains (Test Construct 5) or lacking SMB domains (Test Construct 2). Each sample was incubated at ambient room temperature with or without 100 mM DTT for either 15 days (Test Construct 2) or 13 days (Test Construct 5). Test Construct 2 sample, which lacks SMB domains, remained clear out to 15 days.

DETAILED DESCRIPTION

1. Overview

The application provides compositions comprising ENPP1 polypeptides or ENPP3 polypeptides and their uses in treating diseases or disorders associated with ENPP1 or ENPP3. In certain aspects, the disclosure relates to soluble ENPP1 polypeptides and uses thereof (e.g., of treating, preventing, and/or reducing the progression rate and/or severity of pathologic calcification and/or ossification or one or more complications of pathologic calcification and/or ossification). In certain aspects, the disclosure relates to soluble ENPP3 polypeptides and uses thereof (e.g., of treating, preventing, and/or reducing the progression rate and/or severity of pathologic calcification and/or ossification or one or more complications of pathologic calcification and/or ossification). Accordingly, the disclosure identifies functionally active portions and variants of ENPP1 or ENPP3. It is known in the art that certain mutations in the ENPP1 gene have been associated with generalized arterial calcification of infants (GACI), idiopathic infantile arterial calcification (IIAC), insulin resistance, hypophosphatemic rickets, and ossification of the posterior longitudinal ligament of the spine.

IIAC, a rare autosomal recessive and nearly always fatal disorder, is characterized by calcification of the internal elastic lamina of muscular arteries and stenosis due to myointimal proliferation. The symptoms of the disease most often appear by early infancy, and the disease is lethal by 6 months of age, generally because of ischemic cardiomyopathy and other complications of obstructive arteriopathy including renal artery stenosis. In more than a dozen reported cases of IIAC, periarticular calcifications of large joints also developed in infancy. Mutations in ENPP1 have been shown to be associated with the lowering of nucleotide pyrophosphatase/phosphodiesterase activity in certain IIAC patients. See, e.g., Rutsch et al. (2003). Nature Genetics 34:379-81.

ENPP1 polypeptides have been shown to be effective in treating certain diseases of ectopic tissue calcification. ENPP1-Fc has been shown to reduce generalized arterial calcifications in a mouse model for GACI (generalized arterial calcification of infants), which is a severe disease occurring in infants and involving extensive arterial calcification (Albright, et al., 2015, Nature Comm, 10006).

Fusion proteins of ENPP1 have also been described to treat diseases of severe tissue calcification (see, e.g., PCT Application Publication Nos. WO 2014/126%5 and WO 2016/187408), and a fusion protein of ENPP1 comprising a negatively-charged bone-targeting domain has been described to treat GACI (PCT Application Publication Nos. WO 2011/113027 and WO 2012/125182).

In certain aspects, the present disclosure contemplates using ENPP1 or ENPP3 polypeptides, and variants thereof, in treating, ameliorating, and/or preventing diseases or conditions that are associated with abnormal activity of an ENPP1 or ENPP3 polypeptide. ENPP1 and ENPP3 polypeptides are involved in the regulation of many critical biological processes (e.g., regulation of cardiovascular, neurological, immunological, musculoskeletal, hormonal, and hematological functions). Due to their key functions in these processes, they may be desirable targets for therapeutic intervention. For example, ENPP1 or ENPP3 polypeptides (e.g., soluble ENPP1 or ENPP3 polypeptides) may be used to treat, ameliorate, and/or prevent human or animal disorders or conditions. Example of such disorders or conditions include, but are not limited to, ectopic calcification (e.g., soft tissue calcification, arterial calcification, and vascular calcification), chronic kidney disease (CKD), end stage renal disease (ESRD), calcific uremic arteriolopathy (CUA), calciphylaxis, ossification of the posterior longitudinal ligament (OPLL), hypophosphatemic rickets, autosomal recessive hypophosphatemic rickets type 2 (ARHR2), osteoarthritis, aging related hardening of arteries, idiopathic infantile arterial calcification (IIAC), Generalized Arterial Calcification of Infancy (GACI), and calcification of atherosclerotic plaques. Other examples include ENPP1 deficiencies (e.g., GACI and ARHR2), pseudoxanthoma elasticum (PXE), disorders wherein the subject has a pathogenic mutation in ABCC6 gene, and pathological ossification. ENPP1 polypeptides and these disorders and conditions are discussed in greater detail below.

2. Soluble ENPP Polypeptides

In certain aspects, the present disclosure relates to soluble ENPP1 or ENPP3 polypeptides. ENPP1 and ENPP3 polypeptides disclosed herein include naturally occurring polypeptides of the ENPP1 and ENPP3 family as well as any variants thereof (including mutants, fragments, fusions, and/or peptidomimetic forms) that retain a biological activity. The terms "ENPP1" or "ENPP1 polypeptide" refers to ectonucleotide pyrophosphatase/phosphodiesterase 1 proteins (NPP1/ENPP1/PC-1) and ENPP1-related proteins, derived from any species. The terms "ENPP3" or "ENPP3 polypeptide" refers to ectonucleotide pyrophosphatase/phosphodiesterase 3 proteins (NPP3/ENPP3/PDNP3) and ENPP3-related proteins, derived from any species. ENPP1 protein comprises a type II transmembrane glycoprotein that forms a homodimer. Each monomer of the ENPP1 protein comprises a short intracellular N-terminal domain involved in targeting to the plasma membrane, a transmembrane domain, and a large extracellular region comprising several domains. The large extracellular region comprises SMB1 and SMB2 domains, which have been reported to take part in ENPP1 dimerization (R. Gijsbers, H. et al., Biochem. J. 371; 2003: 321-330). Specifically, the SMB domains contain eight cysteine residues, each arranged in four disulfide bonds, and have been shown to mediate ENPP1 homodimerization through covalent cystine inter- and intramolecular bonds. The protein cleaves a variety of substrates, including phosphodiester bonds of nucleotides and nucleotide sugars and pyrophosphate bonds of nucleotides and nucleotide sugars. ENPP1 protein functions to hydrolyze nucleoside 5' triphosphatase to either corresponding monophosphates and also hydrolyzes diadenosine polyphosphates. ENPP1 proteins play a role in purinergic signaling which is involved in the regulation of cardiovascular, neurological, immunological, musculoskeletal, hormonal, and hematological functions. An exemplary amino acid sequence of the human ENPP1 precursor protein (NCBI accession NP_006199) is shown in FIG. 1 (SEQ ID NO: 1). The human ENPP1 precursor protein includes an endogenous ENPP1 signal peptide sequence at the ENPP1 N-terminus. Numbering of amino acids for all ENPP1-related polypeptides described herein is based on the numbering of the human ENPP1 precursor protein sequence provided in FIG. 1 unless specifically designated otherwise. In certain embodiments, the ENPP1 precursor protein further comprises an endogenous or heterologous signal peptide sequence. Upon proteolysis, the signal peptide sequence is cleaved from the ENPP1 precursor protein to provide the mature ENPP1 protein. See, e.g., Jansen S. et al. J Cell Sci. 2005; 118 (Pt 14):3081-9. Exemplary signal peptide sequences that can be used with the polypeptides disclosed herein include, but are not limited to, ENPP1 signal peptide sequence, ENPP2 signal peptide sequence, ENPP7 signal peptide sequence, and/or ENPP5 signal peptide sequence. The processed (mature) extracellular ENPP1 polypeptide sequence is shown in FIG. 3 (SEQ ID NO: 2).

It is generally known in the art that ENPP1 is well-conserved among vertebrates, with large stretches of the extracellular domain substantially conserved. For example, FIG. 5A and FIG. 5B depict a multi-sequence alignment of a human ENPP1 extracellular domain compared to various ENPP1 orthologs. ENPP1 binding to various nucleotide triphosphates (e.g., ATP, UTP, GTP, TTP, and CTP), pNP-TMP. 3',5'-cAMP, and 2'-3'-cGAMP is also highly conserved (see, e.g., Kato K. et al., Proc Nall Acad Sci USA. 2012; 109(42):16876-81 and Mackenzie N C, et al. Bone. 2012; 51(5):961-8). Accordingly, from these alignments, it is possible to predict key amino acid positions with the extracellular domain that are important for normal ENPP1 activities as well as to predict amino acid positions that are likely to be tolerant to substitution without significantly altering normal ENPP1 activities. Therefore, an active human ENPP1 polypeptide useful in accordance with the presently disclosed methods may include one or more amino acids at corresponding positions from the sequence of another vertebrate ENPP1, or may include a residue that is similar to that in the human or other vertebrate sequences. Substitutions of one or more amino acids at corresponding positions may include conservative variations or substitutions that are not likely to change the shape of the polypeptide chain or alter normal ENPP1 activities. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine, and so forth. For example, ENPP1 polypeptides include polypeptides derived from the sequence of any known ENPP1 polypeptide having a sequence at least about 80% identical to the sequence of an ENPP1 polypeptide, and preferably at least 85%, 90%, 91%, 92%, 93%, 94%, 95%, 96%, 97%, 98%, 99% or greater identity. In some embodiments, a soluble ENPP1 polypeptide may comprise a ENPP1 polypeptide domain (e.g., SMB1, SMB2, catalytic domain, nuclease-like domain, linker sequence) or subsequence which has been substituted with the corresponding domain or subsequence from another species (e.g., human to cynomolgus).

ENPP1 proteins have been characterized in the art in terms of structural and biological characteristics. In certain embodiments, soluble ENPP1 proteins disclosed herein comprise pyrophosphatase and/or phosphodiesterase activity. For instance, in some embodiments, the ENPP1 protein binds nucleotide triphosphates (e.g., ATP, UTP. GTP, TTP, and CTP), pNP-TMP, 3',5'-cAMP, and 2'-3'-cGAMP; and converts nucleotide triphosphates into inorganic pyrophosphate [see, e.g., Kato K. el al., Proc Natl Acad Sci USA. 2012; 109(42):16876-81; Li L. el al. Nat Chem Biol. 2014: 10(12):1043-8; Jansen S, et al. Structure. 2012:20(11):1948-59; and Onyedibe K I, et al. Molecules. 2019; 24(22)]. As used herein, the terms "enzymatically active" or "biologically active" refer to ENPP1 polypeptides that exhibit pyrophosphatase and/or phosphodiesterase activity (e.g., is capable of binding and/or hydrolyzing ATP into AMP and PPi and/or AP3a into ATP). For example, the pyrophosphatase/phosphodiesterase domain of an ENPP1 protein hydrolyzes extracellular nucleotide triphosphates to produce inorganic pyrophosphates (PPi) and is generally soluble. This activity can be measured using a pNP-TMP assay as previously described (Saunders, el al., 2008, Mol. Cancer Ther. 7(10):3352-62; Albright, et al., 2015, Nat Comm. 6:10006). In certain embodiments, the soluble ENPP1 polypeptide has a kew value for the substrate ATP greater than or equal to about 3.4 ($\pm$0.4) s$^{-1}$ enzyme$^{-1}$, wherein the k$_{cat}$ is determined by measuring the rate of hydrolysis of ATP for the polypeptide. In certain embodiments, the soluble ENPP1 polypeptide has a K$_M$ value for the substrate ATP less than or equal to about 2 pM, wherein the K$_M$ is determined by measuring the rate of hydrolysis of ATP for the polypeptide. In addition to the teachings herein, these references provide ample guidance for how to generate soluble ENPP1 proteins that retain one or more biological activities (e.g., conversion of nucleotides into inorganic pyrophosphate).

In one embodiment, the disclosure relates to soluble ENPP1 polypeptides. As described herein, the term soluble ENPP1 polypeptide includes any naturally occurring extracellular domain of an ENPP1 protein as well as any variants thereof (including mutants, fragments and/or peptidomimetic forms) that retain a biological activity (e.g., enzymatically active). An exemplary soluble ENPP1 polypeptide comprises an extracellular domain of an ENPP1 protein (e.g., residues 96 to 925 of NCBI accession NP_006199 or residues 190 to 925 of NCBI accession NP_006199) and is described herein. Examples of soluble ENPP1 polypeptides include, for example, an ENPP1 extracellular domain (SEQ ID NO: 2) as shown in FIG. 3: an ENPP1 extracellular domain lacking at least one of the SMB1 or SMB2 domains; an ENPP1 extracellular domain lacking both the SMB1 and SMB2 domains (e.g., as shown in SEQ ID NO: 3). The truncated ENPP1 extracellular domain shown in SEQ ID NO: 3 denotes ENPP1(190-925) based on the numbering in SEQ ID NO: 1. Exemplary soluble ENPP1 polypeptides comprise a catalytic domain and a nuclease like domain. In certain embodiments, the soluble ENPP1 polypeptides further comprise a signal sequence in addition to the extracellular domain of an ENPP1 polypeptide. Exemplary signal sequences include the native signal sequence of an ENPP1 polypeptide, or a signal sequence from another protein, such as but not limited to a hENPP7 signal sequence. Examples of variant soluble ENPP1 polypeptides are provided throughout the present disclosure as well as in International Patent Application Publication Nos. WO 2012/125182, WO 2014/126965, WO 2016/187408, WO 2018/027024, WO 2020/206302, and WO 2020/047520, all of which are incorporated herein by reference in their entireties.

A person of skill in the art would recognize that the residues corresponding to various domains of an ENPP1 polypeptide may vary. Specifically, the identification of polypeptide domains is classically based upon the protein sequence and/or structure. The polypeptide sequence and/or structure can be used to identify related polypeptide domains (i.e., the polypeptide may have sequence and/or structural resemblance to other protein structures or domains). In some embodiments, the SMB1 domain of ENPP1 comprises an amino acid sequence that begins at any one of amino acids 99, 100, 101, 102, 103, 104, 105, 106, 107, or 108 of SEQ ID NO: 1 and ends at any one of amino acids 140, 141, 142, 143, 144, or 145 of SEQ ID NO: 1. In some embodiments, the SMB1 domain of ENPP1 comprises an amino acid sequence that begins at an amino acid residue $\pm$5 residues upstream or downstream of amino acid residue 104 of SEQ ID NO: 1 and ends at an amino acid residue $\pm$3 residues upstream or downstream of amino acid residue 143 of SEQ ID NO: 1. In some embodiments, the SMB1 domain of ENPP1 comprises amino acid residues 100-142 of SEQ ID NO: 1. In some embodiments, the SMB1 domain of ENPP1 comprises amino acid residues 104-144 of SEQ ID NO: 1.

In some embodiments, the SMB2 domain of ENPP1 comprises an amino acid sequence that begins at any one of amino acids 141, 142, 143, 144, or 145 of SEQ ID NO: 1 and ends at any one of amino acids 186, 187, 188, 189, or 190 of SEQ ID NO: 1. In some embodiments, the SMB2 domain of ENPP1 comprises an amino acid sequence that begins at an amino acid residue $\pm$3 residues upstream or downstream of amino acid residue 143 of SEQ ID NO: 1 and ends at an amino acid residue $\pm$3 residues upstream or downstream of amino acid residue 188 of SEQ ID NO: 1. In some embodiments, the SMB2 domain of ENPP1 comprises amino acid residues 142-187 of SEQ ID NO: 1. In some embodiments, the SMB2 domain of ENPP1 comprises amino acid residues 145-189 of SEQ ID NO: 1.

In some embodiments, the first linker domain ("L1" as shown in FIG. 2) comprises an amino acid sequence that begins at any one of amino acids 185, 186, 187, 188, or 189 of SEQ ID NO: 1 and ends at any one of amino acids 206, 207, 208, 209, or 210 of SEQ ID NO: 1. In some embodiments, the first linker domain of ENPP1 comprises an amino acid sequence that begins at an amino acid residue $\pm$3 residues upstream or downstream of amino acid residue 187 of SEQ ID NO: 1 and ends at an amino acid residue 3 residues upstream or downstream of amino acid residue 208 of SEQ ID NO: 1. In some embodiments, the first linker domain of ENPP1 comprises amino acid residues 187-208 of SEQ ID NO: 1.

In some embodiments, the catalytic domain (phosphodiesterase domain) of ENPP1 comprises an amino acid sequence that begins at any one of amino acids 190, 191, 192, 193, 194, 195, 196, 197, 198, 199, 200, 201, 202, 203, 204, 205, 206, 207, 208, or 209 of SEQ ID NO: 1 and ends at any one of amino acids 590, 591, 592, 593, 594, 595, 596, 597, or 598 of SEQ ID NO: 1. In some embodiments, the catalytic domain of ENPP1 comprises an amino acid sequence that begins at an amino acid residue $\pm$11 residues upstream or downstream of amino acid residue 199 of SEQ ID NO: 1 and ends at an amino acid residue $\pm$5 residues upstream or downstream of amino acid residue 594 of SEQ ID NO: 1. In some embodiments, the catalytic domain comprises residues 208-597 of SEQ ID NO: 1. In some embodiments, the catalytic domain comprises residues 191-591 of SEQ ID NO. 1.

In some embodiments, the nuclease-like domain of ENPP1 comprises an amino acid sequence that begins at any one of amino acids 647, 648, 649, 650, 651, 652, 653, 654, or 655 of SEQ ID NO: 1 and ends at any one of amino acids 923, 924, or 925 of SEQ ID NO: 1. In some embodiments, the nuclease-like domain of ENPP1 comprises an amino acid sequence that begins at an amino acid residue ±5 residues upstream or downstream of amino acid residue 651 of SEQ ID NO: 1 and ends at an amino acid residue ±2 residues upstream or downstream of amino acid residue 923 of SEQ ID NO: 1. In some embodiments, the nuclease-like domain comprises residues 648-925 of SEQ ID NO: 1. In some embodiments, the nuclease-like domain comprises residues 654-925 of SEQ ID NO: 1.

In some embodiments, the present disclosure contemplates generating functional ENPP1 variants by modifying the structure of a soluble ENPP1 polypeptide for such purposes as, but not limited to, enhancing therapeutic efficacy or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the enzymatic activity of the variant polypeptide as compared to the wild-type polypeptide, the ability of the variant polypeptide to produce inorganic pyrophosphates (PPi) as compared to the wild-type polypeptide, or the ability of the variant polypeptide to bind to one or more of ATP, UTP, GTP, TfTP, CTP, pNP-TMP, 3',5'-cAMP, and 2'-3'-cGAMP as compared to the wild-type polypeptide.

In certain embodiments, the present disclosure contemplates introducing substitutions in one or more domains of a soluble ENPP1 polypeptide, such as, for example, one or more substitutions in the catalytic and/or nuclease domain. In some embodiments, the soluble ENPP1 polypeptide comprises one or more amino acid substitutions such as, for example, substitutions at a position of SEQ ID NO: 1 that is susceptible to cleavage by a protease during manufacturing and/or administration. Exemplary substitutions include, for example, substitutions at a position of SEQ ID NO: 1 including positions 816, 817, or 818 relative to SEQ ID NO: 1. In some embodiments, the soluble ENPP1 polypeptide demonstrates greater proteolytic resistance to a protease than the corresponding wild-type soluble ENPP1 polypeptide. Optionally, a soluble ENPP1 polypeptide with substitutions in the catalytic and/or nuclease domain demonstrates substantially similar biological activity as the corresponding wild-type ENPP1 polypeptides. For example, a soluble ENPP1 polypeptide of the disclosure may bind and hydrolyze ATP into AMP and PPi and/or AP3a into ATP similar to the corresponding wild-type soluble ENPP1 polypeptide. In some embodiments, the protease is trypsin. In some embodiments, the protease is a trypsin-like protease.

In certain embodiments, such substitutions increase the proteolytic resistance of the soluble ENPP1 polypeptide by 1%, 2%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, or 300% more than the wild-type ENPP1 polypeptide. In other embodiments, the substitution in the soluble ENPP1 polypeptide provides a homogenous composition with protein purity increased by about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, or 300% as compared to the wild-type ENPP1 polypeptide. For instance, cleavage of the soluble ENPP1 polypeptide by a protease may result in several polypeptides of varying lengths. A protease resistant soluble ENPP1 polypeptide may result in the production of a soluble ENPP1 polypeptide comprising a single species or an increase in the homogeneity of the soluble ENPP1 polypeptide that is produced. Additionally, the greater proteolytic resistance of the ENPP1 polypeptide can result in a decrease in protein cleavage by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, or 300%. The term "substitution" as used herein includes insertions, deletions, and/or modifications with reference to the wild-type ENPP1 polypeptide.

The disclosure provides a number of soluble ENPP1 polypeptides that have greater proteolytic resistance to a protease than a corresponding wild-type soluble ENPP1 polypeptide. Optionally, the soluble ENPP1 polypeptides have substantially similar biological activities as the corresponding wild-type ENPP1 polypeptides. For example, a soluble ENPP1 polypeptide of the disclosure may bind and hydrolyze ATP into AMP and PPi and/or AP3a into ATP similar to the corresponding wild-type ENPP1 polypeptide. Accordingly, soluble ENPP1 polypeptides may, for example, comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence comprising amino acids 190 to 925 of SEQ ID NO: 1, wherein the polypeptide comprises one or more amino acid substitutions at a position of SEQ ID NO. 1 selected from the group consisting of position 816, 817, or 818 relative to SEQ ID NO: 1. In some embodiments, the soluble ENPP1 polypeptide further lacks SMB1. For instance, a SMB1 domain of a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 100 to 141 of SEQ ID NO: 1. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 142 to 925 of SEQ ID NO: 1. In some embodiments, a soluble ENPP1 polypeptide further lacks SMB2. For instance, a SMB2 domain of a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 142 to 186 of SEQ ID NO: 1. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 107 to 144 of SEQ ID NO: 1 and residues 190 to 925 of SEQ ID NO: 1. In some embodiments, a soluble ENPP1 polypeptides may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 100 to 142 of SEQ ID NO: 1 and residues 187 to 925 of SEQ ID NO: 1. In some embodiments, a soluble ENPP1 polypeptide further lacks SMB2 and the first linker domain. In some embodiments, a soluble ENPP1 polypeptide further lacks SMB1 and SMB2. For instance, soluble ENPP1 polypeptides may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 188 to 925 of SEQ ID NO: 1. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 190 to 925 of SEQ ID NO: 1. In some embodiments, a soluble ENPP1 polypeptide lacks SMB1, SMB2, and the first linker domain. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 11. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95% 96%, 97%, 98%, 99%, or 100/identical to SEQ ID NO: 12. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 121. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 122. In some embodiments, the soluble ENPP1 polypeptide comprises an N-terminal leader sequence (e.g., MTRLTVLALLAGLLASSRA). In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 127. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 128. In some embodiments, the soluble ENPP1 polypeptide comprises one or more amino acid substitutions at a position of SEQ ID NO: 1 selected from the group consisting of position 816, 817, or 818 relative to SEQ ID NO: 1. In some embodiments, the ENPP1 polypeptide comprises one or more amino acid substitutions at a position of SEQ ID NO: 1 selected from the group consisting of position 816, 817, or 818 relative to SEQ ID NO: 1. In some embodiments, the soluble ENPP1 polypeptide comprises a substitution at at least position 816 relative to SEQ ID NO: 1. In some embodiments, the soluble ENPP1 polypeptide comprises an amino acid substitution for at least the lysine (K) at position 816. In some embodiments, the lysine (K) at position 816 is substituted with a histidine (H). In some embodiments, the lysine (K) at position 816 is substituted with an arginine (R). In some embodiments, the soluble ENPP1 polypeptide comprises an amino acid substitution for at least the arginine (R) at position 817. In some embodiments, the arginine (R) at position 817 is substituted with a histidine (H). In some embodiments, the arginine (R) at position 817 is substituted with a lysine (K). In some embodiments, the soluble ENPP1 polypeptide comprises an amino acid substitution for at least the arginine (R) at position 817. In some embodiments, the soluble ENPP1 polypeptide comprises a substitution at at least position 818 relative to SEQ ID NO: 1. In some embodiments, the soluble ENPP1 polypeptide comprises an amino acid substitution for at least the arginine (R) at position 818. In some embodiments, the arginine (R) at position 818 is substituted with a lysine (K). In some embodiments, the soluble ENPP1 polypeptide comprises an amino acid substitution for at least the arginine (R) at position 818.

In certain embodiments, the present disclosure contemplates introducing deletions in the extracellular domain of a soluble ENPP1 polypeptide such that the soluble ENPP1 polypeptide has decreased immunogenicity as compared to the corresponding wild-type soluble ENPP1 polypeptide. In some embodiments, the present disclosure contemplates introducing deletions in the extracellular domain of an ENPP1 polypeptide such that the soluble ENPP1 polypeptide has decreased protein aggregation as compared to the corresponding wild-type soluble ENPP1 polypeptide. For instance, the Somatomedin B domain 1 (SMB1) and SMB2 domains may be aggregation prone due to increased numbers of cysteine residues that are involved in disulfide bond formation. In some embodiments, the soluble ENPP1 polypeptide lacks SMB domain 1. In some embodiments, the soluble ENPP1 polypeptide lacks SMB2. In some embodiments, the soluble ENPP1 polypeptide lacks both SMB1 and SMB2. In certain cases the ENPP1 polypeptide further lacks a negatively-charged bone-targeting domain.

In certain embodiments, the ENPP1 polypeptide comprises a signal peptide resulting in the secretion of a precursor of the ENPP1 polypeptide, which undergoes proteolytic processing to yield a polypeptide comprising the soluble ENPP1 polypeptide. In other embodiments, the signal peptide is selected from the group consisting of signal peptides of ENPP2, ENPP5, and ENPP7. In some embodiments, the ENPP1 polypeptide comprises an ENPP1 polypeptide comprising transmembrane domains of ENPP1 and another polypeptide, such as, by way of non-limiting example, ENPP2. In some embodiments, the ENPP1 polypeptide comprises a cleavage product of a precursor ENPP1 polypeptide comprising an ENPP2 transmembrane domain. In some embodiments, the ENPP2 transmembrane domain comprises the amino acid sequence IISLFTFAVGVNI-CLGFTA (SEQ ID NO: 20).

In certain embodiments, the soluble ENPP1 polypeptide is modified with a segment of the extracellular region of ENPP1 comprising a peptidase cleavage site after the signal peptide, and between the transmembrane and extracellular domain, as compared to SEQ ID NO: 1. In certain embodiments, the soluble ENPP1 polypeptide is modified with a segment of the extracellular region of ENPP1 comprising a furin cleavage site between the transmembrane and extracellular domain, as compared to SEQ ID NO: 1. In other embodiments, the soluble ENPP1 polypeptide is not modified with a segment of the extracellular region of ENPP1 comprising a furin cleavage site between the transmembrane and extracellular domain, as compared to SEQ ID NO:1. In certain embodiments, the soluble ENPP1 polypeptide is modified with a segment of the extracellular region of ENPP2 containing a signal peptidase cleavage site, as compared to SEQ ID NO: 1. In other embodiments, the soluble ENPP1 polypeptide is not modified with a segment of the extracellular region of ENPP2 containing a signal peptidase cleavage site, as compared to SEQ ID NO: 1.

In some embodiments, the soluble ENPP1 polypeptide has reduced ability to homodimerize as compared to soluble wild-type ENPP1 polypeptide. In some embodiments, the soluble ENPP1 polypeptide comprises one or more amino acid modifications (e.g., deletion of SMB1 and/or SMB2) that reduce homodimerization of the ENPP1 polypeptide. In some embodiments, the one or more amino acid modifications reduce homodimerization by at least 1%, 2%, 3%, 4%, 5%, 6%, 7%, 8%, 9%, 10%, 15%, 20%, 30%, 40%, 50%, 60%, 70%, 80%, 90% or 100%. In some embodiments, the soluble ENPP1 polypeptide does not have reduced ability to homodimerize as compared to soluble wild-type ENPP1 polypeptide. In some embodiments, the soluble ENPP1 polypeptide homodimerizes at least 1%, 2%, 3%, 4%, 5%, 6%, 7%, 8%, 9%, 10%, 15%, 20%, 30%, 40%, 50%, 60%, 70%, 80%, 90% or 100% as compared to a wild-type ENPP1 polypeptide. In some embodiments, the polypeptide has reduced affinity for the human insulin receptor (IR) as compared to soluble wild-type ENPP1 polypeptide. In some embodiments, the polypeptide comprises one or more amino acid modifications that reduce the affinity of ENPP1 for the human IR. In some embodiments, the one or more amino acid modifications reduce the affinity of ENPP1 for the human IR by at least 1%, 2%, 3%, 4%, 5%, 6%, 7%, 8%, 9%, 10%, 15%, 20%, 30%, 40%, 50%, 60%, 70%, 80%, 90% or 100%. In some embodiments, the soluble ENPP1 polypeptide comprises the phosphodiesterase catalytic domain of ENPP1. In some embodiments, the soluble ENPP1 polypeptide lacks SMB1. For instance, soluble ENPP1 polypeptides may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 145 to 925 of SEQ ID NO: 1. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 142 to 925 of SEQ ID NO: 1. In some embodiments, a soluble ENPP1 polypeptide lacks SMB2. For instance, soluble ENPP1 polypeptides may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 107 to 144 of SEQ ID NO: 1 and residues 190 to 925 of SEQ ID NO: 1. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96% 97%, 98%, 99%, or 100% identical to residues 100 to 142 of SEQ ID NO: 1 and residues 187 to 925 of SEQ ID NO: 1. In some embodiments, a soluble ENPP1 polypeptide lacks SMB2 and the first linker domain. In some embodiments, a soluble ENPP1 polypeptide lacks SMB1 and SMB2. For instance, soluble ENPP1 poly peptides may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 188 to 925 of SEQ ID NO: 1. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 190 to 925 of SEQ ID NO: 1. In some embodiments, a soluble ENPP1 polypeptide lacks SMB1, SMB2, and the first linker domain. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 9. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 10. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 121. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, %%, 97%, 98%, 99%, or 100% identical to SEQ ID NO: 122. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 127. In some embodiments, a soluble ENPP1 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 128. In some embodiments, the soluble ENPP1 polypeptide further comprises one or more mutations in the extracellular domain of an ENPP1 polypeptide such that the soluble ENPP1 polypeptide demonstrates greater proteolytic resistance to a protease than the corresponding wild-type soluble ENPP1 polypeptide. In some embodiments, the soluble ENPP1 polypeptide lacks one or both of SMB domains 1 and 2. In some embodiments, the soluble ENPP1 poly peptide lacks a nuclease domain. In some embodiments, the soluble ENPP1 polypeptide is truncated to remove the nuclease domain. In some embodiments, the soluble ENPP1 polypeptide is truncated to remove the nuclease domain from about residue 524 to about residue 885 relative to SEQ ID NO: 1, leaving only the catalytic domain from about residue 186 to about residue 586 relative to SEQ ID NO: 1, which serves to preserve the catalytic activity of the protein. In some embodiments, the present disclosure contemplates further introducing substitutions in one or more domains of a soluble ENPP1 polypeptide, such as, for example, one or more substitutions in the catalytic and/or nuclease domain as described herein.

In certain embodiments, the soluble ENPP1 polypeptide is a recombinant polypeptide. In some embodiments, the soluble ENPP1 polypeptide comprises an ENPP1 polypeptide that lacks the ENPP1 transmembrane domain. In some embodiments, the polypeptide comprises an ENPP1 polypeptide w % herein the ENPP1 transmembrane domain has been removed (and/or truncated) and replaced with the transmembrane domain of another polypeptide, such as, by way of non-limiting example, ENPP2. ENPP5, or ENPP7.

In some embodiments, the soluble ENPP1 polypeptide is a fusion protein comprising an ENPP1 polypeptide domain and one or more heterologous protein portions (i.e., polypeptide domains heterologous to ENPP1). An amino acid sequence is understood to be heterologous to ENPP1 if it is not uniquely found in the form of ENPP1 represented by SEQ ID NO: 1. In some embodiments, the heterologous protein portion comprises an Fc domain of an immunoglobulin. In some embodiments, the Fc domain of the immunoglobulin is an Fc domain of an IgG1 immunoglobulin. In certain embodiments, the soluble ENPP1 polypeptide is C-terminally fused to the Fc domain of human immunoglobulin 1 (IgG1), human immunoglobulin 2 (IgG2), human immunoglobulin 3 (IgG3), and/or human immunoglobulin 4 (IgG4). In other embodiments, the soluble ENPP1 polypeptide is N-terminally fused to the Fc domain of human immunoglobulin 1 (IgG1), human immunoglobulin 2 (IgG2), human immunoglobulin 3 (IgG3), and/or human immunoglobulin 4 (IgG4). In some embodiments, the presence of an Fc domain improves half-life, solubility, reduces immunogenicity, and increases the activity of the soluble ENPP1 polypeptide. In certain embodiments, portions of the native human IgG proteins (IgG1, IgG2, IgG3, and IgG4), may be used for the Fc portion (e.g., ENPP1-Fc). For instance, the present disclosure provides fusion proteins comprising ENPP1 fused to a polypeptide comprising a constant domain of an immunoglobulin, such as a CH1, CH2, or CH3 domain derived from human IgG1, IgG2, IgG3, and/or IgG4. The Fc fragment may comprise regions of the native IgG such as the hinge region (residues 216-230 of human IgG1, according to the Rabat numbering system), the entire second constant domain CH2 (residues 231-340), and the third constant domain CH3 (residues 341-447). As used herein, the term "ENPP1-Fc construct" refers to a soluble form of ENPP1 (e.g., the extracellular domain of an ENPP1 polypeptide) recombinantly fused and/or chemically conjugated (including both covalent and non-covalent conjugations) to an FcR binding domain of an IgG molecule (preferably, a human IgG). In certain embodiments, the C-terminus of ENPP1 is fused or conjugated to the N-terminus of the FcR binding domain. In certain embodiments, the N-terminus of ENPP1 is fused or conjugated to the C-terminus of the FcR binding domain.

In some embodiments, the Fc domain comprises a variant Fc constant region. In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three, or two) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259I, T250I, and V308F. In some embodiments, the variant Fc constant region comprises the amino acid substitutions M252Y, S254T, and T256E. In some embodiments, the variant human Fc constant region comprises a methionine at position 428 and an asparagine at position 434, each in EU numbering. In some embodiments, the variant Fc constant region comprises a 428L/434S double substitution as described in, e.g., U.S. Pat. No. 8,088,376. In some embodiments, a method for determining whether a functional equivalent or functional derivative has the same or similar or higher biological activity than an ENPP1-Fc construct disclosed herein can be determined by using the enzymology assays involving ATP cleavage described in WO 2016/187408.

An example of an amino acid sequence that may be used for the Fc portion of human IgG1 (G1Fc) is SEQ ID NO: 13 (Table 1). In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 13. In some embodiments, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 16.

In some embodiments, the heterologous protein portion comprises one or more domains selected from the group consisting of polyhistidine (SEQ ID NO: 130), FLAG tag, Glu-Glu, glutathione S-transferase (GST), thioredoxin, protein A, protein G, an immunoglobulin heavy-chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAEXPRESS™ system (Qiagen) useful with (HIS$_6$) fusion partners. As another example, a fusion domain may be selected so as to facilitate detection of the ENPP1 polypeptide. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for Factor Xa or thrombin, which allows the relevant protease to partially digest the fusion proteins and thereby liberate the recombinant proteins therefrom. The liberated proteins can then be isolated from the fusion domain by subsequent chromatographic separation. Other types of fusion domains may be selected to increase the circulating half-life of a soluble ENPP1 polypeptide. For instance, fusion domains that may be selected include multimerizing (e.g., dimerizing, tetramerizing) domains and functional domains (that confer an additional biological function). In some embodiments, the heterologous protein portion reduces aggregation of the soluble ENPP1 polypeptide. In some embodiments, the heterologous protein portion decreases immunogenicity of the ENPP1 polypeptide. In some embodiments, the heterologous protein portion (e.g., Fc domain) increases dimerization of the soluble ENPP1 polypeptide. For instance, the SMB1 and the SMB2 domains have been reported to take part in ENPP1 dimerization (R. Gijsbers, H. et al., Biochem. J. 371; 2003: 321-330). Accordingly, deletion of the SMB1 and the SMB2 domains may result in increased monomeric soluble ENPP1 polypeptide. In some embodiments, the soluble ENPP1 polypeptide is monomeric. In some embodiments, the soluble ENPP1 polypeptide is dimeric. In some embodiments, the soluble ENPP1 polypeptide lacking SMB1 and SMB2 further comprises an Fc domain. In some embodiments, the soluble ENPP1 polypeptide lacking SMB1 and SMB2 further comprises an Fc domain which increases dimerization of the soluble ENPP1 polypeptide.

In some embodiments, the ENPP1 fusion protein further comprises a linker positioned between the ENPP1 polypeptide domain and the one or more heterologous protein portions (e.g., an Fc immunoglobulin domain). In certain embodiments, the soluble ENPP1 polypeptide is directly or indirectly fused to the Fc domain. In some embodiments, the soluble ENPP1 fusion protein comprises a linker between the Fc domain and the ENPP1 polypeptide. In some embodiments, a linker can be an amino acid spacer including 1-200 amino acids. Suitable peptide spacers are known in the art, and include, for example, peptide linkers containing flexible amino acid residues such as glycine, alanine, and serine. In some embodiments, the linker comprises a polyglycine linker or a Gly-Ser linker. In some embodiments, a spacer can contain motifs, e.g., multiple or repeating motifs, of GA (SEQ ID NO: 21), GS (SEQ ID NO: 22), GG (SEQ ID NO: 23), GGA (SEQ ID NO: 24), GGS (SEQ ID NO: 25), GGG (SEQ ID NO: 26), GGGA (SEQ ID NO: 27), GGGS (SEQ ID NO: 28), GGGG (SEQ ID NO: 29), GGGGA (SEQ ID NO: 30), GGGGS (SEQ ID NO: 31), GGGGG (SEQ ID NO: 32), GGAG (SEQ ID NO: 33), GGSG (SEQ ID NO: 34), AGGG (SEQ ID NO: 35), SGGGG (SEQ ID NO: 36), or SGGG (SEQ ID NO: 37). In some embodiments, a spacer can contain 2 to 12 amino acids including motifs of GA or GS, e.g., GA, GS, GAGA (SEQ ID NO: 38), GSGS (SEQ ID NO: 39), GAGAGA (SEQ ID NO: 40), GSGSGS (SEQ ID NO: 41), GAGAGAGA (SEQ ID NO: 42), GSGSGSGS (SEQ ID NO: 43), GAGAGAGAGA (SEQ ID NO: 44), GSGSGSGSGS (SEQ ID NO: 45), GAGAGAGAGAGA (SEQ ID NO: 46), and GSGSGSGSGSGS (SEQ ID NO: 47). In some embodiments, a spacer can contain 3 to 12 amino acids including motifs of GGA or GGS, e.g., GGA, GGS, GGAGGA (SEQ ID NO: 48), GGSGGS (SEQ ID NO: 49), GGAGGAGGA (SEQ ID NO: 50), GGSGGSGGS (SEQ ID NO: 51), GGAGGAGGAGGA (SEQ ID NO: 52), and GGSGGSGGSGGS (SEQ ID NO: 53). In yet some embodiments, a spacer can contain 4 to 12 amino acids including motifs of GGAG (SEQ ID NO: 54), GGSG (SEQ ID NO: 55), e.g., GGAG (SEQ ID NO: 56), GGSG (SEQ ID NO: 57), GGAGGGAG (SEQ ID NO: 58), GGSGGGSG (SEQ ID NO: 59), GGAGGGAGGGAG (SEQ ID NO: 60), and GGSGGGSGGGSG (SEQ ID NO: 61). In some embodiments, a spacer can contain motifs of GGGGA (SEQ ID NO: 62) or GGGGS (SEQ ID NO: 63), e.g., GGG-GAGGGGAGGGGA (SEQ ID NO: 64) and GGGGSGGGGSGGGGS (SEQ ID NO: 65). In some embodiments of the invention, an amino acid spacer between a heterologous protein portion (e.g., an Fc domain monomer, a wild-type Fc domain, an Fc domain with amino acid substitutions (e.g., one or more substitutions that reduce dimerization), an albumin-binding peptide, a fibronectin domain, or a human serum albumin) and a soluble ENPP1 polypeptide may be GGG, GGGA (SEQ ID NO: 27), GGGG (SEQ ID NO: 29), GGGAG (SEQ ID NO: 66), GGGAGG (SEQ ID NO: 67), or GGGAGGG (SEQ ID NO: 68).

In some embodiments, a spacer can also contain amino acids other than glycine, alanine, and serine, e.g., LIN (SEQ ID NO: 69), TGGGG (SEQ ID NO: 70), AAAL (SEQ ID NO: 71), AAAK (SEQ ID NO: 72), AAAR (SEQ ID NO: 73), EGKSSGSGSESKST (SEQ ID NO: 74), GSAGSAAGSGEF (SEQ ID NO: 75), AEAAAKEAAAKA (SEQ ID NO: 76), KESGSVSSEQLAQFRSLD (SEQ ID NO: 77), GENLYFQSGG (SEQ ID NO: 78), SACYCELS (SEQ ID NO: 79), RSIAT (SEQ ID NO: 80), RPACK-IPNDLKQKVMNH (SEQ ID NO: 81), GGSAGGSGSGSSGGSSGASGTGTAGGTGSGSGTGSG (SEQ ID NO: 82), AAANSSIDLISVPVDSR (SEQ ID NO: 83), GGSGGGSEGGGSEGGGSEGGG-SEEGGGSEGGGSGGGS (SEQ ID NO: 84), NSS (SEQ ID NO: 87), ESS (SEQ ID NO: 88), RQQ (SEQ ID NO: 89), KR (SEQ ID NO: 90). $(R)_m$ wherein m is from 0-15 (SEQ ID NO: 91), DSSSEEKFLRRIGRFG (SEQ ID NO: 92), EEEEEEEPRGDT (SEQ ID NO: 93), APWHLSSQYSRT (SEQ ID NO: 94), STLPIPHEFSRE (SEQ ID NO: 95), VTKHLNQISQSY (SEQ ID NO: 96), $(E)_m$ wherein m is from 1-15 (SEQ ID NO: 97), RSGSGGS (SEQ ID NO: 98), $(D)_m$ wherein m is from 1-15 (SEQ ID NO: 99). LVIM-SLGLGLGLGLGLRK (SEQ ID NO: 100), VIM-SLGLGLGLGLGLRK (SEQ ID NO: 101), IMSLGLGLGLGLGLRK (SEQ ID NO: 102), MSLGLGLGLGLGLRK (SEQ ID NO: 103), SLGLGLGLGLRK (SEQ ID NO: 104), LGLGLGLGLRK (SEQ ID NO: 105), GLGLGLGLRK (SEQ ID NO: 106), LGLGLGLRK (SEQ ID NO: 107), GLGLGLRK (SEQ ID NO: 108), LGLGLRK (SEQ ID NO: 109), GLGLRK (SEQ ID NO: 110), LGLRK (SEQ ID NO: 111), GLRK (SEQ ID NO: 112), LRK (SEQ ID NO: 113), RK (SEQ ID NO: 114), or $(K)_m$ wherein m is from 1-15 (SEQ ID NO: 115). In some embodiments, a spacer can contain motifs, e.g., multiple or repeating motifs, of EAAAK (SEQ ID NO: 85). In some embodiments, a spacer can contain motifs, e.g., multiple or repeating motifs, of praline-rich sequences such as $(XP)_n$, (SEQ ID NO: 134) in which X may be any amino acid (e.g., A, K, or E) and n is from 1-5, and PAPAP (SEQ ID NO: 86).

The length of the peptide spacer and the amino acids used can be adjusted depending on the two protein involved and the degree of flexibility desired in the final protein fusion polypeptide. The length of the spacer can be adjusted to ensure proper protein folding and avoid aggregate formation.

In some embodiments, the heterologous protein portion comprises a human serum albumin polypeptide. In some embodiments, the human serum albumin polypeptide is fused C-terminally to the ENPP1 polypeptide. In certain embodiments, the soluble ENPP1 polypeptide is N-terminally fused to human serum albumin. Human serum albumin may be conjugated to the soluble ENPP1 polypeptide through a chemical linker, including but not limited to naturally occurring or engineered disulfide bonds, or by genetic fusion to the soluble ENPP1 polypeptide, or a fragment and/or variant thereof.

In some embodiments, soluble ENPP1 polypeptides of the present disclosure include fusion proteins comprising a soluble ENPP1 polypeptide portion which lacks at least one Somatomedin B domain and a heterologous protein portion. In some embodiments, the ENPP1 polypeptide portion lacks SMB1. In some embodiments, the ENPP1 polypeptide portion lacks SMB2. In some embodiments, the ENPP1 polypeptide portion lacks SMB1 and SMB2. In some embodiments, the fusion protein further lacks a negatively-charged bone-targeting domain.

In some embodiments, soluble ENPP1 polypeptides of the present disclosure include fusion proteins comprising a soluble ENPP1 polypeptide portion which comprises an amino acid substitution at at least one of positions 816, 817, or 818 relative to SEQ ID NO: 1 and a heterologous protein portion. In some embodiments, the soluble ENPP1 polypeptide portion comprises an amino acid substitution at position 816. In some embodiments, the soluble ENPP1 polypeptide portion comprises an amino acid substitution at position 817. In some embodiments, the soluble ENPP1 polypeptide portion comprises an amino acid substitution at position 818. Amino acid substitutions at one or more of these positions may result in greater proteolytic resistance to a protease than a corresponding wild-type soluble ENPP1 polypeptide. ENPP1 polypeptides comprising an amino acid substitution at position 816, 817, and/or 818 have been produced and each of these mutants show biological activity.

Specifically. ENPP1 polypeptides comprising (1) an R818H mutation: (2) an R817H and R818H mutation; and (3) an K816H. R817H and R818H mutation each show biological activity.

In some embodiments, different elements of the fusion proteins (e.g., immunoglobulin Fc fusion proteins) may be arranged in any manner that is consistent with desired functionality. For example, a soluble ENPP1 polypeptide domain may be placed C-terminal to a heterologous protein portion, or alternatively, a heterologous protein portion may be placed C-terminal to a soluble ENPP1 polypeptide domain. The soluble ENPP1 polypeptide domain and the heterologous protein portion may be directly or indirectly linked in a fusion protein, and additional domains or amino acid sequences may be included C- or N-terminal to either domain or between the domains. Illustrative fusion proteins comprise the amino acid sequence set forth in any one of SEQ ID NOs: 9-12, 121, and 122.

In some embodiments, soluble ENPP1 polypeptides of the present disclosure contain one or more heterologous moieties. Optionally, a soluble ENPP1 polypeptide includes one or more heterologous moieties selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. In some embodiments, a soluble ENPP1 polypeptide disclosed herein is further modified. Such modifications include, but are not limited to, acetylation, carboxylation, glycosylation, phosphorylation, lipidation, and/or acylation. As a result, the soluble ENPP1 polypeptide may contain non-amino acid elements, such as polyethylene glycols, lipids, polysaccharide or monosaccharide, and phosphates. Effects of such non-amino acid elements on the functionality of a soluble ENPP1 polypeptide may be tested as described herein for other soluble ENPP1 polypeptides. When a polypeptide of the disclosure is produced in cells by cleaving a nascent form of the polypeptide, post-translational processing may also be important for correct folding and/or function of the protein. Different cells (e.g., CHO, HeLa, MDCK, 293, WI38, NIH-3T3 or HEK293) have specific cellular machinery and characteristic mechanisms for such post-translational activities and may be chosen to ensure the correct modification and processing of the soluble ENPP1 polypeptides.

In certain aspects, soluble ENPP1 polypeptides, and fusion proteins thereof, of the present disclosure may further comprise one or more modifications that are capable of "stabilizing" the polypeptides. By "stabilizing" is meant a modification that increases the in vitro half-life, serum half-life, regardless of whether this is because of decreased destruction, decreased clearance by the kidney, and/or other pharmacokinetic effect of said modification. For example, such modifications enhance the shelf-life of the polypeptides, enhance circulatory half-life of the polypeptides, and/ or reduce proteolytic degradation of the polypeptides. Such stabilizing modifications include, but are not limited to, modifications of a glycosylation site (including, for example, addition of a glycosylation site to a polypeptide of the disclosure), and modifications of carbohydrate moiety (including, for example, removal of carbohydrate moieties from a polypeptide of the disclosure).

In certain embodiments, the present disclosure contemplates specific mutations of a soluble ENPP1 polypeptide so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. In certain aspects, ENPP1 polypeptides of the present disclosure comprise mutations that introduce or eliminate one or more glycosylation sites. In certain embodiments, the mutations introduce or eliminate one or more O-linked or N-linked glycosylation sites. In certain embodiments, the mutations introduce one or more O-linked glycosylation sites. In certain embodiments, the mutations eliminate one or more O-linked glycosylation sites. In certain embodiments, the mutations introduce one or more N-linked glycosylation sites. In certain embodiments, the mutations eliminate one or more N-linked glycosylation sites. In certain embodiments, the mutations comprise substitution and/or deletion mutations. In certain embodiments, the mutations comprise substitutions and/or deletions at one or both of the first or third amino acid positions of a glycosylation recognition site. In certain embodiments, the mutations comprise amino acid substitutions and/or deletions at the first amino acid position of a glycosylation recognition site. In certain embodiments, the mutations comprise substitutions and/or deletions at the third amino acid position of a glycosylation recognition site. In certain embodiments, the mutations comprise amino acid substitutions and/or deletions at the second amino acid position of a glycosylation recognition site. In certain non-limiting embodiments, the mutations comprise amino acid substitutions at the second amino acid position of a glycosylation recognition site. In certain embodiments, the amino acid substitution at the second amino acid position of a glycosylation recognition site comprises a substitution at amino acid residue 332 with respect to SEQ ID NO: 1. In certain embodiments, amino acid residue 332 comprises an I332T substitution. In certain embodiments, the I332T substitution introduces one or more O-linked or N-linked glycosylation sites. In certain embodiments, the I332T substitution increases glycosylation of the ENPP1 polypeptide. In certain embodiments, the ENPP1 polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NOs: 9 or 12. In certain embodiments, the ENPP1 polypeptide comprises an I332T substitution mutation as relating to SEQ ID NO: 1.

Another means of increasing the number of carbohydrate moieties on a polypeptide is by chemical and/or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. In some embodiments, removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. In some embodiments, this treatment may result in the cleavage of most or all sugars except the linking sugar (N-acetyhlglucosamine or N-acetyl-galactosamine), while leaving the amino acid sequence intact. In some embodiments, enzymatic cleavage of carbohydrate moieties on polypeptides can be achieved by the use of a variety of endo- and exo-glycosidases as described by Thotakura et al. [Meth. Enzymol. (1987) 138:350]. In some embodiments, the sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, polypeptides of the present disclosure for use in humans may be expressed in a mammalian cell line that provides proper glycosylation, such as HEK293 or CHO cell lines, although other mammalian expression cell lines are expected to be useful as well.

In certain embodiments, the soluble ENPP1 polypeptide lacks a negatively-charged bone-targeting domain. In some embodiments, a polyaspartic acid domain (from about 2 to about 20 or more sequential aspartic acid residues) is a non-limiting example of a negatively-charged bone-targeting domain. In some embodiments, the negatively-charged bone-targeting domain comprises a polyaspartic acid domain comprising 8 sequential aspartic acid residues. In some embodiments, the negatively-charged bone-targeting domain comprises a polyaspartic acid domain comprising 10 sequential aspartic acid residues. In some embodiments, the negatively-charged bone-targeting domain comprises a polyaspartic acid domain comprising 2 sequential aspartic acid residues, 3 sequential aspartic acid residues, 4 sequential aspartic acid residues, 5 sequential aspartic acid residues, 6 sequential aspartic acid residues 7 sequential aspartic acid residues, 8 sequential aspartic acid residues, 9 sequential aspartic acid residues, 10 sequential aspartic acid residues, 11 sequential aspartic acid residues, 12 sequential aspartic acid residues, 13 sequential aspartic acid residues, 14 sequential aspartic acid residues, 15 sequential aspartic acid residues, 16 sequential aspartic acid residues, 17 sequential aspartic acid residues, 18 sequential aspartic acid residues, 19 sequential aspartic acid residues, or 20 sequential aspartic acid residues. In some embodiments, the soluble ENPP1 polypeptide comprises a negatively-charged bone-targeting domain. In some embodiments, a soluble ENPP1 polypeptide disclosed herein lacks a negatively-charged bone-targeting domain as previously described (PCT Application Publication Nos. WO 2011/113027 and WO 2012/125182).

In certain aspects, the present disclosure relates to ENPP1-related proteins. In certain embodiments, the ENPP1-related polypeptide is ENPP2, ENPP3, ENPP4, ENPP5. ENPP6, or ENPP7. In certain non-limiting embodiments, the ENPP1-related polypeptide is ENPP3. ENPP3 polypeptides disclosed herein include naturally occurring polypeptides of the ENPP3 family as well as any variants thereof (including mutants, fragments, fusions, and peptidomimetic forms) that retain a biological activity.

A person of skill in the art would recognize that the residues corresponding to various domains of an ENPP3 polypeptide may vary. Specifically, the identification of polypeptide domains is classically based upon the protein sequence and/or structure. The polypeptide sequence and/or structure can be used to identify related polypeptide domains (i.e., the polypeptide may have sequence and/or structural resemblance to other protein structures or domains). In some embodiments, the SMB1 domain of ENPP3 comprises an amino acid sequence that begins at any one of amino acids 41, 42, 43, 44, 45, 46, 47 48, 49, 50, or 51 of SEQ ID NO: 116 and ends at any one of amino acids 86, 87, 88, 89, 90, 91, 92, 93, 94, 95, or 96 of SEQ ID NO: 116. In some embodiments, the SMB1 domain of ENPP3 comprises an amino acid sequence that begins at an amino acid residue 5 residues upstream or downstream of amino acid residue 46 of SEQ ID NO: 116 and ends at an amino acid residue ±5 residues upstream or downstream of amino acid residue 91 of SEQ ID NO: 116. In some embodiments, the SMB1 domain of ENPP3 comprises amino acid residues 46-91 of SEQ ID NO: 116.

In some embodiments, the SMB2 domain of ENPP3 comprises an amino acid sequence that begins at any one of amino acids 87, 88, 89, 90, 91, 92, 93, 94, 95, 96, or 97 of SEQ ID NO: 116 and ends at any one of amino acids 130, 131, 132, 133, 134, 135, 136, 137, 138, 139, or 140 of SEQ ID NO: 116. In some embodiments, the SMB2 domain of ENPP3 comprises an amino acid sequence that begins at an amino acid residue ±5 residues upstream or downstream of amino acid residue 92 of SEQ ID NO: 116 and ends at an amino acid residue ±5 residues upstream or downstream of amino acid residue 135 of SEQ ID NO: 116. In some embodiments, the SMB2 domain of ENPP3 comprises amino acid residues 92-135 of SEQ ID NO: 116.

In some embodiments, the first linker domain ("L1" as shown in FIG. 7) comprises an amino acid sequence that begins at any one of amino acids 132, 134, 135, 136, 137, 138, or 139 of SEQ ID NO. 116 and ends at any one of amino acids 157, 158, 159, 160, 161, 162, or 163 of SEQ ID NO. 116. In some embodiments, the first linker domain of ENPP3 comprises an amino acid sequence that begins at an amino acid residue ±3 residues upstream or downstream of amino acid residue 136 of SEQ ID NO: 116 and ends at an amino acid residue ±3 residues upstream or downstream of amino acid residue 160 of SEQ ID NO: 116. In some embodiments, the first linker domain of ENPP3 comprises amino acid residues 136-160 of SEQ ID NO: 116.

In some embodiments, the catalytic domain (phosphodiesterase domain) of ENPP3 comprises an amino acid sequence that begins at any one of amino acids 150, 151, 152, 153, 154, 155, 156, 157, 158, 159, 160, 161, 162, or 163 of SEQ ID NO: 116 and ends at any one of amino acids 535, 536, 537, 538, 539, 540, 541, 542, 543, 544, 545, 546, 547, 548, 549, or 550 of SEQ ID NO: 116. In some embodiments, the catalytic domain of ENPP3 comprises an amino acid sequence that begins at an amino acid residue ±10 residues upstream or downstream of amino acid residue 161 of SEQ ID NO: 116 and ends at an amino acid residue ±5 residues upstream or downstream of amino acid residue 545 of SEQ ID NO: 116. In some embodiments, the catalytic domain comprises residues 161-545 of SEQ ID NO: 116.

In some embodiments, the nuclease-like domain of ENPP3 comprises an amino acid sequence that begins at any one of amino acids 575, 576, 577, 578, 579 580, 581, 582, 583, 584, or 585 of SEQ ID NO: 116 and ends at any one of amino acids 870, 871, 872, 873, 874, or 875 of SEQ ID NO: 116. In some embodiments, the nuclease-like domain of ENPP3 comprises an amino acid sequence that begins at an amino acid residue ±5 residues upstream or downstream of amino acid residue 583 of SEQ ID NO: 116 and ends at an amino acid residue ±2 residues upstream or downstream of amino acid residue 875 of SEQ ID NO: 116. In some embodiments, the nuclease-like domain comprises residues 583-875 of SEQ ID NO: 116.

In certain embodiments, the present disclosure contemplates introducing deletions in the extracellular domain of a soluble ENPP3 polypeptide such that the soluble ENPP3 polypeptide has decreased immunogenicity as compared to the corresponding wild-type soluble ENPP3 polypeptide. In some embodiments, the present disclosure contemplates introducing deletions in the extracellular domain of an ENPP3 polypeptide such that the soluble ENPP3 polypeptide has decreased protein aggregation as compared to the corresponding wild-type soluble ENPP3 polypeptide. For instance, the SMB1 and SMB2 domains may be aggregation prone due to increased numbers of cysteine residues that are involved in disulfide bond formation. In some embodiments, the soluble ENPP3 polypeptide lacks SMB1. In some embodiments, the soluble ENPP3 polypeptide lacks SMB2. In some embodiments, the soluble ENPP3 polypeptide lacks both SMB1 and SMB2. In certain cases the ENPP3 polypeptide further lacks a negatively-charged bone-targeting domain.

In certain embodiments, the ENPP3 polypeptide comprises a signal peptide resulting in the secretion of a precursor of the ENPP3 polypeptide, which undergoes proteolytic processing to yield a polypeptide comprising the soluble ENPP3 polypeptide. In other embodiments, the signal peptide is selected from the group consisting of signal peptides of ENPP2, ENPP5, and ENPP7. In some embodiments, the ENPP3 polypeptide comprises an ENPP3 polypeptide comprising transmembrane domains of ENPP3 and another polypeptide, such as, by way of non-limiting example, ENPP2. In some embodiments, the ENPP3 polypeptide comprises a cleavage product of a precursor ENPP3 polypeptide comprising an ENPP2 transmembrane domain. In some embodiments, the ENPP2 transmembrane domain comprises the amino acid sequence IISLFTFAVGVNI-CLGFTA (SEQ ID NO: 20).

In some embodiments, the soluble ENPP3 polypeptide has reduced ability to homodimerize as compared to the wild-type soluble ENPP3 polypeptide. In some embodiments, the soluble ENPP3 polypeptide comprises one or more amino acid modifications (e.g., deletion of SMB1 and/or SMB2) that reduce homodimerization of the ENPP3 polypeptide. In some embodiments, the one or more amino acid modifications reduce homodimerization by at least 1%, 2%, 3%, 4%, 5%, 6%, 7%, 8%, 9%, 10%, 15%, 20%, 30%, 40%, 50%, 60%, 70%, 80%, 90% or 100%. In some embodiments, the soluble ENPP3 polypeptide does not have reduced ability to homodimerize. In some embodiments, the soluble ENPP3 polypeptide homodimerizes at least 1%, 2%, 3%, 4%, 5%, 6%, 7%, 8%, 9%, 10%, 15%, 20%, 30%, 40%, 50%, 60%, 70%, 80%, 90% or 100% as compared to a wild-type ENPP3 polypeptide. In some embodiments, the polypeptide has reduced affinity for the human insulin receptor (IR) as compared to the wild-type soluble ENPP3 polypeptide. In some embodiments, the polypeptide comprises one or more amino acid modifications that reduce the affinity of ENPP3 for the human IR. In some embodiments, the one or more amino acid modifications reduce the affinity of ENPP3 for the human IR by at least 1%, 2%, 3%, 4%, 5%, 6%, 7%, 8%, 9%, 10%, 15%, 20%, 30%, 40%, 50%, 60%, 70%, 80%, 90% or 100%. In some embodiments, the soluble ENPP3 polypeptide comprises the phosphodiesterase catalytic domain of ENPP3. In some embodiments, the soluble ENPP3 polypeptide lacks SMB1. For instance, a SMB1 domain of a soluble ENPP3 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%. 98%, 99%, or 100% identical to residues 45-90 of SEQ ID NO: 116. In some embodiments, a soluble ENPP3 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 91-875 of SEQ ID NO: 116. In some embodiments, a soluble ENPP3 polypeptide lacks SMB2. For instance, a SMB2 domain of a soluble ENPP3 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 92-135 of SEQ ID NO: 116. In some embodiments, a soluble ENPP3 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 46 to 91 of SEQ ID NO: 116 and residues 136 to 875 of SEQ ID NO: 116. In some embodiments, a soluble ENPP3 polypeptide lacks SMB2 and the first linker domain. In some embodiments, a soluble ENPP3 polypeptide lacks SMB1 and SMB2. For instance, a SMB1 and SMB2 domain of a soluble ENPP3 polypeptides may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 46 to 135 of SEQ ID NO: 116. In some embodiments, a soluble ENPP3 polypeptide may comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to residues 136 to 875 of SEQ ID NO: 116. In some embodiments, a soluble ENPP3 polypeptide lacks SMB1, SMB2, and the first linker domain. In some embodiments, the soluble ENPP3 polypeptide further comprises one or more mutations in the extracellular domain of an ENPP3 polypeptide such that the soluble ENPP3 polypeptide demonstrates greater proteolytic resistance to a protease than the corresponding wild-type soluble ENPP3 polypeptide. In some embodiments, the soluble ENPP3 polypeptide lacks one or both of SMB domains 1 and 2. In some embodiments, the soluble ENPP3 polypeptide lacks a nuclease domain. In some embodiments, the soluble ENPP3 polypeptide is truncated to remove the nuclease domain. In some embodiments, the soluble ENPP3 polypeptide is truncated to remove the nuclease domain from about residue 583 to about residue 875 relative to SEQ ID NO: 116, leaving only the catalytic domain from about residue 161 to about residue 545 relative to SEQ ID NO: 116, which serves to preserve the catalytic activity of the protein. In some embodiments, the present disclosure contemplates further introducing substitutions in one or more domains of a soluble ENPP3 polypeptide, such as, for example, one or more substitutions in the catalytic and/or nuclease domain as described herein.

In certain embodiments, the soluble ENPP3 polypeptide is a recombinant polypeptide. In some embodiments, the soluble ENPP3 polypeptide comprises an ENPP3 polypeptide that lacks the ENPP3 transmembrane domain. In some embodiments, the polypeptide comprises an ENPP3 polypeptide wherein the ENPP3 transmembrane domain has been removed (and/or truncated) and replaced with the transmembrane domain of another polypeptide, such as, by way of non-limiting example, ENPP2, ENPP5, and/or ENPP7.

In some embodiments, the soluble ENPP3 polypeptide is a fusion protein comprising an ENPP3 polypeptide domain and one or more heterologous protein portions (i.e., polypeptide domains heterologous to ENPP3). An amino acid sequence is understood to be heterologous to ENPP3 if it is not uniquely found in the form of ENPP3 represented by SEQ ID NO: 116. In some embodiments, the heterologous protein portion comprises an Fc domain of an immunoglobulin. In some embodiments, the Fc domain of the immunoglobulin is an Fc domain of an IgG1 immunoglobulin. In certain embodiments, the soluble ENPP3 polypeptide is C-terminally fused to the Fc domain of human immunoglobulin 1 (IgG1), human immunoglobulin 2 (IgG2), human immunoglobulin 3 (IgG3), and/or human immunoglobulin 4 (IgG4). In other embodiments, the soluble ENPP3 polypeptide is N-terminally fused to the Fc domain of human immunoglobulin 1 (IgG1), human immunoglobulin 2 (IgG2), human immunoglobulin 3 (IgG3), and/or human immunoglobulin 4 (IgG4). In some embodiments, the presence of an Fc domain improves half-life, solubility, reduces immunogenicity, and/or increases the activity of the soluble ENPP3 polypeptide as compared to the wild-type soluble ENPP3 polypeptide. In certain embodiments, portions of the native human IgG proteins (IgG1, IgG2, IgG3, and IgG4), may be used for the Fc portion (e.g., ENPP3-Fc). For instance, the present disclosure provides fusion proteins comprising ENPP3 fused to a polypeptide comprising a constant domain of an immunoglobulin, such as a CH1, CH2, or CH3 domain derived from human IgG1, IgG2, IgG3, and/or IgG4. The Fc fragment may comprise regions of the native IgG such as the hinge region (residues 216-230 of human IgG1, according to the Rabat numbering system), the entire second constant domain CH2 (residues 231-340), and the third constant domain CH3 (residues 341-447). In some embodiments, the Fc domain comprises a variant Fc constant region. The ENPP3 fusion Fc domain and Fc constant region may comprise amino acid substitutions, insertions, and/or deletions relative to the native constant region from which it was derived as described above. The ENPP3 fusion may comprise a heterologous protein portion comprising one or more domains, and/or a linker or a spacer positioned between the ENPP3 polypeptide domain and the one or more heterologous protein portions (e.g., an Fc immunoglobulin domain) selected from the groups described above.

As used herein, percent "identity" between a polypeptide sequence and a reference sequence is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, or CLUSTAL OMEGA software. In some embodiments, alignment is performed using the CLUSTAL OMEGA software. Those skilled in the art can determine appropriate parameters for aligning sequences, including any algorithms needed to achieve maximal alignment over the full length of the sequences being compared.

The present disclosure further contemplates a method of generating mutants, particularly sets of combinatorial mutants of a soluble ENPP1 and/or ENPP3 polypeptide as well as truncation mutants. Pools of combinatorial mutants are especially useful for identifying functionally active (e.g., conversion of nucleotides into inorganic pyrophosphate) ENPP1 sequences. The purpose of screening such combinatorial libraries may be to generate, for example, polypeptides variants which have altered properties, such as altered pharmacokinetic or altered stability (e.g., greater proteolytic resistance). A variety of screening assays are provided below, and such assays may be used to evaluate variants. For example, soluble ENPP1 and/or ENPP3 polypeptides disclosed herein may be screened for increased proteolytic resistance to a protease (e.g., trypsin or trypsin-like proteases) or decreased formation of anti-drug antibodies (e.g., decreased immunogenicity). Soluble ENPP1 and/or ENPP3 polypeptides disclosed herein may be further screened for ability to bind to one or more of ATP, UTP, GTP, TTP, CTP, or to hydrolyze extracellular nucleotide triphosphates to produce iorganic pyrophsphates (PPi).

In some embodiments, the activity of soluble ENPP1 and/or ENPP3 polypeptides may also be tested in a cell-based or in vivo assay. For example, the effect of a soluble ENPP1 and/or ENPP3 polypeptide on the production of inorganic pyrophosphates (PPi) can be measured. Specifically, the pyrophosphatase/phosphodiesterase domain of an ENPP1 and/or ENPP3 protein hydrolyzes extracellular nucleotide triphosphates to produce inorganic pyrophosphates (PPi) and is generally soluble. This activity can be measured using a pNP-TMP assay as well as an HPLC-based ATP hydrolysis assay, as previously described (Saunders, et al., 2008, Mol. Cancer her, 7(10):3352-62; Albright, et al., 2015, Nat Comm. 6:10006). The effect of soluble ENPP1 and/or ENPP3 polypeptides on the expression of genes involved in ENPP1 and/or ENPP3 associated diseases such as ARHR2 (e.g., transcription of fibroblast growth factor 23 in osteoblasts and osteoclasts) can be assessed. This may, as needed, be performed in the presence of one or more nucleotide triphosphates or other ENPP1 and/or ENPP3 substrates, and cells may be transfected so as to produce a soluble ENPP1 polypeptide. Likewise, a soluble ENPP1 and/or ENPP3 polypeptide may be administered to a mouse or other animal and effects on ENPP1 and/or ENPP3 associated diseases may be assessed using art-recognized methods.

In some embodiments, combinatorial-derived variants can be generated which have increased proteolytic resistance to a protease (e.g., trypsin or trypsin-like proteases) or decreased formation of anti-drug antibodies (e.g., decreased immunogenicity) relative to a reference ENPP1 and/or ENPP3 polypeptide. Such variants, when expressed from recombinant DNA constructs, can be used in gene therapy protocols. Likewise, mutagenesis can give rise to variants which have intracellular half-lives dramatically different than the corresponding unmodified ENPP1 and/or ENPP3 polypeptide. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter the half-life of the soluble ENPP1 and/or ENPP3 polypeptide.

In some embodiments, a combinatorial library may be produced by way of a degenerate library of genes encoding a library of polypeptides which each include at least a portion of potential ENPP1 and/or ENPP3 polypeptide sequences. For instance, a mixture of synthetic oligonucleotides can be enzymatically ligated into gene sequences such that the degenerate set of potential ENPP1 and/or ENPP3 encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art [Narang, SA (1983) Tetrahedron 39:3; Itakura et al. (1981) Recombinant DNA, Proc. 3rd Cleveland Sympos. Macromolecules, ed. AG Walton, Amsterdam: Elsevier pp273-289; Itakura et al. (1984) Annu. Rev. Biochem. 53:323: Itakura et al. (1984) Science 198:1056; and Ike et al. (1983) Nucleic Acid Res. 11:477]. Such techniques have been employed in the directed evolution of other proteins [Scott et al., (1990) Science 249:386-390: Roberts et al. (1992) PNAS USA 89:2429-2433; Devlin et al. (1990) Science 249: 404-406; Cwirla et al., (1990) PNAS USA 87: 6378-6382: as well as U.S. Pat. Nos. 5,223,409, 5,198,346, and 5,096,8151.

Alternatively, other forms of mutagenesis can be utilized to generate a combinatorial library. For example, soluble ENPP1 and/or ENPP3 polypeptides of the disclosure can be generated and isolated from a library by screening using, for example, alanine scanning mutagenesis [Ruf et al. (1994) Biochemistry 33:1565-1572; Wang et al. (1994) J. Biol. Chem. 269:3095-3099: Balint et al. (1993) Gene 137:109-118: Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244:1081-10851, by linker scanning mutagenesis [Gustin et al. (1993) Virology 193:653-660; and Brown et al. (1992) Mol. Cell Biol. 12:2644-2652; McKnight et al. (1982) Science 232:316], by saturation mutagenesis [Meyers et al., (1986) Science 232: 6131, by PCR mutagenesis [Leung et al. (1989) Method Cell Mol Biol 1.11-19]; or by random mutagenesis, including chemical mutagenesis [Miller et al. (1992) A Short Course in Bacterial Genetics, CSHL Press, Cold Spring Harbor, NY; and Greener et al. (1994) Strategies in Mol Biol 7:32-34]. Linker scanning mutagenesis, particularly in a combinatorial setting, is another potential method for identifying mutated or truncated (bioactive) forms of ENPP1 and/or ENPP3 polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ENPP1 and/or ENPP3 polypeptides. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

As will be recognized by one of skill in the art, most of the described mutations, variants and/or modifications described herein may be made at the nucleic acid level or, in some cases, by post-translational modification or chemical synthesis. Such techniques are well known in the art and some of which are described herein. In part, the present disclosure identifies functionally active portions (fragments)

and variants of soluble ENPP1 and/or ENPP3 polypeptides that can be used as guidance for generating and using other soluble ENPP1 and/or ENPP3 polypeptides within the scope of the disclosure described herein.

In certain embodiments, functionally active fragments of soluble ENPP1 and/or ENPP3 polypeptides of the present disclosure can be obtained by screening polypeptides recombinantly produced from the corresponding fragment of the nucleic acid encoding a soluble ENPP1 and/or ENPP3 polypeptide. In addition, fragments can be chemically synthesized using techniques known in the art such as conventional Merrifield solid phase Fmoc or t-Boc chemistry. The fragments can be produced (recombinantly or by chemical synthesis) and tested to identify those peptidyl fragments that have functional characteristics, particularly with respect to proteolytic resistance to a protease (e.g., trypsin or trypsin-like proteases) or formation of anti-drug antibodies (e.g., decreased immunogenicity.

In some embodiments, ENPP1 and/or ENPP3 polypeptides to be used in accordance with the methods described herein are isolated polypeptides. As used herein, an isolated protein or polypeptide is one which has been separated from a component of its natural environment. In some embodiments, a polypeptide of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC) analyses. Methods for assessment of purity are well known in the art [see, e.g., Flatman et al., (2007) J. Chromatogr. B 848.79-87]. In some embodiments, soluble ENPP1 and/or ENPP3 polypeptides to be used in accordance with the methods described herein are recombinant polypeptides.

ENPP1 and/or ENPP3 polypeptides of the disclosure can be produced by a variety of art-known techniques. For example, polypeptides of the disclosure can be synthesized using standard protein chemistry techniques such as those described in Bodansky, M. Principles of Peptide Synthesis. Springer Verlag, Berlin (1993) and Grant G. A. (ed.). Synthetic Peptides: A User's Guide, W. H. Freeman and Company. New York (1992). In addition, automated peptide synthesizers are commercially available (e.g., Advanced ChemTech Model 396; Milligen/Biosearch 9600). Alternatively, the polypeptides of the disclosure, including fragments and/or variants thereof, may be recombinantly produced using various expression systems [e.g., *E. coli*, Chinese Hamster Ovary (CHO) cells, COS cells, baculovirus, Yeast *Pichia*] as is well known in the art. The protein can be produced in either adherent or suspension cells. In some embodiments, the fusion protein is expressed in CHO cells. To establish stable cell lines, the nucleic acid sequence encoding ENPP1 and/or ENPP3 constructs are cloned into an appropriate vector for large scale protein production. In a further embodiment, the modified or unmodified polypeptides of the disclosure may be produced by digestion of recombinantly produced full-length ENPP1 and/or ENPP3 polypeptides by using, for example, a protease, e.g., trypsin, thermolysin, chymotrypsin, pepsin, or paired basic amino acid converting enzyme (PACE). Computer analysis (using commercially available software, e.g., MacVector, Omega, PCGene, Molecular Simulation, Inc.) can be used to identify proteolytic cleavage sites. Alternatively, such polypeptides may be produced from recombinantly generated full-length ENPP1 and/or ENPP3 polypeptides using chemical cleavage (e.g., cyanogen bromide, hydroxylamine, etc.).

Many expression systems are known can be used for the production of ENPP1 and/or ENPP3 fusion protein, including bacteria (for example *E. coli* and *Bacillus subtilis*), yeasts (for example *Saccharomyces cerevisiae, Kluyveronmyces lactis* and *Pichia* pastorns), filamentous fungi (for example *Aspergillus*), plant cells, animal cells and insect cells. The desired protein can be produced in conventional ways, for example from a coding sequence inserted in the host chromosome or on a free plasmid.

The yeasts can be transformed with a coding sequence for the desired protein in any of the usual ways (e.g., electroporation). Methods for transformation of yeast by electroporation are disclosed in Becker & Guarente, 1990, Methods Enzymol. 194: 182. Successfully transformed cells, i.e., cells that contain a DNA construct of the present disclosure, can be identified by well-known techniques. For example, cells resulting from the introduction of an expression construct can be grown to produce an ENPP1 and/or ENPP3 polypeptide. Cells can be harvested and lysed and their DNA content examined for the presence of the DNA using a method, such as that described by Southern, 1975, J. Mol. Biol, 98:503 and/or Berent, et al., 1985, Biotech 3:208. Alternatively, the presence of the protein in the supernatant can be detected using antibodies.

Useful yeast plasmid vectors include pRS403-406 and pRS413-416 and are generally available front Stratigene Cloning Systems. La Jolla, CA, USA Plasmids pRS403, pRS404, pRS405 and pRS406 are Yeast Integrating plasmids (Yips) and incorporate the yeast selectable markers I-11 S3, TRP1, LEU2 and 1JRA3. Plasmids pRS413-416 are Yeast Centromere plasmids (YCps).

A variety of methods have been developed to operably link DNA to vectors via complementary cohesive termini. For instance, complementary homopolymer tract can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion, is treated with bacteriophage T4 DNA polymerase or *E. coli* DNA polymerase I, which are enzymes that remove protruding, 3'-single-stranded termini with their 3'-5'-exonucleolytic activities, and fill in recessed 3'-ends with their polymerizing activities.

The combination of these activities thus generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. As a result, the products of the reaction are DNA segments carrying polymeric linker sequences at their ends. These DNA segments can be cleaved with an appropriate restriction enzyme and ligated to an expression vector that has been cleaved with an enzyme that produces termini compatible with those of the DNA segment.

Clones of single, stably transfected cells are then established and screened for high expressing clones of the desired ENPP1 and/or ENPP3 fusion protein. Screening of the single cell clones for ENPP1 and/or ENPP3 protein expression can be accomplished in a high-throughput manner in 96 well plates using the synthetic enzymatic substrate pNP-TMP as previously described (Albright, et al., 2015, Nat. Commun. 6.10006). Upon identification of high expressing clones through screening, protein production can be accomplished in shaking flasks or bio-reactors are previously described in Albright et al., 2015, Nat. Commun. 6:10006.

Purification of ENPP1 and/or ENPP3 can be accomplished using a combination of standard purification techniques known in the art. Following purification, ENPP1-Fc and/or ENPP3-Fc can be dialyzed into PBS supplemented with $Zn^{2+}$ and $Mg^{2+}$ (PBSplus) concentrated to between 5 and 7 mg/ml, and frozen at −80° C. in aliquots of 200-500 pl. Aliquots can be thawed immediately prior to use and the specific activity of the solution can be adjusted to 31.25 au/ml (or about 0.7 mg/ml depending on the preparation) by dilution in PBSplus.

3. Nucleic Acids Encoding ENPP1 and/or ENPP3 Polypeptides

In certain embodiments, the present disclosure provides isolated and/or recombinant nucleic acids encoding ENPP1 and/or ENPP3 polypeptides (including fragments, functional variants, and/or fusion proteins thereof). The subject nucleic acids may be single-stranded or double-stranded. Such nucleic acids may be DNA or RNA molecules. These nucleic acids may be used, for example, in methods for generating soluble ENPP1 and/or ENPP3 polypeptides as described herein.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding ENPP1 polypeptides of the disclosure are understood to include nucleic acids that are variants of SEQ ID NO: 14 or SEQ ID NO: 15. Variant nucleotide sequences include sequences that differ by one or more nucleotide substitutions, additions, or deletions including allelic vanants, and therefore, will include coding sequence that differ from the nucleotide sequence designated in SEQ ID NO: 14 or SEQ ID NO: 15.

In certain embodiments, ENPP1 polypeptides of the disclosure are encoded by isolated and/or recombinant nucleic acid sequences that are at least 70%, 75%, 80%, 85%, 90%, 91%, 92%, 93%, 94% 95%, 96%, 97%, 98%, 99%, or 100% identical to SEQ ID NO: 14 or SEQ ID NO: 15. One of ordinary skill in the art will appreciate that nucleic acid sequences that are at least 70%, 75%, 80%, 85%, 90%, 91%, 92%, 93%, 94% 95%, 96%, 97%, 98%, 99%, or 100% identical to the sequences complementary to SEQ ID NO: 14 or SEQ ID NO; 15, and variants thereof, are also within the scope of the present disclosure. In further embodiments, the nucleic acid sequences of the disclosure can be isolated, recombinant, and/or fused with a heterologous nucleotide sequence, or in a DNA library.

In other embodiments, nucleic acids of the present disclosure also include nucleotide sequences that hybridize under highly stringent conditions to the nucleotide sequence designated in SEQ ID NO: 14 or SEQ ID NO: 15, complement sequences of SEQ ID NO: 14 or SEQ ID NO: 15, and/or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NO: 14 or SEQ ID NO: 15 to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the present disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art and can be used in a variety of host cells. Typically, one or more regulatory nucleotide sequences may include, but are not limited to, promoter sequences, leader or signal sequences, ribosomal binding sites, transcriptional start and termination sequences, translational start and termination sequences, and/or enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and can vary with the host cell used.

In certain aspects, the subject nucleic acid disclosed herein is provided in an expression vector comprising a nucleotide sequence encoding an ENPP1 and/or ENPP3 polypeptide and operably linked to at least one regulatory sequence. Regulatory sequences are art-recognized and are selected to direct expression of the ENPP1 and/or ENPP3 polypeptide. Accordingly, the term regulatory sequence includes promoters, enhancers, and other expression control elements. Exemplary regulatory sequences are described in Goeddel; *Gene Expression Technology: Methods in Enzymology*, Academic Press. San Diego, CA (1990). For instance, any of a wide variety of expression control sequences that control the expression of a DNA sequence when operatively linked to it may be used in these vectors to express DNA sequences encoding an ENPP1 and/or ENPP3 polypeptide. Such useful expression control sequences, include, for example, the early and late promoters of SV40, tet promoter, adenovirus or cytomegalovirus immediate early promoter, RSV promoters, the lac system, the trp system, the TAC or TRC system. T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ENPP1 and/or ENPP3 polypeptide include plasmids and other vectors (e.g., virus). For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, e.g., Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In some embodiments, a vector will be designed for production of the subject ENPP1 and/or ENPP3 polypeptides in CHO cells, such as a Pcmv-Script vector (Stratagene, La Jolla. Calif.), pcDNA4 vectors (Invitrogen, Carlsbad. Calif.) and pCI-neo vectors (Promega, Madison, Wisc.). As will be apparent, the subject gene constructs can be used to cause expression of the subject ENPP1 and/or ENPP3 polypeptides in cells propagated in culture, e.g., to produce proteins, including fusion proteins or variant proteins, for purification. In some embodiments, the vector further comprises at least one nucleic acid sequence that directs and/or controls expression of the ENPP1 and/or ENPP3 polypeptide. In some embodiments, the recombinant nucleic acid encodes a polypeptide comprising an ENPP1 and/or ENPP3 polypeptide disclosed herein fused to a signal peptide, wherein the polypeptide is proteolytically processed upon secretion from a cell to yield the soluble ENPP1 and/or ENPP3 polypeptide disclosed herein.

Various viral vectors which can be utilized for gene therapy can comprise a soluble ENPP1 and/or ENPP3 polypeptide sequence as disclosed herein. Certain modified viruses are often used as vectors to carry a coding sequence because after administration to a mammal, a virus infects a cell and expresses the encoded protein. Modified viruses useful according to the invention are derived from viruses which include, for example: parvovirus, picomavirus, pseudorabies virus, hepatitis virus A, B or C, papillomavirus, papovavirus (such as polyoma and SV40) or herpes virus (such as Epstein-Barr Virus, Varicella Zoster Virus, Cytomegalovirus, Herpes Zoster and Herpes Simplex Virus types 1 and 2), an RNA virus or a retrovirus, such as the Moloney murine leukemia virus or a lentivirus (i.e., derived from Human Immunodeficiency Virus, Feline Immunodeficiency Virus, or equine infectious anemia virus). Among DNA viruses useful according to the invention are: Adeno-associated viruses adenoviruses, Alphaviruses, and Lentiviruses.

A viral vector is generally administered by injection, most often intravenously (by IV) directly into the body, or directly into a specific tissue, where it is taken up by individual cells. Alternately, a viral vector may be administered by contacting the viral vector ex vivo with a sample of the patient's cells, thereby allowing the viral vector to infect the cells, and cells containing the vector are then returned to the patient. Once the viral vector is delivered, the coding sequence expressed and results in a functioning protein. Generally, the infection and transduction of cells by viral vectors occur by a series of sequential events as follows: interaction of the viral capsid with receptors on the surface of the target cell, internalization by endocytosis, intracellular trafficking through the endocytic/proteasomal compartment, endosomal escape, nuclear import, virion uncoating, and viral DNA double-strand conversion that leads to the transcription and expression of the recombinant coding sequence interest. (Colella et al., *Mol Ther Methods Clin Dev.* 2017 Dec. 1:8:87-104.).

Adeno-associated viral vectors (AAV) refers to viruses belonging to the genus Dependovirus of the Parvoviridae family. The AAV genome is approximately 4.7 kilobases long and is composed of linear single-stranded deoxyribonucleic acid (ssDNA) which may be either positive- or negative-sensed. The genome comprises inverted terminal repeats (ITRs) at both ends of the DNA strand, and two open reading frames (ORFs): rep and cap. The rep frame is made of four overlapping genes encoding non-structural replication (Rep) proteins required for the AAV life cycle. The cap frame contains overlapping nucleotide sequences of structural VP capsid proteins: VP1, VP2 and VP3, which interact together to form a capsid of an icosahedral symmetry.

The terminal 145 nucleotides are self-complementary and are organized so that an energetically stable intramolecular duplex forming a T-shaped hairpin may be formed. These hairpin structures function as an origin for viral DNA replication, serving as pnmers for the cellular DNA polymerase complex. Following wild type AAV infection in mammalian cells the rep genes (i.e., Rep78 and Rep52) are expressed from the P5 promoter and the P19 promoter, respectively, and both Rep proteins have a function in the replication of the viral genome. A splicing event in the rep ORF results in the expression of actually four Rep proteins (i.e., Rep78, Rep68. Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

The AAV vector typically lacks rep and cap frames. Such AAV vectors can be replicated and packaged into infectious viral particles when present in a host cell that has been transfected with a vector encoding and expressing rep and cap gene products (i.e., AAV Rep and Cap proteins), and wherein the host cell has been transfected with a vector which encodes and expresses a protein from the adenovirus open reading frame E4orf6.

In one embodiment, the invention relates to an AAV expression vector comprising a sequence encoding a soluble ENPP1 and/or ENPP3 polypeptide, and upon administration to a mammal the vector expresses the soluble ENPP1 and/or ENPP3 polypeptide precursor in a cell, the precursor including an Azurocidin signal peptide fused at its carboxy terminus to the amino terminus of the soluble ENPP1 polypeptide. The soluble ENPP1 and/or ENPP3 polypeptide precursor may include a stabilizing domain, such as an IgG Fc region or human albumin. Upon secretion of the precursor from the cell, the signal peptide is cleaved off and enzymatically active soluble ENPP1 and/or ENPP3 polypeptide is provided extracellularly.

An AAV expression vector may include an expression cassette comprising a transcriptional regulatory region operatively linked to a nucleotide sequence comprising a transcriptional regulatory region operatively linked to a recombinant nucleic acid sequence encoding a polypeptide comprising a Azurocidin signal peptide sequence and a soluble ENPP1 polypeptide sequence.

In some embodiments, the expression cassette comprises a promoter and enhancer, the Kozak sequence GCCAC-CATGG (SEQ ID NO: 131), a nucleotide sequence encoding a soluble ENPP1 and/or ENPP3 polypeptide, other suitable regulatory elements and a polyadenylation signal.

In some embodiments, the AAV recombinant genome of the AAV vector according to the invention lacks the rep open reading frame and/or the cap open reading frame.

The AAV vector according to the invention comprises a capsid from any serotype. In general, the AAV serotypes have genomic sequences of significant homology at the amino acid and the nucleic acid levels, provide an identical set of genetic functions, and replicate and assemble through practically identical mechanisms. In particular, the AAV of the present invention may belong to the serotype 1 of AAV (AAV1), AAV2, AAV3 (including types 3A and 3B), AAV4, AAV5, AAV6, AAV7, AAV8, AAV9, AAV10, AAVrh10, AAV11, avian AAV, bovine AAV, canine AAV, equine AAV, or ovine AAV.

Examples of the sequences of the genome of the different AAV serotypes may be found in the literature or in public databases such as GenBank. For example, GenBank accession numbers NC_001401.2 (AAV2), NC_001829.1 (AAV4), NC_006152.1 (AAV5), AF028704.1 (AAV6), NC_006260.1 (AAV7), NC_006261.1 (AAV8), AX753250.1 (AAV9) and AX753362.1 (AAV10).

In some embodiments, the adeno-associated viral vector according to the invention comprises a capsid derived from a serotype selected from the group consisting of the AAV2, AAV5. AAV7, AAV8, AAV9, AAV10 and AAVrh10 serotypes. In another embodiment, the serotype of the AAV is AAV8. If the viral vector comprises sequences encoding the capsid proteins, these may be modified so as to comprise an exogenous sequence to direct the AAV to a particular cell type or types, or to increase the efficiency of delivery of the targeted vector to a cell, or to facilitate purification or detection of the AAV, or to reduce the host response.

The published application, US 2017/0290926 to Smith et al., the contents of which are incorporated by reference in their entirety herein, describes in detail the process by which AAV vectors are generated, delivered and administered.

In some embodiments, an adenovirus can be utilized for gene therapy as taught herein. Adenovirus can be manipulated such that it encodes and expresses the desired gene product, (e.g., a soluble ENPP1 and/or ENPP3 polypeptide), and at the same time is inactivated in terms of its ability to replicate in a normal lytic viral life cycle. In addition, adenovirus has a natural tropism for airway epithelial. The viruses are able to infect quiescent cells as are found in the airways, offering a major advantage over retroviruses. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Shwartz. A. R. et al. (1974) *Am. Rev. Respir. Dis.* 109:233-238). Finally, adenovirus mediated gene transfer has been demonstrated in a number of instances including transfer of alpha-1-antitrypsin and CFTR to the lungs of cotton rats (Rosen/eld, M. A. el al. (1991) *Science* 252:431-434: Rosenfeld et al., (1992) *Cell* 68:143-155). Furthermore, extensive studies to attempt to establish adenovirus as a causative agent in human cancer were uniformly negative (Green, M. et al. (1979) *Proc. Natl. Acad. Sci. USA* 76:6606).

Pseudo-Adenovirus Vectors (PAV)—PAVs contain adenovirus inverted terminal repeats and the minimal adenovirus 5' sequences required for helper virus dependent replication and packaging of the vector. These vectors contain no potentially harmful viral genes, have a theoretical capacity for foreign material of nearly 36 kb, may be produced in reasonably high titers and maintain the tropism of the parent virus for dividing and non-dividing human target cell types. The PAV vector can be maintained as either a plasmid-bome construct or as an infectious viral particle. As a plasmid construct, PAV is composed of the minimal sequences from wild type adenovirus type 2 necessary for efficient replication and packaging of these sequences and any desired additional exogenous genetic material, by either a wild-type or defective helper virus.

The US patent publication U.S. Pat. No. 7,318,919 to Gregory et al., the contents of which are incorporated by reference in their entirety herein, describes in detail the process by which adenoviral vectors are generated, delivered and their corresponding use for treatment of diseases. The present invention contemplates the use of adenoviral vectors to deliver nucleotides encoding a soluble ENPP1 polypeptide and/or a soluble ENPP3 polypeptide to a subject in need thereof and the methods of treatment using the same.

In some embodiments, a herpes simplex vector (HSV based viral vector) can be utilized for gene therapy as taught herein. A HSV based viral vector is suitable for use as a vector to introduce a nucleic acid sequence into numerous cell types. The mature HSV virion consists of an enveloped icosahedral capsid with a viral genome consisting of a linear double-stranded DNA molecule that is 152 kb. In another embodiment, the HSV based viral vector is deficient in at least one essential HSV gene. In some embodiments, the HSV based viral vector that is deficient in at least one essential HSV gene is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb.

HSV-based vectors are described in, for example, U.S. Pat. No. 5,837,532 to Preston et al., U.S. Pat. No. 5,846,782 to Wickham et al., and U.S. Pat. No. 5,804,413 to Deluca et al., and International Patent Applications WO 91/02788 to Preston et al., WO 96/04394 to Preston et al., WO 98/15637 to Deluca et al., and WO 99/06583 to Glorioso et al., all which are incorporated herein by reference in their entireties. The HSV vector can be deficient in replication-essential gene functions of only the early regions of the HSV genome, only the immediate-early regions of the HSV genome, only the late regions of the HSV genome, or both the early and late regions of the HSV genome. The production of HSV vectors involves using standard molecular biological techniques well known in the art.

Replication deficient HSV vectors are typically produced in complementing cell lines that provide gene functions not present in the replication deficient HSV vectors, but required for viral propagation, at appropriate levels in order to generate high titers of viral vector stock. The expression of the nucleic acid sequence encoding the protein is controlled by a suitable expression control sequence operably linked to the nucleic acid sequence. An "expression control sequence" is any nucleic acid sequence that promotes, enhances, or controls expression (typically and preferably transcription) of another nucleic acid sequence.

Suitable expression control sequences include constitutive promoters, inducible promoters, repressible promoters, and enhancers. The nucleic acid sequence encoding the protein in the vector can be regulated by its endogenous promoter or, preferably, by a non-native promoter sequence. Examples of suitable non-native promoters include the human cytomegalovirus (HCMV) promoters, such as the HCMV immediate-early promoter (HCMV IEp), promoters derived from human immunodeficiency virus (HIV), such as the HIV long terminal repeat promoter, the phosphoglycerate kinase (PGK) promoter, Rous sarcoma virus (RSV) promoters, such as the RSV long terminal repeat, mouse mammary tumor virus (MMTV) promoters, the Lap2 promoter, or the herpes thymidine kinase promoter (Wagner et al., *Proc. Natl. Acad. Sci.* 78, 1444-1445 (1981)), promoters derived from SV40 or Epstein Barr virus, and the like. In another embodiment, the promoter is HCMV IEp.

The promoter can also be an inducible promoter, i.e., a promoter that is up- and/or down-regulated in response to an appropriate signal. For example, an expression control sequence up-regulated by a pharmaceutical agent is particularly useful in pain management applications. For example, the promoter can be a pharmaceutically-inducible promoter (e.g., responsive to tetracycline). The promoter can be introduced into the genome of the vector by methods known in the art, for example, by the introduction of a unique restriction site at a given region of the genome.

The US patent publication, U.S. Pat. No. 7,531,167 to Glorioso et al., the contents of which are incorporated by reference in their entirety herein, describes in detail the process by which Herpes Simplex vectors are generated, delivered and their corresponding use for treatment of diseases. The present invention contemplates the use of Herpes Simplex vectors to deliver nucleotides encoding a soluble ENPP1 and/or ENPP3 polypeptide to a subject in need thereof and the methods of treatment using the same.

In some embodiments, alphaviral expression vectors can be utilized for gene therapy as taught herein. Alphaviral expression vectors have been developed from different types of alphavirus, including Sindbis virus (SIN), Semliki Forest Virus (SFV) and Venezuelan equine encephalitis (VEE) virus. The alphavirus replicon contains at its 5' end an open reading frame encoding viral replicase (Rep) which is translated when viral RNA is transfected into cells. Rep is expressed as a polyprotein which is subsequently processed into four subunits (nsps 1 to 4). Unprocessed Rep can copy the RNA vector into negative-strand RNA, a process that only takes place during the first 3 to 4 hours after transfection or infection. Once processed, the Rep will use the negative-strand RNA as a template for synthesizing more replicon molecules. Processed Rep can also recognize an internal sequence in the negative-strand RNA, or subgenomic promoter, from which it will synthesize a subgenomic positive-strand RNA corresponding to the 3' end of the replicon. This subgenomic RNA will be translated to produce the heterologous protein in large amounts.

A non-cytopathic mutant isolated from SIN containing a single amino acid change (P for L) in position 726 in nsp2 (SIN P726L vector in nsp2) showed Rep hyper processing (Frolov et al., 1999. *J. Virol.* 73: 3854-65). This mutant was capable of efficiently establishing continuous replication in BHK cells. This non-cytopathic SIN vector has been widely used in vitro as it is capable of providing long-lasting transgene expression with good stability levels and expression levels that were about 4% of those obtained with the original SIN vector (Agapov et al., 1998. *Proc. Natl. Acad. Sci. USA.* 95: 12989-94). Likewise, the Patent application WO2008065225—Smerdou et al., describes a non-cytopathic SFV vector has mutations R649H/P718T in the replicase nsp2 subunit. The aforesaid vector allows obtaining cell lines capable of constitutively and stably expressing the gene of interest by means of culturing in the presence of an antibiotic the resistance gene of which is incorporated in the alphaviral vector (Casales et al. 2008. *Virology* 376:242-51).

The invention contemplates designing a vector comprising a DNA sequence complementary to an alphavirus replicon in which a sequence of a gene of interest such as a soluble ENPP1 and/or ENPP3 polypeptide has been incorporated along with recognition sequences for site-specific recombination. By means of said vector, it is possible to obtain and select cells in which the alphaviral replicon, including the sequence of the gene of interest, has been integrated in the cell genome, such that the cells stably express the soluble ENPP1 and/or ENPP3 polypeptide. The invention also contemplates generating an expression vector in which the alphaviral replicon is under the control of an inducible promoter. Said vector when incorporated to cells which have additionally been modified by means of incorporating an expression cassette encoding a transcriptional activator which, in the presence of a given ligand, is capable of positively regulating the activity of the promoter which regulates alphavirus replicon transcription.

The US patent publication, U.S. Pat. No. 10,011,847 to Aranda et al., the contents of which are incorporated by reference in their entirety herein, describes in detail the process by which Alphaviral vectors are generated, delivered and their corresponding use for treatment of diseases. The present invention contemplates the use of Alphaviral vectors to deliver nucleotides encoding a soluble ENPP1 polypeptide to a subject in need thereof and methods of treatment using the same.

In some embodiments, lentivirus vectors can be utilized for gene therapy as taught herein. Lentiviruses belong to a genus of viruses of the Retroviridae family and are characterized by a long incubation period. Lentiviruses can deliver a significant amount of viral RNA into the DNA of the host cell and have the unique ability among retroviruses of being able to infect non-dividing cells. Lentiviral vectors, especially those derived from HIV-1, are widely studied and frequently used vectors. The evolution of the lentiviral vectors backbone and the ability of viruses to deliver recombinant DNA molecules (transgenes) into target cells have led to their use in restoration of functional genes in gene therapy and in in vitro recombinant protein production.

The invention contemplates a lentiviral vector comprising a suitable promoter and a transgene to express protein of interest such as a soluble ENPP1 and/or ENPP3 polypeptide. Typically, the backbone of the vector is from a simian immunodeficiency virus (SIV), such as SIV1 or African green monkey SIV (SIV-AGM). In one embodiment, the promoter is preferably a hybrid human CMV enhancer/EF1a (hCEF) promoter. The present invention encompasses methods of manufacturing lentiviral vectors, compositions comprising lentiviral vectors expressing genes of interest, and use in gene therapy to express a soluble ENPP1 and/or ENPP3 polypeptide in order to treat diseases of calcification or ossification. The lentiviral vectors according to the invention can also be used in methods of gene therapy to promote secretion of therapeutic proteins. By way of further example, the invention provides secretion of therapeutic proteins into the lumen of the respiratory tract or the circulatory system. Thus, administration of a vector according to the invention and its uptake by airway cells may enable the use of the lungs (or nose or airways) as a "factory" to produce a therapeutic protein that is then secreted and enters the general circulation at therapeutic levels, where it can travel to cells/tissues of interest to elicit a therapeutic effect. In contrast to intracellular or membrane proteins, the production of such secreted proteins does not rely on specific disease target cells being transduced, which is a significant advantage and achieves high levels of protein expression. Thus, other diseases which are not respiratory tract diseases, such as cardiovascular diseases and blood disorders can also be treated by the lentiviral vectors. Lentiviral vectors, such as those according to the invention, can integrate into the genome of transduced cells and lead to long-lasting expression, making them suitable for transduction of stem/progenitor cells.

The US patent application publication. US 2017/0096684 to Alton et al., the contents of which are incorporated by reference in their entirety herein, describes in detail the process by which Lentiviral vectors are generated, delivered and their corresponding use for treatment of diseases. The present invention contemplates the use of lentiviral vectors to deliver nucleotides encoding a soluble ENPP1 and/or ENPP3 polypeptide to a subject in need thereof and the methods of treatment using the same.

This disclosure also pertains to a host cell transfected with a recombinant gene or viral vector including a coding sequence for one or more of the subject ENPP1 and/or ENPP3 polypeptides. In some embodiment, the host cell may be any prokaryotic or eukaryotic cell. In certain embodiments, the cell is a non-human cell. In other embodiments, the cell is mammalian. For example, an ENPP1 and/or ENPP3 polypeptide of the disclosure may be expressed in bacterial cells such as *E. coli*, insect cells (e.g., using a baculovirus expression system), yeast, or mammalian cells [e.g. a Chinese hamster ovary (CHO) cell line]. Other suitable host cells are known to those skilled in the art. In some embodiments, the vector comprises a recombinant nucleic acid encoding a polypeptide comprising an ENPP1 and/or ENPP3 polypeptide disclosed herein and a signal peptide. In some embodiments, the polypeptide is proteolytically processed upon secretion from a cell to yield the soluble ENPP1 and/or ENPP3 polypeptide disclosed herein.

Accordingly, the present disclosure further pertains to methods of producing the subject ENPP1 and/or ENPP3 polypeptides. For example, a host cell transfected with an expression vector encoding an ENPP1 and/or ENPP3 polypeptide can be cultured under appropriate conditions to allow expression of the ENPP1 polypeptide and/or ENPP3 to occur. The polypeptide may be secreted and isolated from a mixture of cells and medium containing the polypeptide. Alternatively, the ENPP1 and/or ENPP3 polypeptide may be retained cytoplasmically or in a membrane fraction and the cells harvested and lysed, and the protein isolated. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ENPP1 and/or ENPP3 polypeptides, and/or affinity purification with an agent that binds to a domain fused to the ENPP1 polypeptide (e.g., a column may be used to purify an ENPP1-Fc and/or ENPP3-Fc fusion protein). In some embodiments, the ENPP1 and/or ENPP3 polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. An ENPP1 and/or ENPP3 protein may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant ENPP1 and/or ENPP3 polypeptide, can allow purification of the expressed fusion protein by affinity chromatography using a Ni$^{2+}$ metal resin. The purification leader sequence can then be subsequently removed by treatment with enterokinase to provide the purified ENPP1 and/or ENPP3 polypeptide. &e, e.g., Hochuli et al. (1987) *J. Chromatography* 411:177; and Janknecht et al. (1991) *PNAS USA* 88:8972.

ENPP1, or an ENPP1 polypeptide, can be prepared as described in US 2015/0359858 A1, which is incorporated herein in its entirety by reference. ENPP1 is a transmembrane protein localized to the cell surface with distinct intramembrane domains. In order to express ENPP1 as a soluble extracellular protein, the transmembrane domain of ENPP1 may be swapped for the transmembrane domain of ENPP2, which results in the accumulation of soluble, recombinant ENPP1 in the extracellular fluid of the baculovirus cultures.

Signal sequences of any other known proteins may be used to target the extracellular domain of ENPP1 for secretion as well, such as but not limited to the signal sequence of the immunoglobulin kappa and lambda light chain proteins. Further, the disclosure should not be construed to be limited to the polypeptides described herein, but also includes polypeptides comprising any enzymatically active truncation of the ENPP1 extracellular domain.

ENPP1 can be made soluble by omitting the transmembrane domain. In some embodiments, human ENPP1 (SEQ ID NO:1) can be modified to express a soluble, recombinant protein by replacing its transmembrane region (e.g., residues 77-98) with the corresponding subdomain of human ENPP2 (NCBI accession NP_00112433 5, e.g., residues 12-30). In some embodiments, the modified ENPP1 sequence can be cloned into a modified pFastbac FIT vector possessing a TEV protease cleavage site followed by a C-terminus 9-F11S tag, and cloned and expressed in insect cells. In some embodiments, both proteins can be expressed in a baculovirus system as described previously (Albright, et al., 2012, Blood 120:4432-4440: Saunders, et al., 2011, J. Biol. Chem. 18:994-1004; Saunders, et al., 2008, Mol. Cancer Ther. 7:3352-3362), resulting in the accumulation of soluble, recombinant protein in the extracellular fluid.

Techniques for generating fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

4. Exemplary Uses

In certain aspects, the present disclosure relates to the use of certain soluble ENPP1 polypeptides (e.g., and fusion proteins thereof) for reducing, reversing, and/or preventing progression of pathological calcification in a subject in need thereof, the method comprising administering to the subject a therapeutically effective amount of the polypeptide fusion and/or the soluble polypeptide disclosed herein (e.g., SEQ ID NOs: 2, 3, 9, 10, 11, and 12). In certain embodiments, the pathological calcification is selected from the group consisting of idiopathic infantile arterial calcification (IIAC) and calcification of atherosclerotic plaques. In certain embodiments, the pathological ossification is selected from the group consisting of ossification of the posterior longitudinal ligament (OPLL), hypophosphatemic rickets, and osteoarthritis.

In some embodiments, the disclosure contemplates methods of reducing, reversing, and/or preventing progression of pathological ossification in a subject in need thereof, the method comprising administering to the subject a therapeutically effective amount of a soluble ENPP1 polypeptide and/or ENPP1 fusion poly peptide disclosed herein (e.g., SEQ ID NOs: 2, 3, 9, 10, 11, and 12).

In some embodiments, the disclosure contemplates methods of reducing, reversing, and/or preventing progression of ectopic calcification of soft tissue, including reducing, ameliorating, or preventing vascular calcification, in a subject in need thereof, the method comprising administering to the subject a therapeutically effective amount of a soluble ENPP1 polypeptide and/or ENPP1 fusion polypeptide disclosed herein.

In some embodiments, the disclosure contemplates methods of reducing, reversing, and/or preventing progression of diseases caused by an ENPP1 deficiency (e.g., GACI and ARHR2). ENPP1 deficiency is characterized by reduced levels of ENPP1 activity and/or defective expression of ENPP1 levels (compared to that of ENPP1 activity levels or ENPP1 expression levels respectively in normal healthy subjects) in a subject in need thereof, the method comprising administering to the subject a therapeutically effective amount of a soluble ENPP1 polypeptide and/or ENPP1 fusion protein disclosed herein (e.g. SEQ ID NOs: 2, 3, 9, 10, 11, and 12). In some embodiments, the ENPP1 deficiency is GACI. In some embodiments, the ENPP1 deficiency is ARHR2.

In some embodiments, the disclosure contemplates methods of reducing, reversing, and/or preventing progression of diseases caused by lower levels of plasma PPi in a subject in need thereof, the method comprising administering to the subject a therapeutically effective amount of the polypeptides disclosed herein to increase the plasma PPi of the subjects to normal (1-3 pM) or above (30-50% higher than) normal levels and then to maintain the plasma PPi at a constant normal or above normal level thereafter. The method further comprises administering additional therapeutic effective amounts at intervals of two days, three days, one week or one month in order to maintain the plasma PPi of the subject at a constant normal or above normal level to reduce, reverse, and/or prevent the progression of pathological calcification or ossification. In certain embodiments, a soluble ENPP1 polypeptide or ENPP1 fusion polypeptide disclosed herein can be used to raise pyrophosphate (PPi) levels in a subject having PPi level lower than normal level (which is around 2 pM). In other embodiments, a soluble ENPP1 polypeptide or ENPP1 fusion polypeptide disclosed herein can be used to reduce, reverse, and/or prevent progression of pathological calcification or ossification in a subject having PPi levels lower than normal level. In some embodiments, a soluble ENPP1 polypeptide or ENPP1 fusion polypeptide disclosed herein can be used to treat and/or ameliorate ENPP1 deficiency (e.g., GACI and ARHR2) manifested by a reduction of extracellular PPi concentration in a subject. In certain embodiments, the steady state level of plasma PPi achieved after administration of a first dosage of a soluble ENPP1 polypeptide or ENPP1 fusion polypeptide disclosed herein is maintained for a time period of at least 2 days, at least 4 days, at least a week or at least a month.

In some embodiments, the disclosure contemplates methods of reducing, reversing, and/or preventing progression of a disease caused by lower than normal levels of plasma PPi in a subject in need thereof, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12) to increase and/or sustain the plasma PPi of the subjects to a level that is about 90%, 95%, 100%, 105%, 110/%, 120%, 130%, 140%, or 150% of the normal PPi level (about 1-3 pM). In certain embodiments, the method further comprises further administration of the polypeptide disclosed herein every two days, three days, one week, or one month in order to maintain the plasma PPi levels at a level that is about 90%, 95%, 100%, 105%, 110%, 120%, 130%, 140%, or 150% of the normal PPi level, thus reducing, reversing, and/or preventing the progression of pathological calcification or ossification.

In certain embodiments, a second dosage of a soluble ENPP1 polypeptide or ENPP1 fusion polypeptide disclosed herein is administered after a suitable time interval of about after two days, after four days, after a week, or after a month to the subject so that the steady state level of plasma PPi is maintained at a constant or steady state level and does not return to the lower level of PPi that the subject had prior to the administration of first dosage of constructs disclosed herein.

Without wishing to be bound be theory, it is believed that maintaining a steady state concentration of plasma PPi at normal levels reduces, reverses, and/or prevents progression of pathological calcification and pathological ossification of subjects.

In some embodiments, the disclosure contemplates methods of treating, reversing, and/or preventing progression of ossification of the posterior longitudinal ligament (OPLL) in a subject in need thereof, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12).

In some embodiments, the disclosure contemplates methods of treating, reversing, and/or preventing progression of hypophosphatemic rickets in a subject in need thereof, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12).

In some embodiments, a soluble ENPP1 polypeptide of the disclosure treats, ameliorates, and/or prevents human or animal disorders or conditions such as, but not limited to, ectopic calcification (e.g., soft tissue calcification, arterial calcification, and vascular calcification), chronic kidney disease (CKD), end stage renal disease (ESRD), calcific uremic arteriolopathy (CUA), calciphylaxis, ossification of the posterior longitudinal ligament (OPLL), hypophosphatemic rickets, osteoarthritis, aging related hardening of arteries, idiopathic infantile arterial calcification (IIAC), calcification of atherosclerotic plaques, ENPP1 deficiencies [e.g., autosomal recessive hypophosphatemic rickets type 2 (ARHR2) and Generalized Arterial Calcification of Infancy (GACI)], pseudoxanthoma elasticum (PXE), disorders associated with a pathogenic mutation in ABCC6 gene, and pathological ossification. Examples of ENPP1 polypeptides include human ENPP1 precursor polypeptide (e.g., SEQ ID NO: 1), and/or soluble human ENPP1 polypeptides (e.g., SEQ ID NOs: 2, 3, 9, 10, 11, and 12).

In certain embodiments, the soft tissue calcification is selected from the group consisting of IIAC and osteoarthritis. In other embodiments, the soft tissue comprises atherosclerotic plaques. In some embodiments, the soft tissue comprises muscular arteries. In some embodiments, the soft tissue is selected from the group consisting of joint and spine. In some embodiments, the joint is selected from the group consisting of joints of the hands and joints of the feet.

In some embodiments, the soft tissue is selected from the group consisting of articular cartilage and vertebral disk cartilage. In some embodiments, the soft tissue comprises vessels. In some embodiments, the soft tissue comprises connective tissue.

In some embodiments, the disclosure contemplates methods of treating, reversing, and/or preventing progression of Pseudoxanthoma Elasticum (PXE) in a subject in need thereof, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12).

In some embodiments, the disclosure contemplates methods of reducing, reversing, and/or preventing progression of age-related hardening of arteries in a subject in need thereof, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12).

In some embodiments, the disclosure contemplates methods of treating, reversing, and/or preventing progression of calcification of atherosclerotic plaques in vascular arteries in a subject in need thereof, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12).

In some embodiments, the disclosure contemplates methods of treating, reversing, and/or preventing progression of osteoarthritis in a subject in need thereof, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12).

In some embodiments, the disclosure contemplates methods of treating, reversing, and/or preventing progression of hardening of arteries due to progeria in a subject in need thereof, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12).

In some embodiments, the disclosure contemplates methods of treating, reversing, and/or preventing progression of X-linked hypophosphatemic rickets (XLH), hereditary hypophosphatemic rickets (HHRH), hypophosphatemic bone disease (HBD), autosomal dominant hypophosphatemic rickets (ADHR), and/or and autosomal recessive hypophosphatemic rickets in a subject in need thereof, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12).

In some embodiments, the disclosure contemplates methods of treating, reversing, and/or preventing progression of age-related osteopenia in a subject in need thereof, the method comprising administering to the subject a therapeutically effective amount of a soluble ENPP1 polypeptide or ENPP1 fusion polypeptide disclosed herein (e.g., SEQ ID NOs: 2, 3, 9, 10, 11, and 12).

In some embodiments, the disclosure contemplates methods of treating, reversing, and/or preventing progression of ankylosing spondylitis in a subject in need thereof, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12).

In some embodiments, the disclosure contemplates methods of treating, reversing, and/or preventing progression of strokes in pediatric sickle cell anemia in a subject in need thereof, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12).

In certain embodiments, the disclosure contemplates methods of treating, reversing, and/or preventing progression of disease in a subject diagnosed with progeria, the method comprising administering to the subject a therapeutically effective amount of a soluble ENPP1 polypeptide and/or ENPP1 fusion polypeptide disclosed herein (e.g., SEQ ID NOs: 2, 3, 9, 10, 11, and 12).

In some embodiments, the disclosure features a polypeptide or a fusion protein, or pharmaceutical compositions comprising a polypeptide or fusion protein, comprising the amino acid sequence depicted in SEQ ID NO: 9. In some embodiments, the disclosure features a polypeptide or a fusion protein, or pharmaceutical compositions comprising a polypeptide or fusion protein, comprising the amino acid sequence depicted in SEQ ID NO: 10, with or without the underlined signal sequence. In some embodiments, the disclosure features a polypeptide or a fusion protein, or pharmaceutical compositions comprising a polypeptide or fusion protein, comprising the amino acid sequence depicted in SEQ ID NO: 11. In some embodiments, the disclosure features a polypeptide or a fusion protein, or pharmaceutical compositions comprising a polypeptide or fusion protein, comprising the amino acid sequence depicted in SEQ ID NO: 12, with or without the underlined signal sequence. In some embodiments, the disclosure features a polypeptide or a fusion protein, or pharmaceutical compositions comprising a polypeptide or fusion protein, comprising the amino acid sequence depicted in SEQ ID NO: 121. In some embodiments, the disclosure features a polypeptide or a fusion protein, or pharmaceutical compositions comprising a polypeptide or fusion protein, comprising the amino acid sequence depicted in SEQ ID NO: 122. In some embodiments, the disclosure features a polypeptide or a fusion protein, or pharmaceutical compositions comprising a polypeptide or fusion protein, comprising the amino acid sequence depicted in SEQ ID NO: 127, with or without the underlined signal sequence. In some embodiments, the disclosure features a polypeptide or a fusion protein, or pharmaceutical compositions comprising a polypeptide or fusion protein, comprising the amino acid sequence depicted in SEQ ID NO: 128, with or without the underlined signal sequence.

In certain embodiments, the polypeptide is a secreted product of a ENPP1 precursor protein expressed in a mammalian cell. In other embodiments, the ENPP1 precursor protein comprises a signal peptide sequence and an ENPP1 polypeptide, wherein the ENPP1 precursor protein undergoes proteolytic processing to the polypeptide disclosed herein. In some embodiments, in the ENPP1 precursor protein the signal peptide sequence is conjugated to the ENPP1 polypeptide N-terminus. Upon proteolysis, the signal sequence is cleaved from the ENPP1 precursor protein to provide the ENPP1 polypeptide. In certain embodiments, the signal peptide sequence is selected from the group consisting of ENPP1 signal peptide sequence, ENPP2 signal peptide sequence, ENPP7 signal peptide sequence, and ENPP5 signal peptide sequence.

In certain embodiments, the polypeptide is administered acutely or chronically to the subject. In other embodiments, the polypeptide is administered locally, regionally, parenterally or systemically to the subject.

In certain embodiments, the subject is a mammal. In other embodiments, the mammal is human.

It will be appreciated by one of skill in the art, when armed with the present disclosure including the methods detailed herein, that the disclosure is not limited to treatment of a disease and/or disorder once it is established. Particularly, the symptoms of the disease or disorder need not have manifested to the point of detriment to the subject: indeed, the disease or disorder need not be detected in a subject before treatment is administered. That is, significant pathology from disease or disorder does not have to occur before the present ENPP1 and/or ENPP3 polypeptides may provide benefit.

In certain aspects, the disclosure relates to methods for preventing diseases and disorders in a subject, in that a soluble ENPP1 and/or ENPP3 polypeptide, and/or ENPP1 and/or ENPP3 fusion polypeptide, disclosed herein can be administered to a subject prior to the onset of the disease or disorder, thereby preventing the disease or disorder from developing. Therefore, the disclosure relates to methods for preventing or delaying onset, or reducing progression or growth, of a disease or disorder in a subject, comprising administering an ENPP1 and/or ENPP3 polypeptide to a subject prior to detection of the disease or disorder. In certain embodiments, the ENPP1 and/or ENPP3 polypeptide is administered to a subject with a strong family history of the disease or disorder, thereby preventing or delaying onset or progression of the disease or disorder.

Armed with the disclosure herein, one skilled in the art would thus appreciate that the prevention of a disease or disorder in a subject encompasses administering to a subject an ENPP1 and/or ENPP3 polypeptide as a preventative measure against the disease or disorder.

5. Pharmaceutical Compositions

The soluble ENPP1 and/or ENPP3 polypeptides and fusion proteins thereof as described herein may be formulated into pharmaceutical compositions. Pharmaceutical compositions for use in accordance with the present disclosure may be formulated in any conventional manner using one or more physiologically acceptable carriers or excipients. Such formulations are substantially pyrogen-free, in compliance with most regulatory requirements. Such a pharmaceutical composition may be in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

It is understood that the dosage regimen may be determined by the attending physician considering various factors which modify the action of the subject compounds of the disclosure (e.g., soluble ENPP1 and/or ENPP3 polypeptides). The various factors include, but are not limited to, the patient's age, sex, and diet, the severity disease, time of administration, and other clinical factors. Optionally, the dosage may vary with the type of matrix used in the reconstitution and the types of compounds in the composition.

In certain embodiments, pharmaceutical compositions disclosed herein may be administered to deliver a dose of between 1 ng/kg/day and 100 mg/kg/day. In other embodiments, the pharmaceutical compositions disclosed herein may be administered to deliver a dose of between 1 ng/kg/day and 500 mg/kg/day.

The relative amounts of the active ingredient (e.g., soluble ENPP1 and/or ENPP3 polypeptides and fusion proteins thereof), the pharmaceutically acceptable carrier, and any additional ingredients in a pharmaceutical composition disclosed herein will vary, depending upon the identity, size, and condition of the subject treated and further depending upon the route by which the composition is to be administered. By way of example, the composition may comprise between about 0.1% and about 100% (w/w) active ingredient.

As used herein, a "unit dose" is a discrete amount of the pharmaceutical composition comprising a predetermined amount of the active ingredient (e.g., soluble ENPP1 and/or ENPP3 polypeptides and fusion proteins thereof). The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

The regimen of administration may affect what constitutes an effective amount. For example, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation. In certain embodiments, administration of the compound disclosed herein to a subject elevates the subject's plasma PPi to a level that is close to normal, where a normal level of PPi in mammals is 1-3 pM. "Close to normal" refers to 0 to 1.2 pM or 0-40% below or above normal, 30 nM to 0.9 pM or 1-30% below or above normal, 0 to 0.6 pM or 0-20% below or above normal, or 0 to 0.3 pM or 0-10% below or above normal.

Administration of the compositions of the present disclosure (e.g., soluble ENPP1 and/or ENPP3 polypeptides and fusion proteins thereof) to a patient, such as a mammal (i.e., a human), may be carried out using known procedures, at dosages and for periods of time effective to treat a disease or disorder in the patient. An effective amount of the therapeutic compound necessary to achieve a therapeutic effect may vary according to factors such as the activity of the particular compound employed; the time of administration: the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. Dosage is determined based on the biological activity of the therapeutic compound which in turn depends on the half-life and the area under the plasma time of the therapeutic compound curve. The polypeptide according to the disclosure is administered at an appropriate time interval of every 2 days, or every 4 days, or every week or every month so as to achieve a continuous level of plasma PPi that is either close to the normal (1-3 pM) level or above (30-50% higher than) normal levels of PPi. Therapeutic dosage of the ENPP1 and/or ENPP3 polypeptides may also be determined based on half-life or the rate at which the therapeutic polypeptide is cleared out of the body. The polypeptide according to the disclosure is administered at appropriate time intervals of either every 2 days, or every 4 days, every week or every month so as to achieve a constant level of enzymatic activity of ENPP1 and/or ENPP3.

For example, several divided doses may be administered daily or the dose may be proportionally reduced as indicated by the exigencies of the therapeutic situation. A non-limiting example of an effective dose range for a therapeutic compound disclosed herein is from about 0.01 and 50 mg/kg of body weight/per day. In some embodiments, the effective dose range for a therapeutic compound disclosed herein is from about 50 ng to 500 ng/kg, preferably 100 ng to 300 ng/kg of body weight. One of ordinary skill in the art would be able to study the relevant factors and make the determination regarding the effective amount of the therapeutic compound without undue experimentation.

The soluble ENPP1 and/or ENPP3 polypeptides and fusion proteins thereof may be administered to an patient as frequently as several times daily, or it may be administered less frequently, such as once a day, once a week, once every two weeks, once a month, or even less frequently, such as once every several months or even once a year or less. It is understood that the amount of soluble ENPP1 and/or ENPP3 polypeptides and fusion proteins thereof dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the patient.

Actual dosage levels of the active ingredients (e.g., soluble ENPP1 and/or ENPP3 polypeptides and/or fusion proteins thereof) in the pharmaceutical compositions of this disclosure may be varied so as to obtain an amount of the active ingredient that is effective to achieve the desired therapeutic response for a particular patient, composition, and mode of administration, without being toxic to the patient.

A medical doctor, e.g. physician, having ordinary skill in the art may readily determine and prescribe the effective amount of the pharmaceutical composition required. For example, the physician or veterinarian could start doses of the compounds disclosed herein employed in the pharmaceutical composition at levels lower than that required in order to achieve the desired therapeutic effect and gradually increase the dosage until the desired effect is achieved.

In certain embodiments, the compositions disclosed herein are administered to the patient in dosages that range from one to five times per day or more. In other embodiments, the compositions disclosed herein are administered to the patient in range of dosages that include, but are not limited to, once every day, every two, days, every three days to once a week, and once every two weeks. The frequency of administration of the various combination compositions disclosed herein varies from subject to subject depending on many factors including, but not limited to, age, disease or disorder to be treated, gender, overall health, and other factors. Thus, the disclosure should not be construed to be limited to any particular dosage regime and the precise dosage and composition to be administered to any patient will be determined by the attending physical taking all other factors about the patient into account.

In certain embodiments, the present disclosure is directed to a packaged pharmaceutical composition comprising a container holding a therapeutically effective amount of a compound disclosed herein, alone or in combination with a second pharmaceutical agent; and instructions for using the compound to treat, prevent, or reduce one or more symptoms of a disease or disorder in a patient.

Routes of administration of any of the compositions disclosed herein include inhalational, oral, nasal, rectal, parenteral, sublingual, transdermal, transmucosal (e.g., sublingual, lingual, (trans)buccal, (trans)urethral, vaginal (e.g., trans- and perivaginally), intranasal, and (trans)rectal, intravesical, intrapulmonary, intraduodenal, intragastrical, intrathecal, subcutaneous, intramuscular, intradermal, intraarterial, intravenous, intrabronchial, inhalation (e.g., aerosol), ophthalmic, pulmonary, and topical administration. In other embodiments, the polypeptide, or its precursor protein, is administered to the subject as a pharmaceutical composition further comprising at least one pharmaceutically acceptable carrier.

In certain embodiments, the polypeptide, or its precursor protein, is administered acutely or chronically to the subject. In other embodiments, the polypeptide, or its precursor protein, is administered locally, regionally or systemically to the subject. In yet another embodiment, the polypeptide, or its precursor protein, is delivered on an encoded vector, wherein the vector encodes the protein and it is transcribed and translated from the vector upon administration of the vector to the subject.

In certain embodiments, the therapeutic methods of the disclosure include administering the composition systemically, or locally as an implant or device. In some embodiments, pharmaceutical compositions that are useful in the methods disclosed herein may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, and immunologically-based formulations. When administered, the therapeutic composition for use in this disclosure is in a substantially pyrogen-free, or pyrogen-free, physiologically acceptable form.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. The formulations and compositions that would be useful in the present disclosure are not limited to the particular formulations and compositions that are described herein.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Pharmaceutical compositions suitable for parenteral administration may comprise one or more ENPP1 polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

In some embodiments, the disclosure provides a kit comprising at least one soluble ENPP1 and/or ENPP3 polypeptide disclosed herein, or a salt or solvate thereof, and instructions for using the soluble ENPP1 and/or ENPP3 polypeptide within the methods disclosed herein.

Further, the composition may be encapsulated or injected in a form for delivery to a target tissue site. In certain embodiments, compositions of the present disclosure may include a matrix capable of delivering one or more therapeutic compounds (e.g., ENPP1 and/or ENPP3 polypeptides) to a target tissue site, providing a structure for the developing tissue and optimally capable of being resorbed into the body. For example, the matrix may provide slow release of the ENPP1 and/or ENPP3 polypeptide. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

In certain embodiments, therapeutic agents disclosed herein can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid: (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds: (7) wetting agents, such as, for example, cetyl alcohol and glycerol monostearate: (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

In certain embodiments, the soluble ENPP1 and/or ENPP3 polypeptide or fusion protein thereof is formulated as a liquid formulation. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In certain embodiments, the soluble ENPP1 and/or ENPP3 polypeptide is formulated as a lyophilized product. In other embodiments, the disclosure provides a dry product form of a pharmaceutical composition comprising a therapeutic amount of a soluble ENPP1 and/or ENPP3 polypeptide disclosed herein, whereby the dry product is reconstitutable to a solution of the compound in liquid form.

Additional dosage forms of this disclosure include dosage forms as described in U.S. Pat. Nos. 6,340,475, 6,488,962, 6,451,808, 5,972,389, 5,582,837, and 5,007,790. Additional dosage forms of this disclosure also include dosage forms as described in U.S. Patent Applications Nos. 20030147952, 20030104062, 20030104053, 20030044466, 20030039688, and 20020051820. Additional dosage forms of this disclosure also include dosage forms as described in PCT Applications Nos. WO 03/35041, WO 03/35040, WO 03/35029, WO 03/35177. WO 03/35039, WO 02/96404. WO 02/32416, WO 01/97783, WO 01/56544, WO 01/32217. WO 98/55107, WO 98/11879, WO 97/47285, WO 93/18755, and WO 90/11757.

The compositions disclosed herein may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Controlled- or sustained-release formulations of a pharmaceutical composition disclosed herein may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Single unit dosage forms suitable for oral administration, such as tablets, capsules, gelcaps, and caplets, which are adapted for controlled-release are encompassed by the present disclosure.

In certain embodiments, the formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form. For sustained release, the compounds may be formulated with a suitable polymer or hydrophobic material that provides sustained release properties to the compounds. As such, the compounds for use as described herein may be administered in the form of microparticles, for example, by injection or in the form of wafers or discs by implantation. In certain embodiments, the compounds are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours. The term pulsatile release is used herein in its conventional sense to refer to a drug formulation that provides release of the drug in such a way as to produce pulsed plasma profiles of the drug after drug administration. The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all w % bole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction and preparation conditions, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

6. Sequences

TABLE 1

| SEQ ID NO | Sequence | Description |
|---|---|---|
| 9 | WVEEPCESINEPQCPAGFETPPTLLFSLDGFRAEYLHTWGGLLPVISKLKKCG TYTKNMRPVYPTKTFPNHYSIVTGLYPESHGIIDNKMYDPKMNASFSLKSKEK FNPEWYKGEPIWVTAKYQGLKSGTFFWPGSDVEINGTFPDIYKMYNGSVPFEE RILAVLQWLQLPKDERPHFYTLYLEEPDSSGHSYGPVSSEVIKALQRVDGMVG MLMDGLKELNLHRCLNLILISDHGMEQGSCKKYIYENKYLGDVKNIKVIYGPA ARLRPSDVPDKYYSFNYEGIARNLSCREPNQHFKPYLKHFLPKRLHFAKSDRI EPLTFYLDPQWQLALNPSERKYCGSGFHGSDNVFSNMQALEVGYGPGFKHGIE ADTFENIEVYNLMCDLLNLTPAPNNGTHGSLNHLLKNPVYTPKHPKEVHPLVQ CPFTRNPRDNLGCSCNPSILPIEDEQTQFNLTVAEEKIIKHETLPYGRPRVLQ KENTICLLSQHQFMSGYSQDILMPLWTSYTVDRNDSFSTEDFSNCLYQDFRIP LSPVHKCSFYKNNTKVSYGFLSPPQLNKNSSGIYSEALLTTNIVPMYQSFQVI WRYFHDTLLRKYAEERNGVNVVSGPVFDFDYDGRCDSLENLRQKRRVIRNQEI LIPTHEFIVLTSCKDTSQTPLHCENLDTLAFILPHRTDNSESCVHGKHDSSWV EELLMLHRARITDVEHITGLSFYQQRKEPVSDILKLKTHLPTFSQED<u>LINDKT</u> | Mature ENPP1(190-925)-hFc is shown (with the linker underlined) |

TABLE 1-continued

| SEQ ID NO | Sequence | Description |
|---|---|---|
| | HTCPPCPAPELLGGPSVFLFPPPKPKDTLYITREPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDIAVEWE<br>SNGQPENNYKTTPPVLDSDGSFFLYSKLTVDKSRWQQGNVFSCSVMHEALHNH<br>YTQKSLSLSPGK | |
| 10 | MTRLTVLALLAGLLASSRAKSWVEEPCESINEPQCPAGFETPPTLLFSLDGFR<br>AEYLHTWGGLLPVISKLKKCGTYTKNMRPVYPTKTFPNHYSIVTGLYPESHGI<br>IDNKMYDPKMNASFSLKSKEKFNPEWYKGEPIWVTAKYQGLKSGTFFWPGSDV<br>EINGTFPDIYKMYNGSVPFEERILAVLQWLQLPKDERPHFYTLYLEEPDSSGH<br>SYGPVSSEVIKALQRVDGMVGMLMDGLKELNLHRCLNLILISDHGMEQGSCKK<br>YIYLNKYLGDVKNIKVIYGPAARLRPSDVPDKYYSFNYEGIARNLSCREPNQH<br>FKPYLKHFLPKRLHFAKSDRIEPLTFYLDPQWQLALNPSERKYCGSGFHGSDN<br>VFSNMQALEVGYGPGFKHGIEADTFENIEVYNLMCDLLNLTPAPNNGTHGSLN<br>HLLKNPVYTPKHPKEVHPLVQCPETRNPRDNLGCSCNPSILPIEDFQTQFNLT<br>VAEEKIIKHETLPYGRPRVLQKENTICLLSQHQFMSGYSQDILMPLWTSYTVD<br>RNDSFSTEDFSNCLYQDFRIPLSPVHKCSFYKNNTKVSYGFLSPPQLNKNSSG<br>IYSEALLTTNIVPMYQSFQVIWRYFHDTLLRKYAEERNGVNVVSGPVFDFDYD<br>GRCDSLENLRQKRRVIRNQEILIPTHFFIVLTSCKDTSQTPLHCENLDTLAFI<br>LPHRTDNSESCVHGKHDSSWVEELLMLHRARITDVEHITGLSFYQQRKEPVSD<br>ILKLKTHLPTFSQEDLINDKTHTCPPCPAPELLGGPSVFLFPPPKPKDTLYITR<br>EPEVTCVVVDVSHEDPEVKFNWYVDGVEVHNAKTKPREEQYNSTYRVVSVLTV<br>LHQDWLNGKEYKCKVSNKALPAPIEKTISKAKGQPREPQVYTIPPSREEMTKN<br>QVSLTCLVKGFYPSDIAVEWESNGQPENNYKTTPPVLDSDGSFFLYSKLTVDK<br>SRWQQGNVFSCSVMHEALHNHYTQKSLSLSPGK | Unprocessed<br>ENPP1(190-<br>925)-hFc<br>protein with<br>the signal<br>sequence<br>underlined |
| 11 | WVEEPCESINEPQCPAGFETPPTLLFSLDGFRAEYLHTWGGLLPVISKLKKCG<br>TYTKNMRPVYPTKTFPNHYSIVTGLYPESHGIIDNKMYDPKMNASFSLKSKEK<br>FNPEWYKGEPIWVTAKYQGLKSGTFFWPGSDVEINGTFPDIYKMYNGSVPFEE<br>RILAVLQWLQLPKDERPHFYTLYLEEPDSSGHSYGPVSSEVIKALQRVDGMVG<br>MLMDGLKELNLHRCLNLILISDHGMEQGSCKKYIYLNKYLGDVKNIKVIYGPA<br>ARLRPSDVPDKYYSFNYEGIARNLSCREPNQHFKPYLKHFLPKRLHFAKSDRI<br>EPLTFYLDPQWQLALNPSERKYCGSGFHGSDNVFSNMQALEVGYGPGFKHGIE<br>ADTFENIEVYNLMCDLLNLTPAPNNGTHGSLNHLLKNPVYTPKHPKEVHPLVQ<br>CPFTRNPRDNLGCSCNPSILPIEDFQTQFNLTVAEEKIIKHETLPYGRPRVLQ<br>KENTICLLSQHQFMSGYSQDILMPLWTSYTVDRNDSFSTEDFSNCLYQDFRIP<br>LSPVHKCSFYKNNTKVSYGFLSPPQLNKNSSGIYSEALLTTNIVPMYQSFQVI<br>WRYFHDTLLRKYAEERNGVNVVSGPVFDFDYDGRCDSLENLRQKRHVIRNQEI<br>LIPTHEFIVLTSCKDTSQTPLHCENLDTLAFILPHRTDNSESCVHGKHDSSWV<br>EELLMLHRARITDVEHITGLSFYQQRKEPVSDILKLKTHLPTFSQEDLINDKT<br>HTCPPCPAPELLGGPSVFLFPPPKPKDTLYITREPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDIAVEWE<br>SNGQPENNYKTTPPVLDSDGSFFLYSKLTVDKSRWQQGNVFSCSVMHEALHNH<br>YTQKSLSLSPGK | Mature<br>ENPP1(190-<br>925) R818H-<br>hFc with the<br>linker<br>underlined |
| 12 | MTRLTVLALLAGLLASSRAKSWVEEPCESINEPQCPAGFETPPTLLFSLDGFR<br>AEYLHTWGGLLPVISKLKKCGTYTKNMRPVYPTKTFPNHYSIVTGLYPESHGI<br>IDNKMYDPKMNASFSLKSKEKFNPEWYKGEPIWVTAKYQGLKSGTFFWPGSDV<br>EINGTFPDIYKMYNGSVPFEERILAVLQWLQLPKDERPHFYTLYLEEPDSSGH<br>SYGPVSSEVIKALQRVDGMVGMLMDGLKELNLHRCLNLILISDHGMEQGSCKK<br>YIYLNKYLGDVKNIKVIYGPAARLRPSDVPDKYYSFNYEGIARNLSCREPNQH<br>FKPYLKHELPKRLHFAKSDRIEPLTFYLDPQWQLALNPSERKYCGSGFHGSDN<br>VFSNMQALFVGYGPGFKHGIEADTFENIEVYNLMCDLLNLTPAPNNGTHGSIN<br>HLLKNPVYTPKHPKEVHPLVQCPFTRNPRDNLGCSCNPSILPIEDFQTQFNLT<br>VAEEKIIKHETLPYGRPRVLQKENTICLLSQHQFMSGYSQDILMPLWTSYTVD<br>RNDSFSTEDESNCLYQDFRIPLSPVHKCSFYKNNTKVSYGFLSPPQLNKNSSG<br>IYSEALLTTNIVPMYQSFQVIWRYFHDTLLRKYAEERNGVNVVSGPVFDFDYD<br>GRCDSLENLRQKRHVIRNQEILIPTHFFIVLTSCKDTSQTPLHCENLDTLAFI<br>LPHRTDNSESCVHGKHDSSWVEELLMLHRARITDVEHITGLSFYQQRKEPVSD<br>ILKLKTHLPTFSQEDLINDKTHTCPPCPAPELLGGPSVFLFPPPKPKDTLYITR<br>EPEVTCVVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSREEMTKN<br>QVSLTCLVKGFYPSDIAVEWESNGQPENNYKTTPPVLDSDGSFFLYSKLTVDK<br>SRWQQGNVFSCSVMHEALHNHYTQKSLSLSPGK | Unprocessed<br>ENPP1(190-<br>925)R818H-<br>hFc with the<br>signal<br>sequence<br>underlined |
| 13 | DKTHTCPPCPAPELLGGPSVFLFPPPKPKDTLYITREPEVTCVVVDVSHEDPEV<br>KFNWYVDGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCSVMHEAL<br>HNHYTQKSLSLSPGK | human IgG1<br>(G1Fc) |
| 14 | ggtaccgccaccatgacaagactgacagtgctggctctgctggccggactgtt<br>ggcctcttctagagctaagtcctgggttgaagaaccctgcgagtccatcaacg<br>agcctcagtgtcctgccggcttcgagacacctcctactctgctgttctccctg<br>gatggcttcagagccgagtacctgcatacttggggaggcctgctgccagtgat<br>ctccaagctgaagaagtgcggcacctacaccaagaacatgaggcctgtgtacc | ENPP1-Fc<br>Nucleotide<br>Sequence 1 |

TABLE 1-continued

| SEQ ID NO | Sequence | Description |
|---|---|---|
| | ctaccaagacattccccaaccactactccatcgtgaccggcctgtatcctgag<br>agccacggcatcatcgacaacaagatgtacgaccccaagatgaacgcctcctt<br>cagcctgaagtccaaagagaagttcaaccccgagtggtataagggcgagccta<br>tctgggtcaccgctaagtaccagggactgaagtctggcaccttctttggcct<br>ggctccgacgtggaaatcaacggcaccttccccgacatctataagatgtacaa<br>cggctccgtgcctttcgaggaacgcattctggctgttctgcagtggctgcagc<br>tgcctaaggatgagaggcctcacttctacaccctgtacctggaagaacctgac<br>tcctccggccactcttatggccctgtgtcctctgaagtgatcaaggccctgca<br>gcgagtggacggaatggtcggaatgctgatggacggcctgaaagagctgaacc<br>tgcacagatgcctgaacctgatcctgatctccgaccacggcatggaacagggg<br>agctgcaagaagtacatctacctgaacaagtacctgggcgacgtgaagaacat<br>caaagtgatctacgggcccagccgccagactgaggccttctgatgtgcctgaca<br>agtactactccttcaactacgagggaatcgcccggaacctgtcctgcagagag<br>cctaaccagcacttcaagccctacctgaagcactttctgcctaagcggctgca<br>cttcgccaagtctgacagaatcgagcccctgaccttctatctggaccctcagt<br>ggcagctggccctgaatcctagcgagagaaagtactgtggctccggcttccac<br>ggctccgacaacgtgttctctaatatgcaggccctgttcgtcggctacggccc<br>tggctttaaacacggcatcgaggccgacaccttcgagaacatcgaggtgtaca<br>atctgatgtgtgacctgctgaatctgacccctgctcctaacaacggcacccac<br>ggatctctgaaccatctgctgaagaatcccgtgtacaccccctaagcaccccaa<br>agaggttcaccctctggtccagtgtcctttcaccagaaatcctcgggacaacc<br>tgggctgctcttgcaacccttctatcctgcctatcgaggactttcagacccag<br>ttcaacctgaccgtggccgaggaaaagatcatcaagcacgagcactgcccta<br>cggcagacctagagtgctgcagaaagagaacaccatctgcctgctgtcccagc<br>accagttcatgtccggctactcccaggacatcctgatgcctctgtggacctcc<br>tacaccgtggaccggaacgatagcttctccaccgaggacttcagcaactgcct<br>gtaccaggatttcagaatccctctgagcccccgtgcacaagtgcagcttctaca<br>agaacaacaccaaggtgtcctacggcttcctgtctcctccacagctgaacaag<br>aactccagcggcatctactctgaggccctgctgaccaccaacatcgtgcccat<br>gtaccagtccttccaagtgatctggcggtacttccacgacaccctgctgagga<br>agtacgccgaagaaagaaacggcgtgaacgtggtgtctggccccgtgttcgac<br>ttcgactacgacggcagatgcgactctctggaaaacctgcggcagaaaagacg<br>agtgatccggaatcaagagatcctgattcctacacacttctttatcgtgctga<br>ccagctgcaaggatacctctcagacccctctgcactgcgagaatctggacacc<br>ctggccttcattctgcctcacagaaccgacaactccgagtcctgtgtgcacgg<br>caagcacgactcctcttgggtcgaagaactgctgatgctgcacgggccagaa<br>tcaccgatgtggaacacatcaccggcctgagcttctaccagcagcggaaagaa<br>cctgtgtccgatatcctgaagctgaaaacccatctgccaaccttcagccaaga<br>ggacctgatcaacgacaagacccacacctgtcctccatgtcctgctccagaac<br>tgctcggaggcccctctgtgttcctgtttccacctaagccaaaggacacactg<br>tacatcactcgggagcctgaagtgacctgcgtggtggtggatgtgtctcacga<br>agatcccgaagtcaagttcaattggtacgtggacggcgtggaagtgcacaacg<br>ccaagaccaagcctagagaggaacagtacaactccacctacagagtggtgtcc<br>gtgctgactgtgctgcaccaggattggctgaacggcaaagagtacaagtgcaa<br>agtgtccaacaaggctctgccccgctcctatcgaaaagaccatctccaaggcta<br>agggccagcctcgggaacctcaggtttacacccctgcctccatctcgggaagag<br>atgaccaagaaccaggtgtccctgacctgcctggtcaagggcttctaccccttc<br>cgatatcgccgtggaatgggagtccaatggccagcctgagaacaactacaaga<br>caacccctcctgtgctggacagcgacggctcattcttcctgtactctaagctg<br>acagtggacaagtcccggtggcagcaaggcaatgtgtttcctgctctgtgat<br>gcacgaggccctccacaatcactacacccagaagtccctgtctctgtccctg<br>gcaaatgatagctcgag | |
| 15 | ggtaccgccaccatgacaagactgacagtgctggctctgctggccggactgtt<br>ggcctcttctagagctaagtcctgggttgaagaaccctgcgagtccatcaacg<br>agcctcagtgtcctgccggcttcgagacacctcctactctgctgttctccctg<br>gatggcttcagagccgagtacctgcatacttggggaggcctgctgccagtgat<br>ctccaagctgaagaagtgcggcacctacaccaagaacatgaggcctgtgtacc<br>ctaccaagacattccccaaccactactccatcgtgaccggcctgtatcctgag<br>agccacggcatcatcgacaacaagatgtacgaccccaagatgaacgcctcctt<br>cagcctgaagtccaaagagaagttcaaccccgagtggtataagggcgagccta<br>tctgggtcaccgctaagtaccagggactgaagtctggcaccttctttggcct<br>ggctccgacgtggaaatcaacggcaccttccccgacatctataagatgtacaa<br>cggctccgtgcctttcgaggaacgcattctggctgttctgcagtggctgcag<br>tgcctaaggatgagaggcctcacttctacaccctgtacctggaagaacctgac<br>tcctccggccactcttatggccctgtgtcctctgaagtgatcaaggccctgca<br>gcgagtggacggaatggtcggaatgctgatggacggcctgaaagagctgaacc<br>tgcacagatgcctgaacctgatcctgatctccgaccacggcatggaacagggg<br>agctgcaagaagtacatctacctgaacaagtacctgggcgacgtgaagaacat<br>caaagtgatctacgggcccagccgccagactgaggccttctgatgtgcctgaca<br>agtactactccttcaactacgagggaatcgcccggaacctgtcctgcagagag<br>cctaaccagcacttcaagccctacctgaagcactttctgcctaagcggctgca<br>cttcgccaagtctgacagaatcgagcccctgaccttctatctggaccctcagt<br>ggcagctggccctgaatcctagcgagagaaagtactgtggctccggcttccac<br>ggctccgacaacgtgttctctaatatgcaggccctgttcgtcggctacggccc<br>tggctttaaacacggcatcgaggccgacaccttcgagaacatcgaggtgtaca<br>atctgatgtgtgacctgctgaatctgacccctgctcctaacaacggcacccac | ENPP1-Fc nucleotide sequence 2 |

TABLE 1-continued

| SEQ ID NO | Sequence | Description |
|---|---|---|
|  | ggatctctgaaccatctgctgaagaatcccgtgtacacccctaagcaccccaa agaggttcaccctctggtccagtgtcctttcaccagaaatcctcgggacaacc tgggctgctcttgcaacccttctatcctgcctatcgaggactttcagacccag ttcaacctgaccgtggccgaggaaaagatcatcaagcacgagacactgcccta cggcagacctagagtgctgcagaaagagaacaccatctgcctgctgtcccagc accagttcatgtccggctactcccaggacatcctgatgcctctgtggacctcc tacaccgtggaccggaacgatagcttctctaccgaggacttcagcaactgcct gtaccaggatttcagaatccctctgagccccgtgcacaagtgcagcttctaca agaacaacaccaaggtgtcctacggcttcctgtctcctccacagctgaacaag aactccagcggcatctactctgaggccctgctgaccaccaacatcgtgcccat gtaccagtccttccaagtgatctggcggtacttccacgacaccctgctgagga agtacgccgaagaaagaaacggcgtgaacgtggtgtctggccccgtgttcgac ttcgactacgacggcagatgcgactctctggaaaacctgcggcagaaaagaca cgtgatccggaatcaagagatcctgattcctacacacttctttatcgtgctga ccagctgcaaggatacctctcagaccccctctgcactgcgagaatctggacacc ctggccttcattctgcctcacagaaccgacaactccgagtcctgtgtgcacgg caagcacgactcctcttgggtcgaagaactgctgatgctgcaccgggccagaa tcaccgatgtggaacacatcaccggcctgagcttctaccagcagcggaaagaa cctgtgtccgatatcctgaagctgaaaacccatctgccaaccttcagccaaga ggacctgatcaacgacaagacccacacctgtcctccatgtcctgctccagaac tgctcggaggcccctctgtgttcctgtttccacctaagccaaaggacacactg tacatcactcgggagcctgaagtgacctgcgtggtggtggatgtgtctcacga agatcccgaagtgcaagttcaattggtacgtggacggcgtggaagtgcacaacg ccaagaccaagcctagagaggaacagtacaactccacctacagagtggtgtcc gtgctgactgtgctgcaccaggattggctgaacggcaaagagtacaagtgcaa agtgtccaacaaggctctgcccgctcctatcgaaaagaccatctccaaggcta agggccagcctcgggaacctcaggtttacaccctgcctccatctcgggaagag atgaccaagaaccaggtgtccctgacctgcctggtcaagggcttctacccttc cgatatcgccgtggaatgggagtccaatggccagcctgagaacaactacaaga caacccctcctgtgctggacagcgacggctcattcttcctgtactctaagctg acagtggacaagtcccggtggcagcaaggcaatgtgttttcctgctctgtgat gcacgaggccctccacaatcactacacccagaagtccctgtctctgtcccctg gcaaatgatagctcgag |  |
| 16 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVYTLPPSREEMTKNQVSLTCLVKGFYPSDIAV EWESNGQPENNYKTTPPVLDSDGSFFLYSKLTVDKSRWQQGNVFSCSVMHEAL HNHYTQKSLSLSPGK | hIgG Fc domain, Fc |
| 17 | MTSKFLLVSFILAALSLSTTFS-Xaa$_{23}$Xaa$_{24}$<br>wherein Xaa$_{23}$ is absent or L, and<br>wherein Xaa$_{24}$ is absent if Xaa$_{23}$ is absent and Xaa$_{24}$ is<br>absent or Q if<br>Xaa$_{23}$ is L | hENPP5 protein export signal sequence |
| 18 | MRGPAVLLTVALATLLAPGAGA | hENPP7 protein export signal sequence |
| 19 | MRGPAVLLTVALATLLAPGA | hENPP7 protein export signal sequence |
| 117 | PSCAKEVKSCKGRCFERTFGNCRCDAACVELGNCCLDYQETCIEPEHIWTCNK FRCGEKRLTRSLCACSDDCKDKGDCCINYSSVCQGEKSWVEEPCESINEPQCP AGFETPPTLLESLDGFRAEYLHTWGGLLPVISKLKKCGTYTKNMRPVYPTKTF PNHYSIVTGLYPESHGIIDNKMYDPKMNASFSLKSKEKFNPEWYKGEPIWVTA KYQGLKSGTFFWPGSDVEINGIFPDIYKMYNGSVPFEERILAVLQWLQLPKDE RPHFYTLYLEEPDSSGHSYGPVSSEVIKALQRVDNMVGMLMDGLKELNLHRCL NLILVSDHGMEQGSCKKYIYLNKYLGDVKNIKVIYGPAARLRPSDVPDKYYSF NYEGIARNLSCREPNQHFKPYLKHFLPKRLHFAKSDRIEPLTFYLDPQWQLAL NPSERKYCGSGFHGSDNIFSNMQALFVGYGPGFKHGIEVDTFENIEVYNLMCD LLNLTPAPNNGTHGSLNHLLKNPVYTPKHPKEVHPLIQCPETRNPRDNLGCSC NPSILPIEDFQTQFNLTVAEEKNIKHETLPYGRPRVLQKENTICLLSQHQFMS GYSQDILMPLWTSYTVDRNDSFSTEDFSNCLYQDFRIPLSPVHKCSFYKNNTK VSYGFLSPPQLNKNSSGIYSEALLTTNIVPMYQSFQVIWRYFHDTLLRKYAEE RNGVNVVSGPVFDFDYDGRCDSLENLRQKRRVIRNQEILIPTHFFIVLTSCKD TSQTPLHCENLDTLAFILPHRTDNSESCVHGKHDSSWVEELLMLHRARITDVE HITGLSFYQQRKEPVSDILKLKTHLPTFSQEDLINDKTHTCPPCPAPELLGGP SVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK | Test Construct 3 |

TABLE 1-continued

| SEQ ID NO | Sequence | Description |
|---|---|---|
| 118 | PSCAKEVKSCKGRCFERTFGNCRCDAACVELGNCCLDYQETCIEPEHIWTCNK<br>FRCGEKRLTRSLCACSDDCKDKGDCCINYSSVCQGEKSWVEEPCESINEPQCP<br>AGFETPPTLLESLDGFRAEYLHTWGGLLPVISKLKKCGTYTKNMRPVYPTKTF<br>PNHYSIVTGLYPESHGIIDNKMYDPKMNASFSLKSKEKFNPEWYKGEPIWVTA<br>KYQGLKSGTFEWPGSDVEINGIFPDIYKMYNGSVPFEERILAVLQWLQLPKDE<br>RPHFYTLYLEEPDSSGHSYGPVSSEVIKALQRVDGMVGMLMDGLKELNLHRCL<br>NLILISDHGMEQGSCKKYTYLNKYLGDVKNIKVIYGPAARLRPSDVPDKYYSF<br>NYEGIARNLSCREPNQHFKPYLKHFLPKRLHFAKSDRIEPLTFYLDPQWQLAL<br>NPSERKYCGSGFHGSDNVFSNMQALFVGYGPGFKHGIEADTFENIEVYNLMCD<br>LLNLTPAPNNGTHGSLNHLLKNPVYTPKHPKEVHPLVQCPFTRNPRDNLGCSC<br>NPSILPIEDFQTQFNLTVAEEKIIKHETLPYGRPRVLQKKNTICLLSQHQFMS<br>GYSQDILMPLWTSYTVDRNDSFSTEDFSNCLYQDFRISLSPVHKCSFYKNNTK<br>VSYGFLSPPQLNKNSSGIYSEALLTTNIVPMYQSFQVIWRYFHDTLLRKYAEE<br>RNGVNVVSGPVFDFDYDGRYDSLEILRQKRRVIRNQEILIPTHFFIVLTSCKD<br>ASQTPLHCENLDTLAFILPHRTDNSESCVHGKHESSWVEELLMLHRARITDVE<br>HITGLSFYQQRKEPVSDILKLKTHLPTFSQEDLINDKTHTCPPCPAPELLGGP<br>SVFLFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK | Test<br>Construct 4 |
| 119 | PSCAKEVKSCKGRCFERTFGNCRCDAACVELGNCCLDYQETCIEPEHIWTCNK<br>FRCGEKRLTRSLCACSDDCKDKGDCCINYSSVCQGEKSWVEEPCESINEPQCP<br>AGFETPPTLLESLDGFRAEYLHTWGGLLPVISKLKKCGTYTKNMRPVYPTKTF<br>PNHYSIVTGLYPESHGIIDNKMYDPKMNASFSLKSKEKFNPEWYKGEPIWVTA<br>KYQGLKSGTFFWPGSDVEINGIFPDIYKMYNGSVPFEERILAVLQWLQLPKDE<br>RPHFYTLYLEEPDSSGHSYGPVSSEVIKALQRVDGMVGMLMDGLKELNLHRCL<br>NLILISDHGMEQGSCKKYIYLNKYLGDVKNIKVIYGPAARLRPSDVPDKYYSE<br>NYEGIARNLSCREPNQHFKPYLKHELPKRLHFAKSDRIEPLTFYLDPQWQLAL<br>NPSERKYCGSGFHGSDNVFSNMQALFVGYGPGFKHGIEADTFENIEVYNLMCD<br>LLNLTPAPNNGTHGSLNHLLKNPVYTPKHPKEVHPLVQCPFTRNPRDNLGCSC<br>NPSILPIEDFQTQFNLTVAEEKIIKHETLPYGRPRVLQKENTICLLSQHQFMS<br>GYSQDILMPLWTSYTVDRNDSFSTEDFSNCLYQDFRIPLSPVHKCSFYKNNTK<br>VSYGFLSPPQLNKNSSGIYSEALLTTNIVPMYQSFQVIWRYFHDTLLRKYAEE<br>RNGVNVVSGPVFDFDYDGRCDSLENLRQKRRVIRNQEILIPTHFFIVLTSCKD<br>TSQTPLHCENLDTLAFILPHRTDNSESCVHGKHDSSWVEELLMLHRARITDVE<br>HITGLSFYQQRKEPVSDILKLKTHLPTFSQEDGGGGSDKTHTCPPCPAPELLG<br>GPSVFLFPPKPKDTLMISRTPEVTCVVVDVSHEDPEVKFNWYVDGVEVHNAKT<br>KPREEQYNSTYRVVSVLTVLHQDWINGKEYKCKVSNKALPAPIEKTISKAKGQ<br>PREPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK | Test<br>Construct 5 |
| 120 | PSCAKEVKSCKGRCFERTEGNCRCDAACVELGNCCLDYQETCIEPEHIWTCNK<br>FRCGEKRLTRSLCACSDDCKDKGDCCINYSSVCQGEKSWVEEPCESINEPQCP<br>AGFETPPTLLESLDGFRAEYLHTWGGLLPVISKLKKCGTYTKNMRPVYPTKTF<br>PNHYSIVTGLYPESHGIIDNKMYDPKMNASFSLKSKEKFNPEWYKGEPIWVTA<br>KYQGLKSGTFFWPGSDVEINGTFPDIYKMYNGSVPFEERILAVLQWLQLPKDE<br>RPHFYTLYLEEPDSSGHSYGPVSSEVIKALQRVDGMVGMLMDGLKELNLHRCL<br>NLILISDHGMEQGSCKKYIYLNKYLGDVKNIKVIYGPAARLRPSDVPDKYYSF<br>NYEGIARNLSCREPNQHFKPYLKHFLPKRLHFAKSDRIEPLTFYLDPQWQLAL<br>NPSERKYCGSGFHGSDNVFSNMQALFVGYGPGFKHGIEADTFENIEVYNLMCD<br>LLNLTPAPNNGTHGSLNHLLKNPVYTPKHPKEVHPLVQCPFTRNPRDNLGCSC<br>NPSILPIEDFQTQFNLTVAEEKIIKHETLPYGRPRVLQKENTICLLSQHQFMS<br>GYSQDILMPLWTSYTVDRNDSFSTEDESNCLYQDFRIPLSPVHKCSFYKNNTK<br>VSYGFLSPPQLNKNSSGIYSEALLTTNIVPMYQSFQVIWRYFHDTLLRKYAEE<br>RNGVNVVSGPVFDFDYDGRCDSLENLRQKRRVIRNQEILIPTHFFIVLTSCKD<br>TSQTPLHCENLDTLAFILPHRTDNSESCVHGKHDSSWVEELLMLHRARITDVE<br>HITGLSFYQQRKEPVSDILKLKTHLPTFSQEDGGGGSDKTHTCPPCPAPELLG<br>GPSVFLFPPKPKDTLYITREPEVTCVVVDVSHEDPEVKFNWYVDGVEVHNAKT<br>KPREEQYNSTYRVVSVLTVLHQDWINGKEYKCKVSNKALPAPIEKTISKAKGQ<br>PREPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK | Test<br>Construct 6 |
| 121 | WVEEPCESINEPQCPAGFETPPTLLESLDGFRAEYLHTWGGLLPVISKLKKCG<br>TYTKNMRPVYPTKTFPNHYSIVTGLYPESHGIIDNKMYDPKMNASFSLKSKEK<br>FNPEWYKGEPIWVTAKYQGLKSGTFFWPGSDVEINGTFPDIYKMYNGSVPFEE<br>RILAVLQWLQLPKDERPHFYTLYLEEPDSSGHSYGPVSSEVIKALQRVDGMVG<br>MLMDGLKELNLHRCLNLILISDHGMEQGSCKKYIYLNKYLGDVKNIKVIYGPA<br>ARLRPSDVPDKYYSFNYEGIARNLSCREPNQHFKPYLKHELPKRLHFAKSDRI<br>EPLTFYLDPQWQLALNPSERKYCGSGFHGSDNVFSNMQALEVGYGPGFKHGIE<br>ADTFENIEVYNLMCDLLNLTPAPNNGTHGSLNHLLKNPVYTPKHPKEVHPLVQ<br>CPFTRNPRDNLGCSCNPSILPIEDFQTQFNLTVAEEKIIKHETLPYGRPRVLQ<br>KENTICLLSQHQFMSGYSQDILMPLWTSYTVDRNDSFSTEDFSNCLYQDFRIP<br>LSPVHKCSFYKNNTKVSYGFLSPPQLNKNSSGIYSEALLTTNIVPMYQSFQVI<br>WRYFHDTLLRKYAEERNGVNVVSGPVFDFDYDGRCDSLENLRQKRRVIRNQEI<br>LIPTHEFIVLTSCKDTSQTPLHCENLDTLAFILPHRTDNSESCVHGKHDSSWV<br>EELLMLHRARITDVEHITGLSFYQQRKEPVSDILKLKTHLPTFSQEDGGGGSD | Test<br>Construct 7 |

TABLE 1-continued

| SEQ ID NO | Sequence | Description |
|---|---|---|
|  | KTHTCPPCPAPELLGGPSVFLFPPKPKDTLYITREPEVTCVVVDVSHEDPEVK FNWYVDGVEVHNAKTKPREEQYNSTYRVVSVLTVLHQDWLNGKEYKCKVSNKA LPAPIERTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALH NHYTQKSLSLSPGK |  |
| 122 | WVEEPCESINEPQCPAGFETPPTLLFSLDGFRAEYLHTWGGLLPVISKLKKCG TYTKNMRPVYPTKTFPNHYSIVTGLYPESHGIIDNKMYDPKMNASFSLKSKEK FNPEWYKGEPIWVTAKYQGLKSGTFFWPGSDVEINGIFPDIYKMYNGSVPFEE RILAVLQWLQLPKDERPHFYTLYLEEPDSSGHSYGPVSSEVIKALQRVDGMVG MLMDGLKELNLHRCLNLILISDHGMEQGSCKKYIYENKYLGDVKNIKVIYGPA ARLRPSDVPDKYYSFNYEGIARNLSCREPNQHFKPYLKHFLPKRLHFAKSDRI EPLTFYLDPQWQLALNPSERKYCGSGFHGSDNVFSNMQALFVGYGPGFKHGIE ADTFENIEVYNLMCDLLNLTPAPNNGTHGSLNHLLKNPVYTPKHPKEVHPLVQ CPFTRNPRDNLGCSCNPSILPIEDEQTQFNLTVAEEKIIKHETLPYGRPRVLQ KENTICLLSQHQFMSGYSQDILMPLWTSYTVDRNDSFSTEDFSNCLYQDFRIP LSPVHKCSFYKNNTKVSYGFLSPPQLNKNSSGIYSEALLTTNIVPMYQSFQVI WRYFHDTLLRKYAEERNGVNVVSGPVFDFDYDGRCDSLENLRQKRRVIRNQEI LIPTHEFIVLTSCKDTSQTPLHCENLDTLAFILPHRTDNSESCVHGKHDSSWV EELLMLHRARITDVEHITGLSFYQQRKEPVSDILKLKTHLPTFSQEDLINDKT HTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNH YTQKSLSLSPGK | Test Construct 2 |
| 123 | MTRLTVLALLAGLLASSRAPSCAKEVKSCKGRCFERTEGNCRCDAACVELGNC CLDYQETCIEPEHIWTCNKFRCGEKRLTRSLCACSDDCKDKGDCCINYSSVCQ GEKSWVEEPCESINEPQCPAGFETPPTLLESLDGFRAEYLHTWGGLLPVISKL KKCGTYTKNMRPVYPTKTFPNHYSIVTGLYPESHGIIDNKMYDPKMNASFSLK SKEKFNPEWYKGEPIWVTAKYQGLKSGTFEWPGSDVEINGIFPDIYKMYNGSV PFEERILAVLQWLQLPKDERPHFYTLYLEEPDSSGHSYGPVSSEVIKALQRVD NMVGMLMDGLKELNLHRCLNLILVSDHGMEQGSCKKYIYLNKYLGDVKNIKVI YGPAARLRPSDVPDKYYSFNYEGIARNLSCREPNQHFKPYLKHFLPKRLHFAK SDRIEPLTFYLDPQWQLALNPSERKYCGSGFHGSDNIFSNMQALFVGYGPGFK HGIEVDTFENIEVYNLMCDLLNLTPAPNNGTHGSLNHLLKNPVYTPKHPKEVH PLIQCPFTRNPRDNLGCSCNPSILPIEDFQTQFNLTVAEEKNIKHETLPYGRP RVLQKENTICLLSQHQFMSGYSQDILMPLWTSYTVDRNDSFSTEDFSNCLYQD FRIPLSPVHKCSFYKNNTKVSYGFLSPPQLNKNSSGIYSEALLTTNIVPMYQS FQVIWRYFHDTLLRKYAEERNGVNVVSGPVFDFDYDGRCDSLENLRQKRRVIR NQEILIPTHFFIVLTSCKDTSQTPLHCENLDTLAFILPHRTDNSESCVHGKHD SSWVEELLMLHRARITDVEHITGLSFYQQRKEPVSDILKLKTHLPTFSQEDLI NDKTHTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCKVSN KALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEA LHNHYTQKSLSLSPGK | Test Construct 3 with the signal sequence underlined |
| 124 | MTRLTVLALLAGLLASSRAPSCAKEVKSCKGRCFERTFGNCRCDAACVELGNC CLDYQETCIEPEHIWTCNKFRCGEKRLTRSLCACSDDCKDKGDCCINYSSVCQ GEKSWVEEPCESINEPQCPAGFETPPTLLFSLDGFRAEYLHTWGGLLPVISKL KKCGTYTKNMRPVYPTKTFPNHYSIVTGLYPESHGIIDNKMYDPKMNASFSLK SKEKFNPEWYKGEPIWVTAKYQGLKSGTFFWPGSDVEINGIFPDIYKMYNGSV PFEERILAVLQWLQLPKDERPHFYTLYLEEPDSSGHSYGPVSSEVIKALQRVD GMVGMLMDGLKELNLHRCLNLILISDHGMEQGSCKKYIYLNKYLGDVKNIKVI YGPAARLRPSDVPDKYYSFNYEGIARNLSCREPNQHFKPYLKHFLPKRLHFAK HGIEADTFENIEVYNLMCDLLNLTPAPNNGTHGSLNHLLKNPVYTPKHPKEVH PLVQCPFTRNPRDNLGCSCNPSILPIEDFQTQFNLTVAEEKIIKHETLPYGRP RVLQKKNTICLLSQHQFMSGYSQDILMPLWTSYTVDRNDSFSTEDFSNCLYQD FRISLSPVHKCSFYKNNTKVSYGFLSPPQLNKNSSGIYSEALLTTNIVPMYQS FQVIWRYFHDTLLRKYAEERNGVNVVSGPVFDFDYDGRYDSLEILRQKRRVIR NQEILIPTHFFIVLTSCKDASQTPLHCENLDTLAFILPHRTDNSESCVHGKHE SSWVEELLMLHRARITDVEHITGLSFYQQRKEPVSDILKLKTHLPTFSQEDLI NDKTHTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCKVSN KALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEA LHNHYTQKSLSLSPGK | Test Construct 4 with the signal sequence underlined |
| 125 | MTRLTVLALLAGLLASSRAPSCAKEVKSCKGRCFERTFGNCRCDAACVELGNC CLDYQETCIEPEHIWTCNKFRCGEKRLTRSLCACSDDCKDKGDCCINYSSVCQ GEKSWVEEPCESINEPQCPAGFETPPTLLFSLDGFRAEYLHTWGGLLPVISKL KKCGTYTKNMRPVYPTKTFPNHYSIVTGLYPESHGIIDNKMYDPKMNASFSLK SKEKFNPEWYKGEPIWVTAKYQGLKSGTFFWPGSDVEINGIFPDIYKMYNGSV PFEERILAVLQWLQLPKDERPHFYTLYLEEPDSSGHSYGPVSSEVIKALQRVD GMVGMLMDGLKELNLHRCLNLILISDHGMEQGSCKKYTYLNKYLGDVKNIKVI YGPAARLRPSDVPDKYYSFNYEGIARNLSCREPNQHFKPYLKHFLPKRLHFAK | Test Construct 5 with the signal sequence underlined |

TABLE 1-continued

| SEQ ID NO | Sequence | Description |
|---|---|---|
| | SDRIEPLTFYLDPQWQLALNPSERKYCGSGFHGSDNVFSNMQALFVGYGPGFK HGIEADTFENIEVYNLMCDLLNLTPAPNNGTHGSLNHLLKNPVYTPKHPKEVH PLVQCPFTRNPRDNLGCSCNPSILPIEDFQTQENLTVAEEKIIKHETLPYGRP RVLQKENTICLLSQHQFMSGYSQDILMPLWTSYTVDRNDSFSTEDFSNCLYQD FRIPLSPVHKCSFYKNNTKVSYGFLSPPQLNKNSSGIYSEALLTTNIVPMYQS FQVIWRYFHDTLLRKYAEERNGVNVVSGPVFDFDYDGRCDSLENLRQKRRVIR NQEILIPTHFFIVLTSCKDTSQTPLHCENLDTLAFILPHRTDNSESCVHGKHD SSWVEELLMLHRARITDVEHITGLSFYQQRKEPVSDILKLKTHLPTFSQEDGG GGSDKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGKEYKCKV SNKALPAPIEKTISKAGQPREPQVYTLPPSREEMTKNQVSLTCLVKGFYPSD IAVEWESNGQPENNYKTTPPVLDSDGSFFLYSKLTVDKSRWQQGNVFSCSVMH EALHNHYTQKSLSLSPGK | |
| 126 | MTRLTVLALLAGLLASSRAPSCAKEVKSCKGRCFERTFGNCRCDAACVELGNC CLDYQETCIEPEHIWTCNKFRCGEKRLTRSLCACSDDCKDKGDCCINYSSVCQ GEKSWVEEPCESINEPQCPAGFETPPTLLESLDGFRAEYLHTWGGLLPVISKL KKCGTYTKNMRPVYPTKTFPNHYSIVTGLYPESHGIIDNKMYDPKMNASFSLK SKEKFNPEWYKGEPIWVTAKYQGLKSGTFFWPGSDVEINGTFPDIYKMYNGSV PFEERILAVLQWLQLPKDERPHFYTLYLEEPDSSGHSYGPVSSEVIKALQRVD GMVGMLMDGLKELNLHRCLNLILISDHGMEQGSCKKYIYLNKYLGDVKNIKVI YGPAARLRPSDVPDKYYSFNYEGIARNLSCREPNQHFKPYLKHFLPKRLHFAK SDRIEPLTFYLDPQWQLALNPSERKYCGSGFHGSDNVFSNMQALFVGYGPGEK HGIEADTFENIEVYNLMCDLLNLTPAPNNGTHGSLNHLLKNPVYTPKHPKEVH PLVQCPETRNPRDNLGCSCNPSILPIEDFQTQFNLTVAEEKIIKHETLPYGRP RVLQKENTICLLSQHQEMSGYSQDILMPLWTSYTVDRNDSFSTEDFSNCLYQD FRIPLSPVHKCSFYKNNTKVSYGFLSPPQLNKNSSGIYSEALLTTNIVPMYQS FQVIWRYFHDTLLRKYAEERNGVNVVSGPVFDFDYDGRCDSLENLRQKRRVIR NQEILIPTHFFIVLTSCKDTSQTPLHCENLDTLAFILPHRTDNSESCVHGKHD SSWVEELLMLHRARITDVEHITGLSFYQQRKEPVSDILKLKTHLPTFSQEDGG GGSDKTHTCPPCPAPELLGGPSVFLFPPKPKDTLYITREPEVTCVVVDVSHED PEVKFNWYVDGVEVHNAKTKPREEQYNSTYRVVSVLTVLHQDWLNGKEYKCKV SNKALPAPIEKTISKAGQPREPQVYTLPPSREEMTKNQVSLTCLVKGFYPSD IAVEWESNGQPENNYKTTPPVLDSDGSFFLYSKLTVDKSRWQQGNVFSCSVMH EALHNHYTQKSLSLSPGK | Test Construct 6 with the signal sequence underlined |
| 127 | MTRLTVLALLAGLLASSRAKSWVEEPCESINEPQCPAGFETPPTLLESLDGFR AEYLHTWGGLLPVISKLKKCGTYTKNMRPVYPTKTFPNHYSIVTGLYPESHGI IDNKMYDPKMNASFSLKSKEKFNPEWYKGEPIWVTAKYQGLKSGTFFWPGSDV EINGTFPDIYKMYNGSVPFEERILAVLQWLQLPKDERPHFYTLYLEEPDSSGH SYGPVSSEVIKALQRVDGMVGMLMDGLKELNLHRCLNLILISDHGMEQGSCKK YIYLNKYLGDVKNIKVIYGPAARLRPSDVPDKYYSFNYEGIARNLSCREPNQH FKPYLKHELPKRLHFAKSDRIEPLTFYLDPQWQLALNPSERKYCGSGFHGSDN VESNMQALEVGYGPGFKHGIEADTFENIEVYNLMCDLLNLTPAPNNGTHGSLN HLLKNPVYTPKHPKEVHPLVQCPETRNPRDNLGCSCNPSILPIEDFQTQFNLT VAEEKIIKHETLPYGRPRVLQKENTICLLSQHQFMSGYSQDILMPLWTSYTVD RNDSFSTEDFSNCLYQDFRIPLSPVHKCSFYKNNTKVSYGFLSPPQLNKNSSG IYSEALLTTNIVPMYQSFQVIWRYFHDTLLRKYAEERNGVNVVSGPVFDFDYD GRCDSLENLRQKRRVIRNQEILIPTHFFIVLTSCKDTSQTPLHCENLDTLAFI LPHRTDNSESCVHGKHDSSWVEELLMLHRARITDVEHITGLSFYQQRKEPVSD ILKLKTHLPTFSQEDGGGGSDKTHTCPPCPAPELLGGPSVFLFPPKPKDTLYI TREPEVTCVVVDVSHEDPEVKFNWYVDGVEVHNAKTKPREEQYNSTYRVVSVL TVLHQDWLNGKEYKCKVSNKALPAPIEKTISKAGQPREPQVYTLPPSREEMT KNQVSLTCLVKGFYPSDIAVEWESNGQPENNYKTTPPVLDSDGSFFLYSKLTV DKSRWQQGNVFSCSVMHEALHNHYTQKSLSLSPGK | Test Construct 7 with the signal sequence underlined |
| 128 | MTRLTVLALLAGLLASSRAKSWVEEPCESINEPQCPAGFETPPTLLFSLDGFR AEYLHTWGGLLPVISKLKKCGTYTKNMRPVYPTKTFPNHYSIVTGLYPESHGI IDNKMYDPKMNASFSLKSKEKFNPEWYKGEPIWVTAKYQGLKSGTFFWPGSDV EINGIFPDIYKMYNGSVPFEERILAVLQWLQLPKDERPHFYTLYLEEPDSSGH SYGPVSSEVIKALQRVDGMVGMLMDGLKELNLHRCLNLILISDHGMEQGSCKK YIYLNKYLGDVKNIKVIYGPAARLRPSDVPDKYYSFNYEGIARNLSCREPNQH FKPYLKHELPKRLHFAKSDRIEPLTFYLDPQWQLALNPSERKYCGSGFHGSDN VFSNMQALEVGYGPGFKHGIEADTFENIEVYNLMCDLLNLTPAPNNGTHGSLN HLLKNPVYTPKHPKEVHPLVQCPFTRNPRDNLGCSCNPSILPIEDFQTQENLT VAEEKIIKHETLPYGRPRVLQKENTICLLSQHQFMSGYSQDILMPLWTSYTVD RNDSFSTEDFSNCLYQDFRIPLSPVHKCSFYKNNTKVSYGELSPPQLNKNSSG IYSEALLTTNIVPMYQSFQVIWRYFHDTLLRKYAEERNGVNVVSGPVFDFDYD GRCDSLENLRQKRRVIRNQEILIPTHFFIVLTSCKDTSQTPLHCENLDTLAFI LPHRTDNSESCVHGKHDSSWVEELLMLHRARITDVEHITGLSFYQQRKEPVSD ILKLKTHLPTFSQEDLINDKTHTCPPCPAPELLGGPSVFLFPPKPKDTLMISR TPEVTCVVVDVSHEDPEVKFNWYVDGVEVHNAKTKPREEQYNSTYRVVSVLTV LHQDWLNGKEYKCKVSNKALPAPIEKTISKAGQPREPQVYTLPPSREEMTKN QVSLTCLVKGFYPSDIAVEWESNGQPENNYKTTPPVLDSDGSFFLYSKLTVDK SRWQQGNVFSCSVMHEALHNHYTQKSLSLSPGK | Test Construct 2 with the signal sequence underlined |

The terms used in this specification generally have their ordinary meanings in the art, within the context of this disclosure and in the specific context where each term is used. Certain terms are discussed below or elsewhere in the specification, to provide additional guidance to the practitioner in describing the compositions and methods of the disclosure and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A. B. and/or C" is intended to encompass each of the following aspects: A, B, and C; A, B, or C; A or C: A or B: B or C: A and C: A and B; B and C: A (alone); B (alone); and C (alone).

Numeric ranges disclosed herein are inclusive of the numbers defining the ranges.

A polypeptide disclosed herein can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting (e.g., naturally-occurring or wild-type) polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

Preferred methods and materials are described herein, although methods and materials similar or equivalent to those described herein can also be used in the practice or testing of the presently disclosed methods and compositions. All publications, patent applications, patents, and other references mentioned herein are incorporated by reference in their entirety.

Exemplification

The invention now being generally described, it will be more readily understood by reference to the following examples, which are included merely for purposes of illustration of certain embodiments and embodiments of the present invention, and are not intended to limit the invention.

Example 1. Generation of ENPP1 Fusion Proteins

A soluble ENPP1 fusion protein that lacks both SMB1 and SMB2 domain of ENPP1 fused to a human Fc domain with a linker (comprising a leucine, isoleucine, and asparagine) in-between was constructed. This construct is referred to as ENPP1(190-925)-hFc.

ENPP1 (190-925)-hFc is shown in Table 1 as SEQ ID NO: 9 (with the linker underlined) as purified from CHO cell lines.

The ENPP1 (190-925)-hFc protein expressed in CHO cell lines using a SP(2) leader sequence has the unprocessed amino acid sequence shown in SEQ ID NO: 10 (Table 1).

The nucleotide sequence encoding the unprocessed amino acid sequence for ENPP1 (190-925)-hFc (SEQ ID NO: 10) is shown as SEQ ID NO: 14 in Table 1.

N-terminal sequencing of the CHO-cell produced material revealed a major sequence of —WVEEPC (SEQ ID NO: 132) indicating cleavage at SRA-KS (SEQ ID NO: 133) (in-between the serine (S) and tryptophan (W) at residues 189 and 190, respectively, with respect to SEQ ID NO: 1).

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Following purification of the protein, the catalytic activity of the ENPP1 (190-925)-hFc protein was evaluated using pNP-TMP as a chromogenic substrate and it was determined that the deletion of SMB1 and SMB2 did not affect ENPP1 enzymatic activity. Deletion of the SMB1 and SMB2 domains are expected to decrease aggregation of the polypeptide and/or significantly reduce the likelihood that anti-drug antibodies will be generated by mammals against deletion mutants, relative to ENPP1-Fc polypeptides containing the SMB domains.

Example 2. Generation of Protease Resistant ENPP1 Fusion Proteins

Following the purification steps described above, polypeptide analysis showed that a small percentage of polypeptides were clipped in the nuclease domain of ENPP1 by a protease (i.e., trypsin or trypsin-like proteases) resulting in cleavage of the polypeptide. Based on these findings, a series of mutations (sequence variations) in the nuclease domain of ENPP1 were generated and these variant polypeptides were produced as fusion proteins comprising a variant ENPP1 nuclease domain and an Fc domain joined by an optional linker. The background ENPP1-Fc fusion used for the generation of variant ENPP1-Fc proteins was ENPP1 (190-925)-hFc, and is shown in Example 1 above as SEQ ID NO: 9.

Various substitution mutations were introduced into the background ENPP1-Fc fusion protein. Based on the residues cleaved by the protease, the majority of mutations were made in residues 816, 817, or 818 relative to SEQ ID NO: 1. Mutations were generated in the ENPP1 nuclease domain by PCR mutagenesis. After PCR mutagenesis, fragments were purified through a Qiagen column, digested, and gel purified. These fragments were ligated into an expression vector such that upon ligation it created a fusion chimera with human IgG1. Following transformation, colonies were picked and DNA was isolated. All mutants were sequence verified.

Accordingly, a soluble ENPP1 fusion protein that lacks both SMB1 and SMB2 domain of ENPP1 with an R818H substitution relative to SEQ ID NO: 1 fused to a human Fc domain with a linker (comprising a leucine, isoleucine, and asparagine) in-between was constructed. This construct is referred to as ENPP1 (190-925)R818H-hFc.

ENPP1 (190-925)R818H-hFc is shown in Table 1 as SEQ ID NO: 11 (with the linker underlined) as purified from CHO cell lines.

The ENPP1 (190-925)R818H-hFc protein expressed in CHO cell lines using a SP(2) leader sequence has the unprocessed amino acid sequence as shown in SEQ ID NO: 12 (Table 1).

The nucleotide sequence encoding the unprocessed amino acid sequence for ENPP1(190-925)R818H-hFc (SEQ ID NO: 12) is shown as SEQ ID NO: 15 in Table 1.

N-terminal sequencing of the CHO-cell produced material revealed a major sequence of —WVEEPC indicating cleavage at SRA-KS (in between the serine (S) and trypto-phan (W) at residues 189 and 190, respectively, with respect to SEQ ID NO: 1).

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Following purification of the protein, the catalytic activity of the ENPP1 (190-925) R818H-hFc protein was evaluated using pNP-TMP as a chromogenic substrate and it was determined that the R818H substitution relative to SEQ ID NO: 1 did not affect ENPP1 enzymatic activity. Additionally, proteolytic cleavage in the nuclease domain was significantly decreased in the ENPP1(190-925) R818H-hFc protein as compared to ENPP1(190-925)-hFc.

Example 3. Generation of ENPP1 Fusion Polypeptides with Additional N-Linked Glycosylation Sites Specific mutations may be selected so as to introduce or eliminate one or more glycosylation sites within human ENPP1. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites).

Introduction of an 1332T substitution mutation, with respect to SEQ ID NO: 1, introduces an N-glycan consensus sequence into an insertion loop within the ENPP1 catalytic domain. Glycans present at residue 332 in the human ENPP1 insertion loop reside close to a catalytic threonine, which is responsible for nucleophilic addition onto the phosphoan-hydride substrate. Surprisingly, when administered to mice, ENPP1-Fc fusion polypeptides comprising 1332T substitutions increased in vivo exposure by 7.7-fold, and increased serum half life by 1600%. In certain non-limiting embodiments, increased biologic exposure induced by the addition of a glycan at position 332 relates to increase biologic absorption and/or circulation of the biologic. In certain non-limiting embodiments, increased biologic exposure induced by the addition of a glycan at position 332 is not due to a gain of function of the enzyme. Purification and preparation of the mutants disclosed herein could be achieved by following the steps outlined above.

Example 4. ENPP1 Anti-Drug Antibody (ADA) Competition Study

An ELISA competition assay was used to identify which domains of a soluble human ENPP1-Fc fusion protein are responsible for binding to anti-drug antibodies (ADA) generated in animal studies. Plasma and serum samples from Rat or NHP dosed with 30 mg/kg ENPP1-Fc in animal studies were treated with acetic acid to separate ADAs from ENPP1-Fc. Acid-treated plasma samples were neutralized and added to an ENPP1-Fc coated plate. After incubation at 37° C. for 3 hours, bound ADAs were eluted with acid treatment, neutralized, and transferred to a second plate to coat overnight. The next day, ENPP1 conjugated to horse-radish peroxidase (ENPP1-HRP) was added to the second plate with or without various competitors. Competitors used in the assay included:

Test Construct 1: an ENPP1-Fc construct containing the entire extracellular domain of human ENPP1.

Test Construct 2: an ENPP1-Fc construct comprising a variant form of the extracellular domain of human ENPP1 that lacks the SMB1 and SMB2 domains (SEQ ID NO: 122).

Test Construct 3: an ENPP1-Fc construct comprising a soluble human ENPP1 in which the catalytic domain was with a substituted with the catalytic domain from the corresponding domain of Cynomolgus monkey ENPP1 (SEQ ID NO: 117).

Test Construct 4: an ENPP1-Fc construct comprising a soluble human ENPP1 in which the nuclease-like domain was substituted with the corresponding domain of cynomolgus monkey ENPP1 (SEQ ID NO: 118).

Test Construct 5: an ENPP1-Fc construct in which the soluble ENPP1 portion of the construct is linked to the Fc portion of the construct via the following amino acid linker sequence: GGGGS (SEQ ID NO:63). (SEQ ID NO: 119).

Control Construct 1 comprising just human IgG1

Control Construct 2: an ENPP1-Fc construct of Construct 1 that has been treated with PNGase F (deglycosylated ENPP1-Fc)

Control Construct 3: a mock treated version of Control Construct 2

Bound ENPP1-HRP was quantified with a colorimetric substrate, TMB (3,3',5,5'-Tetramethylbenzidine) A decrease in ELISA signals indicates competition with ADA-bound ENPP1-HRP.

Compared to the negative control (no competitor), adding unlabeled ENPP1-Fc Test Construct 1 in a 1:1 ratio with ENPP1-HRP results in a roughly 50% drop in signal. In the NHP samples, Control Construct 2 competed for ADA binding as effectively as ENPP1, indicating that the ADAs do not specifically bind to glycans present on glycosylated ENPP1. Effective competition (~50% reduction in signals) was also observed for Test Constructs 3, 4, and 5, suggesting that the ENPP1 catalytic, nuclease-like, and linker domains do not contain the major binding sites for ADAs. In both rat and NHP samples, human IgG1 (Control Construct 1) did not cause a decrease in signals indicating that the ADAs do not bind to the Fc domain of ENPP1-Fc. Surprisingly, addition of Test Construct 2 to the competition assay led to a ~20% decrease in ELISA signals, indicating that removal of the SMB1 and SMB2 domains of ENPP1 caused a marked decrease in the ability to compete with ENPP1-HRP for ADA binding. These data indicate that the ENPP1 SMB1 and SMB2 domains contain the major binding sites for ADAs, responsible for ADA responses in the animal studies.

Example 5. Single Dose PK/PD Assessment of Various ENPP1-Fc Constructs

The activity of various ENPP1-Fc constructs and the associated PPi levels in vivo were evaluated over 360 hours using 3 test constructs. C57BI/6J-ENPP1$^{asj}$/GrsrJ mice, approximately 6 weeks of age, on normal diet were used in the study. Mice were randomized into 9 groups, three groups of 6 mice for each test article, so as to stagger collection time points as shown in the table. Animals were given a single subcutaneous 2 mg/kg dose on study day 1 of various competitors:

Test Construct 5: an ENPP1-Fc construct in which the soluble ENPP1 portion of the construct is linked to the Fc portion of the construct via the following amino acid linker sequence: GGGGS (SEQ ID NO:63) (SEQ ID NO: 119).

Test Construct 6: an ENPP1-Fc construct comprising a variant form of the extracellular domain of human ENPP1 in which the catalytic domain of the ENPP1 portion comprises an 1332T substitution and the Fc domain comprises a triple mutation (M252Y, S254T, T256E) (SEQ ID NO: 120).

Test Construct 7: an ENPP1-Fc construct comprising a variant form of the extracellular domain of human ENPP1 that lacks the SMB1 and SMB2 domains, and in which the catalytic domain of the ENPP1 portion comprises a I332T substitution and the Fc domain comprises a triple mutation (M252Y, S254T, T256E) (SEQ ID NO: 121).

All mice received 40 gfanimal of GK 1.5 (an immunosuppresant) on study day 1 and 25 μg/animal on study days 6 and 12. Samples were obtained at different time points to measure plasma ENPP1 activities and PPi levels as shown in Table 2 below. IDC-23 T2

TABLE 2

| Test Construct | Group | n | Pre-dose | 24 hrs | 72 hrs | 144 hrs | 216 hrs | 360 hrs |
|---|---|---|---|---|---|---|---|---|
| Test Construct 5 | 1 | 6 | X | | | X | | |
| | 2 | 6 | | X | | | X | |
| | 3 | 6 | | | X | | | X |
| Test Construct 6 | 4 | 6 | X | | | X | | |
| | 5 | 6 | | X | | | X | |
| | 6 | 6 | | | X | | | X |
| Test Construct 7 | 7 | 6 | X | | | X | | |
| | 8 | 6 | | X | | | X | |
| | 9 | 6 | | | X | | | X |

ENPP1 activity levels peaked at the 24 hours and declined at later time points in all animals (FIG. 9A). Mice dosed with Test Construct 5 showed the lowest ENPP1 activity levels at 24 hours and faster clearance rate. The activity levels in Test Construct 5-dosed animals went back to the baseline by the 216-hour timepoint. Compared to Test Construct 5, single dose of Test Construct 7 led to higher ENPP1 activity at all time points except the terminal one. Mice dosed with Test Construct 6 showed the highest ENPP1 activity at 24 hours and extended the half-life. The ENPP1 activity levels in Test Construct 6-dosed animals remained elevated at 360 hours.

Dosing with all constructs resulted in an elevation in PPi levels compared to the pre-dose baseline (FIG. 9B). In all groups the PPi elevation lasted at least to the 216-hour timepoint. Consistent with the ENPP1 activity data, PPi levels in animal dosed with Test Construct 6 or Test Construct 7 were higher than the levels in the Test Construct 5 group at timepoints later than 24 hours. PPi levels remained elevated at 360 hours in animals dosed with Test Construct 6 while the other two groups dropped to near baseline levels.

Example 6. Evaluation of In Vivo PPI and Tissue Calcification Levels with ENPP1-Fc Treatment PPi and tissue calcification of the heart, aorta, kidney, and spleen were evaluated in mice treated with vehicle or various ENPP1-Fc constructs (Test Construct 5, Test Construct 6, or Test Construct 7). 2-3 weeks old Enpp1$^{asj,asji}$ mice fed acceleration diet throughout gestation were randomly assigned into 5 groups. Vehicle or ENPP1-Fc variants (Test Construct 5, Test Construct 6, or Test Construct 7) at 1 mg/kg were administered subcutaneously once a week for 4 weeks. Age-matched WT littermates were dosed with vehicle as control. Plasma PPi and calcium content in multiple tissues including heart/aorta, kidney, liver, lungs, spleen, and vibrissae were measured at the end of the study.

Figure 10B:
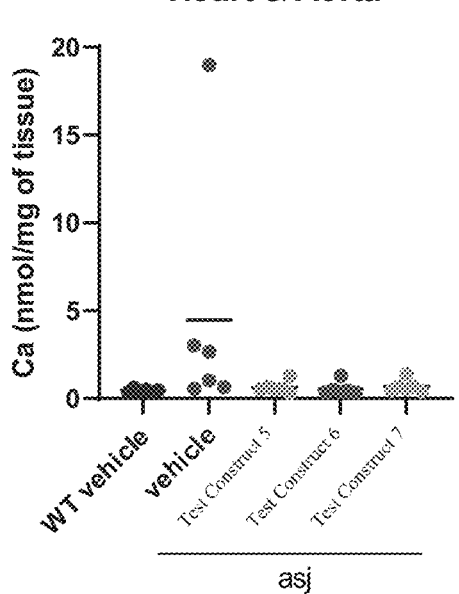
Figure 10C:
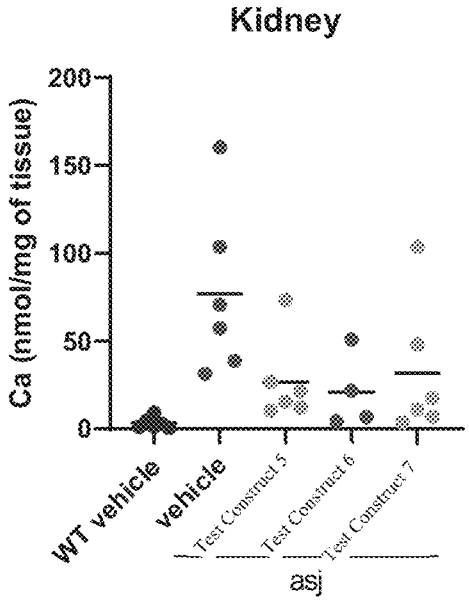
Figure 10D:
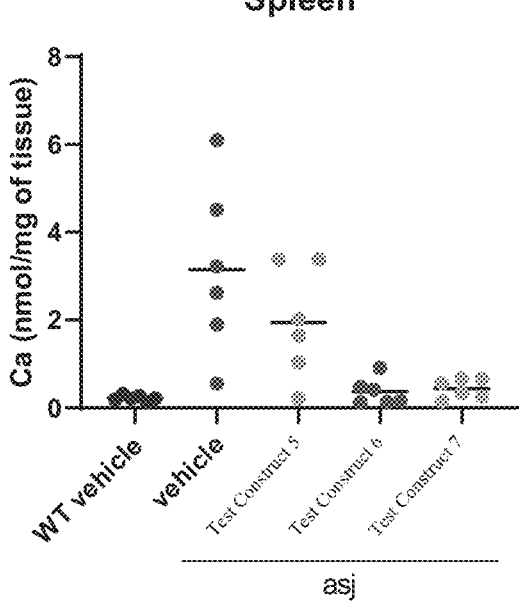

Mutant mice treated with vehicle showed nearly undetectable levels of PPi (FIG. 10A). PPi concentrations were roughly 2 pM in animals dosed with Test Construct 5, while dosing with Test Construct 6 or Test Construct 7 elevated PPi to 8 pM and 10 pM respectively. Animals dosed with Test Construct 6 or Test Construct 7 showed similar, or better, prevention of tissue calcification in heart and aorta, kidneys and spleen, compared to animals dosed with vehicle (FIG. 10B, FIG. 10C, and FIG. 10D).

Example 7. Comparison of Aggregation Levels in ENPP1-Fc Polypeptides Comprising or Lacking SMB Domains The aggregation of ENPP1-Fc polypeptides comprising (Test Construct 5) or lacking (Test Construct 2) SMB domains were compared. Test Construct 2 and Test Construct 5 were transiently expressed in TunaCHO™ cells purified with MabSelect SuRe resin, and dialyzed into the formulation buffer (20 mM histidine, 100 mM Arginine, 50 mM NaCl. 1 mM ZnCl$_2$ pH 6.0). Proteins were concentrated to roughly equivalent concentrations (Test Construct 2-22 mg/mL and Test Construct 5-22.6 mg/mL). Samples were incubated at ambient room temperature with or without 100 mM DTT for either 15 days (Test Construct 2) or 13 days (Test Construct 5) before imaging. Within 2 days, DTT-treated samples had solidified, likely due to the aggregation of DTT-denatured proteins. In samples without DTT treatment, a visible precipitant had formed in the Test Construct 5 sample after 13 days while the Test Construct 2 sample, which lacks SMB domains, remained clear out to 15 days (FIG. 11).

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

The invention claimed is:

1. A soluble ectonucleotide pyrophosphatase/phosphodiesterase (ENPP1) polypeptide that lacks both Somatomedin B (SMB) domain 1 and SMB domain 2 of ENPP1, and wherein the soluble ENPP1 polypeptide is at least 90% identical to the amino acid sequence of SEQ ID NO: 121 and the catalytic domain of the ENPP1 portion of the soluble ENPP1 polypeptide comprises a 1332T substitution and the Fc domain comprises a triple mutation (M252Y, S254T, T256E).

2. The soluble ENPP1 polypeptide of claim 1, wherein the soluble ENPP1 polypeptide comprises the amino acid sequence of SEQ ID NO: 121.

3. The soluble ENPP1 polypeptide of claim 1, wherein the polypeptide has reduced ability to homodimerize as compared to the corresponding wild-type soluble ENPP1; and/or
  wherein the polypeptide has reduced affinity for the human insulin receptor (IR) as compared to the corresponding wild-type soluble ENPP1 polypeptide.

4. The soluble ENPP1 polypeptide of claim 1, wherein the ENPP1 polypeptide demonstrates greater proteolytic resistance to a protease than the corresponding wild-type soluble ENPP1 polypeptide.

5. The soluble ENPP1 polypeptide of claim 1, wherein the greater proteolytic resistance of the ENPP1 polypeptide provides a homogenous composition with protein purity increased by about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, or 300% as compared to a corresponding wild-type soluble ENPP1 polypeptide; and/or
  wherein the greater proteolytic resistance of the ENPP1 polypeptide decreases protein cleavage by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, or 300% as compared to the corresponding wild-type soluble ENPP1 polypeptide; and/or
  wherein the protease is trypsin or trypsin-like proteases.

6. The soluble ENPP1 polypeptide according to claim 1, wherein the soluble ENPP1 polypeptide further comprises a heterologous moiety and wherein the heterologous moiety is selected from the group consisting of a glycosylated amino acid, a PEGylated amino acid, a farnesylated amino acid, an acetylated amino acid, a biotinylated amino acid, and a lipid moiety.

* * * * *

SEQUENCE LISTING

Sequence total quantity: 134
SEQ ID NO: 1          moltype = AA   length = 925
FEATURE               Location/Qualifiers
source                1..925
                      mol_type = protein
                      organism = Homo sapiens
SEQUENCE: 1
MERDGCAGGG SRGGEGGRAP REGPAGNGRD RGRSHAAEAP GDPQAAASLL APMDVGEEPL  60
EKAARARTAK DPNTYKVLSL VLSVCVLTTI LGCIFGLKPS CAKEVKSCKG RCFERTFGNC  120
RCDAACVELG NCCLDYQETC IEPEHIWTCN KFRCGEKRLT RSLCACSDDC KDKGDCCINY  180
SSVCQGEKSW VEEPCESINE PQCPAGFETP PTLLFSLDGF RAEYLHTWGG LLPVISKLKK  240
CGTYTKNMRP VYPTKTFPNH YSIVTGLYPE SHGIIDNKMY DPKMNASFSL KSKEKFNPEW  300
YKGEPIWVTA KYQGLKSGTF FWPGSDVEIN GIFPDIYKMY NGSVPFEERI LAVLQWLQLP  360
KDERPHFYTL YLEEPDSSGH SYGPVSSEVI KALQRVDGMV GMLMDGLKEL NLHRCLNLIL  420
ISDHGMEQGS CKKYIYLNKY LGDVKNIKVI YGPAARLRPS DVPDKYYSFN YEGIARNLSC  480
REPNQHFKPY LKHFLPKRLH FAKSDRIEPL TFYLDPQWQL ALNPSERKYC GSGFHGSDNV  540
FSNMQALFVG YGPGFKHGIE ADTFENIEVY NLMCDLLNLT PAPNNGTHGS LNHLLKNPVY  600
TPKHPKEVHP LVQCPFTRNP RDNLGCSCNP SILPIEDFQT QFNLTVAEEK IIKHETLPYG  660
RPRVLQKENT ICLLSQHQFM SGYSQDILMP LWTSYTVDRN DSFSTEDFSN CLYQDFRIPL  720
SPVHKCSFYK NNTKVSYGFL SPPQLNKNSS GIYSEALLTT NIVPMYQSFQ VIWRYFHDTL  780
LRKYAEERNG VNVVSGPVFD FDYDGRCDSL ENLRQKRRVI RNQEILIPTH FFIVLTSCKD  840
TSQTPLHCEN LDTLAFILPH RTDNSESCVH GKHDSSWVEE LLMLHRARIT DVEHITGLSF  900
YQQRKEPVSD ILKLKTHLPT FSQED                                       925

SEQ ID NO: 2          moltype = AA   length = 827
FEATURE               Location/Qualifiers
source                1..827
                      mol_type = protein
                      organism = Homo sapiens
SEQUENCE: 2
PSCAKEVKSC KGRCFERTFG NCRCDAACVE LGNCCLDYQE TCIEPEHIWT CNKFRCGEKR  60
LTRSLCACSD DCKDKGDCCI NYSSVCQGEK SWVEEPCESI NEPQCPAGFE TPPTLLFSLD  120
GFRAEYLHTW GGLLPVISKL KKCGTYTKNM RPVYPTKTFP NHYSIVTGLY PESHGIIDNK  180
MYDPKMNASF SLKSKEKFNP EWYKGEPIWV TAKYQGLKSG TFFWPGSDVE INGIFPDIYK  240
MYNGSVPFEE RILAVLQWLQ LPKDERPHFY TLYLEEPDSS GHSYGPVSSE VIKALQRVDG  300
MVGMLMDGLK ELNLHRCLNL ILISDHGMEQ GSCKKYIYLN KYLGDVKNIK VIYGPAARLR  360
PSDVPDKYYS FNYEGIARNL SCREPNQHFK PYLKHFLPKR LHFAKSDRIE PLTFYLDPQW  420
QLALNPSERK YCGSGFHGSD NVFSNMQALF VGYGPGFKHG IEADTFENIE VYNLMCDLLN  480
LTPAPNNGTH GSLNHLLKNP VYTPKHPKEV HPLVQCPFTR NPRDNLGCSC NPSILPIEDF  540
QTQFNLTVAE EKIIKHETLP YGRPRVLQKE NTICLLSQHQ FMSGYSQDIL MPLWTSYTVD  600
RNDSFSTEDF SNCLYQDFRI PLSPVHKCSF YKNNTKVSYG FLSPPQLNKN SSGIYSEALL  660
TTNIVPMYQS FQVIWRYFHD TLLRKYAEER NGVNVVSGPV FDFDYDGRCD SLENLRQKRR  720
VIRNQEILIP THFFIVLTSC KDTSQTPLHC ENLDTLAFIL PHRTDNSESC VHGKHDSSWV  780
EELLMLHRAR ITDVEHITGL SFYQQRKEPV SDILKLKTHL PTFSQED             827

SEQ ID NO: 3          moltype = AA   length = 736
FEATURE               Location/Qualifiers
source                1..736
                      mol_type = protein
                      organism = Homo sapiens
SEQUENCE: 3
WVEEPCESIN EPQCPAGFET PPTLLFSLDG FRAEYLHTWG GLLPVISKLK KCGTYTKNMR  60
PVYPTKTFPN HYSIVTGLYP ESHGIIDNKM YDPKMNASFS LKSKEKFNPE WYKGEPIWVT  120
AKYQGLKSGT FFWPGSDVEI NGIFPDIYKM YNGSVPFEER ILAVLQWLQL PKDERPHFYT  180
LYLEEPDSSG HSYGPVSSEV IKALQRVDGM VGMLMDGLKE LNLHRCLNLI LISDHGMEQG  240
SCKKYIYLNK YLGDVKNIKV IYGPAARLRP SDVPDKYYSF NYEGIARNLS CREPNQHFKP  300
YLKHFLPKRL HFAKSDRIEP LTFYLDPQWQ LALNPSERKY CGSGFHGSDN VFSNMQALFV  360
GYGPGFKHGI EADTFENIEV YNLMCDLLNL TPAPNNGTHG SLNHLLKNPV YTPKHPKEVH  420
PLVQCPFTRN PRDNLGCSCN PSILPIEDFQ TQFNLTVAEE KIIKHETLPY GRPRVLQKEN  480
TICLLSQHQF MSGYSQDILM PLWTSYTVDR NDSFSTEDFS NCLYQDFRIP LSPVHKCSFY  540
KNNTKVSYGF LSPPQLNKNS SGIYSEALLT TNIVPMYQSF QVIWRYFHDT LLRKYAEERN  600
GVNVVSGPVF DFDYDGRCDS LENLRQKRRV IRNQEILIPT HFFIVLTSCK DTSQTPLHCE  660
NLDTLAFILP HRTDNSESCV HGKHDSSWVE ELLMLHRARI TDVEHITGLS FYQQRKEPVS  720
DILKLKTHLP TFSQED                                                 736

SEQ ID NO: 4          moltype = AA   length = 735
FEATURE               Location/Qualifiers
source                1..735
                      mol_type = protein
                      organism = Mus musculus
SEQUENCE: 4
WVEETCESID TPECPAEFES PPTLLFSLDG FRAEYLHTWG GLLPVISKLK NCGTYTKNMR  60
PMYPTKTFPN HYSIVTGLYP ESHGIIDNKM YDPKMNASFS LKSKEKFNPL WYKGQPIWVT  120
ANHQEVKSGT YFWPGSDVEI DGILPDIYKM YNGSVPFEER ILAVLEWLQL PSHERPHFYT  180
LYLEEPDSSG HSHGPVSSEV IKALQKVDRL VGMLMDGLKD LGLDKCLNLI LISDHGMEQG  240
SCKKYVYLNK YLGDVNNVKV VYGPAARLRP TDVPETYYSF NYEALAKNLS CREPNQHFRP  300
YLKPFLPKRL HFAKSDRIEP LTFYLDPQWQ LALNPSERKY CGSGFHGSDN LFSNMQALFI  360
GYGPAFKHGA EVDSFENIEV YNLMCDLLGL IPAPNNGSHG SLNHLLKKPI YNPSHPKEEG  420

```
FLSQCPIKST SNDLGCTCDP WIVPIKDFEK QLNLTTEDVD DIYHMTVPYG RPRILLKQHR   480
VCLLQQQQFL TGYSLDLLMP LWASYTFLSN DQFSRDDFSN CLYQDLRIPL SPVHKCSYYK   540
SNSKLSYGFL TPPRLNRVSN HIYSEALLTS NIVPMYQSFQ VIWHYLHDTL LQRYAHERNG   600
INVVSGPVFD FDYDGRYDSL EILKQNSRVI RSQEILIPTH FFIVLTSCKQ LSETPLECSA   660
LESSAYILPH RPDNIESCTH GKRESSWVEE LLTLHRARVT DVELITGLSF YQDRQESVSE   720
LLRLKTHLPI FSQED                                                    735

SEQ ID NO: 5              moltype = AA  length = 735
FEATURE                   Location/Qualifiers
source                    1..735
                          mol_type = protein
                          organism = Bos taurus
SEQUENCE: 5
WAEEECDSID EPQCPAGFET PPTLLFSLDG FRAEYLHTWG GLLPVISKLK TCGTYTKNMR   60
PVYPTKTFPN HYSIVTGLYP ESHGIIDNNI YDPQMNANFA LKNKEKFNPE WYKGEPIWLT   120
AKYQGLKTGT FFWPGSDVKI NGIFPDIYKI YNVSVPFEER ILAILKWLQL PKDERPHFYT   180
LYLEEPDSSG HSYGPVSSEV IRALQRVDNM VGMLMDGLKE LNLHRCLNLI LISDHGMEQG   240
SCKKYVYLNK YLGDTKDYKV VYGPAARLRP SDVPDKYYSF DYEGIAKNLS CQEPNQHFKP   300
YLKHFLPKRL HFAKNDRIER LTFYLDPQWQ LALNPSERKY CGGGFHGSDN TFLNMQALFI   360
GYGPGFKHST EVDSFENIEV YNLMCDLLNL TPAPNNGTHG SLNHLLSNPV YTPKHPKEVR   420
PLVQCPFTRA PRESLDCSCD PSILPIVDFQ TQLNLTMAEE KTIKRGALPY GRPRVLQNST   480
VCLLYQHQFV SGYSRDILMP LWTSYTIGRN DSFSTEDFSN CLYQDLRIPL SPVHKCSFYK   540
NNAKLSYGLL SPPQLHKGSS QVYSEALLTT NIVPMYQSFQ VIWHYLHGTL LQRYAEERNG   600
LNVVSGPVFD SDYDGRYDSL ETLKQNSKII RNLEVLIPTH FFLVLTSCKN TSQTPLQCEN   660
LDAMAFILPH KTDNSESCAH GKHESLWVEE LLKLHTARIT DVEHITGLSF YQERKEPISD   720
ILKLKTHLPT FNQED                                                    735

SEQ ID NO: 6              moltype = AA  length = 736
FEATURE                   Location/Qualifiers
source                    1..736
                          mol_type = protein
                          organism = Oryctolagus cuniculus
SEQUENCE: 6
WVEETCENIN EPQCPEGFEM PPTLLFSLDG FRAEYLHTWG GLLPVISKLK KCGTYAKNMR   60
PVYPTKTFPN HYSIVTGLYP ESHGIIDNKM YDPKMNASFS LKSKEKFNPE WYKGEPIWLT   120
AKYQGLRSGT FFWPGSDVKI NGIFPDIYKI YNGSVPFEER ILAILKWLRL PKDERPHFYT   180
LYLEEPDSSG HSYGPVSSEV IKALQRVDNM VGMLMDGLKE LNLHQCLNLI LISDHGMEQG   240
SCKKYIYLNK YLGDTKNIKV IYGPAARLRP SDVPEKYYSF NYENIARNLS CREPNQHFKP   300
YLKHFLPKRL HFAKSDRIEP LTFYLDPQWQ LALSPSERKY CGSGFHGSDN VFSNMQALFV   360
GYGPGFQHGI EVDSFENIEV YNLMCDLLNL TPAPNNGTHG SLNHLLKNPI YTPKHPKEVQ   420
PSVQCPLAGS PRDSLGCSCN PSILPIVDFQ TQFNLTTAEE KNINRASLPY GRPRLLQKKS   480
SVCLLYQHQF VSGYSHDVLM PLWTSYTVNR NDSFSTEDFS NCLYQDLRIS FSPIHNCSFY   540
KNNAKLSYGF LSPPQLSKDS SQIYSEALLT SNIVPMYQSF QVIWRYFHDT LLQRYAEERN   600
SINVVSGPVF DSDYDGRYDS SEALKRNRRV IRNQEILIPT HFFIVITSCK NTSQTPLQCD   660
NLDPLAFILP HRSDNSESCV HEKRESSWIE ELLMMHRARI MDVEHITGLS FYQERKEPVS   720
DILKLKTHLP TVSQED                                                   736

SEQ ID NO: 7              moltype = AA  length = 736
FEATURE                   Location/Qualifiers
source                    1..736
                          mol_type = protein
                          organism = Homo sapiens
SEQUENCE: 7
WVEEPCESIN EPQCPAGFET PPTLLFSLDG FRAEYLHTWG GLLPVISKLK KCGTYTKNMR   60
PVYPTKTFPN HYSIVTGLYP ESHGIIDNKM YDPKMNASFS LKSKEKFNPE WYKGEPIWVT   120
AKYQGLKSGT FFWPGSDVEI NGIFPDIYKM YNGSVPFEER ILAVLQWLQL PKDERPHFYT   180
LYLEEPDSSG HSYGPVSSEV IKALQRVDGM VGMLMDGLKE LNLHRCLNLI LISDHGMEQG   240
SCKKYIYLNK YLGDVKNIKV IYGPAARLRP SDVPDKYYSF NYEGIARNLS CREPNQHFKP   300
YLKHFLPKRL HFAKSDRIEP LTFYLDPQWQ LALNPSERKY CGSGFHGSDN VFSNMQALFV   360
GYGPGFKHGI EADTFENIEV YNLMCDLLNL TPAPNNGTHG SLNHLLKNPV YTPKHPKEVH   420
PLVQCPFTRN PRDNLGCSCN PSILPIEDFQ TQFNLTVAEE KIIKHETLPY GRPRVLQKEN   480
TICLLSQHQF MSGYSQDILM PLWTSYTVDR NDSFSTEDFS NCLYQDFRIP LSPVHKCSFY   540
KNNTKVSYGF LSPPQLNKNS SGIYSEALLT TNIVPMYQSF QVIWRYFHDT LLRKYAEERN   600
GVNVVSGPVF DFDYDGRCDS LENLRQKRRV IRNQEILIPT HFFIVLTSCK DTSQTPLHCE   660
NLDTLAFILP HRTDNSESCV HGKHDSSWVE ELLMLHRARI TDVEHITGLS FYQQRKEPVS   720
DILKLKTHLP TFSQED                                                   736

SEQ ID NO: 8              moltype = AA  length = 736
FEATURE                   Location/Qualifiers
source                    1..736
                          mol_type = protein
                          organism = Papio anubis
SEQUENCE: 8
WVEEPCESIN EPQCPAGFET PPTLLFSLDG FRAEYLHTWG GLLPVISKLK KCGTYTKNMR   60
PVYPTKTFPN HYSIVTGLYP ESHGIIDNKM YDPKMNASFS LKSKEKFNPE WYKGEPIWVT   120
AKYQGLKSGT FFWPGSDVEI NGIFPDIYKM YNGSVPFEER ILAVLQWLQL PKDERPHFYT   180
LYLEEPDSSG HSYGPVSSEV IKALQRVDNM VGMLMDGLKE LNLHRCLNLI LVSDHGMEQG   240
SCKKYIYLNK YLGDVKNIKV IYGPAARLRP SDVPDKYYSF NYEGIARNLS CREPNQHFKP   300
YLKHFLPKRL HFAKSDRIEP LTFYLDPQWQ LALNPSERKY CGSGFHGSDN IFSNMQALFV   360
```

-continued

```
GYGPGFKHGI EVDTFENIEV YNLMCDLLNL TPAPNNGTHG SLNHLLKNPV YTPKHPKEVH   420
PLIQCPFTRN PRDNLGCSCN PSILPIEDFQ TQFNLTVAEE KNIKHETLPY GRPRVLQKKN   480
TICLLSQHQF MSGYSQDILM PLWTSYTVDR NDSFSTEDFS NCLYQDFRIS LSPVHKCSFY   540
KNNTKVSYGF LSPPQLNKNS RGIYSEALLT TNIVPMYQSF QVIWRYFHDT LLRKYAEERN   600
GVNVVSGPVF DFDYDGRYDS LEILRQKRRV IRNQEILIPT HFFIVLTSCK DASQTPLHCE   660
NLDTLAFILP HRTDNSESCL HGKHESSWVE ELLMLHRARI TDVEHITGLS FYQQRKEPVS   720
DILKLKTHLP TFSQED                                                  736

SEQ ID NO: 9            moltype = AA  length = 966
FEATURE                 Location/Qualifiers
REGION                  1..966
                        note = source = /note="Description of Artificial Sequence:
                         Synthetic polypeptide"
source                  1..966
                        mol_type = protein
                        organism = synthetic construct
SEQUENCE: 9
WVEEPCESIN EPQCPAGFET PPTLLFSLDG FRAEYLHTWG GLLPVISKLK KCGTYTKNMR   60
PVYPTKTFPN HYSIVTGLYP ESHGIIDNKM YDPKMNASFS LKSKEKFNPE WYKGEPIWVT   120
AKYQGLKSGT FFWPGSDVEI NGTFPDIYKM YNGSVPFEER ILAVLQWLQL PKDERPHFYT   180
LYLEEPDSSG HSYGPVSSEV IKALQRVDGM VGMLMDGLKE LNLHRCLNLI LISDHGMEQG   240
SCKKYIYLNK YLGDVKNIKV IYGPAARLRP SDVPDKYYSF NYEGIARNLS CREPNQHFKP   300
YLKHFLPKRL HFAKSDRIEP LTFYLDPQWQ LALNPSERKY CGSGFHGSDN VFSNMQALFV   360
GYGPGFKHGI EADTFENIEV YNLMCDLLNL TPAPNNGTHG SLNHLLKNPV YTPKHPKEVH   420
PLVQCPFTRN PRDNLGCSCN PSILPIEDFQ TQFNLTVAEE KIIKHETLPY GRPRVLQKEN   480
TICLLSQHQF MSGYSQDILM PLWTSYTVDR NDSFSTEDFS NCLYQDFRIP LSPVHKCSFY   540
KNNTKVSYGF LSPPQLNKNS SGIYSEALLT TNIVPMYQSF QVIWRYFHDT LLRKYAEERN   600
GVNVVSGPVF DFDYDGRCDS LENLRQKRRV IRNQEILIPT HFFIVLTSCK DTSQTPLHCE   660
NLDTLAFILP HRTDNSESCV HGKHDSSWVE ELLMLHRARI TDVEHITGLS FYQQRKEPVS   720
DILKLKTHLP TFSQEDLIND KTHTCPPCPA PELLGGPSVF LFPPKPKDTL YITREPEVTC   780
VVVDVSHEDP EVKFNWYVDG VEVHNAKTKP REEQYNSTYR VVSVLTVLHQ DWLNGKEYKC   840
KVSNKALPAP IEKTISKAKG QPREPQVYTL PPSREEMTKN QVSLTCLVKG FYPSDIAVEW   900
ESNGQPENNY KTTPPVLDSD GSFFLYSKLT VDKSRWQQGN VFSCSVMHEA LHNHYTQKSL   960
SLSPGK                                                             966

SEQ ID NO: 10           moltype = AA  length = 987
FEATURE                 Location/Qualifiers
REGION                  1..987
                        note = source = /note="Description of Unknown: Unprocessed
                         ENPP1(190-925)-hFc protein sequence"
source                  1..987
                        mol_type = protein
                        organism = unidentified
SEQUENCE: 10
MTRLTVLALL AGLLASSRAK SWVEEPCESI NEPQCPAGFE TPPTLLFSLD GFRAEYLHTW   60
GGLLPVISKL KKCGTYTKNM RPVYPTKTFP NHYSIVTGLY PESHGIIDNK MYDPKMNASF   120
SLKSKEKFNP EWYKGEPIWV TAKYQGLKSS TFFWPGSDVE INGTFPDIYK MYNGSVPFEE   180
RILAVLQWLQ LPKDERPHFY TLYLEEPDSS GHSYGPVSSE VIKALQRVDG MVGMLMDGLK   240
ELNLHRCLNL ILISDHGMEQ GSCKKYIYLN KYLGDVKNIK VIYGPAARLR PSDVPDKYYS   300
FNYEGIARNL SCREPNQHFK PYLKHFLPKR LHFAKSDRIE PLTFYLDPQW QLALNPSERK   360
YCGSGFHGSD NVFSNMQALF VGYGPGFKHG IEADTFENIE VYNLMCDLLN LTPAPNNGTH   420
GSLNHLLKNP VYTPKHPKEV HPLVQCPFTR NPRDNLGCSC NPSILPIEDF QTQFNLTVAE   480
EKIIKHETLP YGRPRVLQKE NTICLLSQHQ FMSGYSQDIL MPLWTSYTVD RNDSFSTEDF   540
SNCLYQDFRI PLSPVHKCSF YKNNTKVSYG FLSPPQLNKN SSGIYSEALL TTNIVPMYQS   600
FQVIWRYFHD TLLRKYAEER NGVNVVSGPV FDFDYDGRCD SLENLRQKRR VIRNQEILIP   660
THFFIVLTSC KDTSQTPLHC ENLDTLAFIL PHRTDNSESC VHGKHDSSWV EELLMLHRAR   720
ITDVEHITGL SFYQQRKEPV SDILKLKTHL PTFSQEDLIN DKTHTCPPCP APELLGGPSV   780
FLFPPKPKDT LYITREPEVT CVVVDVSHED PEVKFNWYVD GVEVHNAKTK PREEQYNSTY   840
RVVSVLTVLH QDWLNGKEYK CKVSNKALPA PIEKTISKAK GQPREPQVYT LPPSREEMTK   900
NQVSLTCLVK GFYPSDIAVE WESNGQPENN YKTTPPVLDS DGSFFLYSKL TVDKSRWQQG   960
NVFSCSVMHE ALHNHYTQKS LSLSPGK                                      987

SEQ ID NO: 11           moltype = AA  length = 966
FEATURE                 Location/Qualifiers
REGION                  1..966
                        note = source = /note="Description of Artificial Sequence:
                         Synthetic polypeptide"
source                  1..966
                        mol_type = protein
                        organism = synthetic construct
SEQUENCE: 11
WVEEPCESIN EPQCPAGFET PPTLLFSLDG FRAEYLHTWG GLLPVISKLK KCGTYTKNMR   60
PVYPTKTFPN HYSIVTGLYP ESHGIIDNKM YDPKMNASFS LKSKEKFNPE WYKGEPIWVT   120
AKYQGLKSGT FFWPGSDVEI NGTFPDIYKM YNGSVPFEER ILAVLQWLQL PKDERPHFYT   180
LYLEEPDSSG HSYGPVSSEV IKALQRVDGM VGMLMDGLKE LNLHRCLNLI LISDHGMEQG   240
SCKKYIYLNK YLGDVKNIKV IYGPAARLRP SDVPDKYYSF NYEGIARNLS CREPNQHFKP   300
YLKHFLPKRL HFAKSDRIEP LTFYLDPQWQ LALNPSERKY CGSGFHGSDN VFSNMQALFV   360
GYGPGFKHGI EADTFENIEV YNLMCDLLNL TPAPNNGTHG SLNHLLKNPV YTPKHPKEVH   420
PLVQCPFTRN PRDNLGCSCN PSILPIEDFQ TQFNLTVAEE KIIKHETLPY GRPRVLQKEN   480
```

```
TICLLSQHQF MSGYSQDILM PLWTSYTVDR NDSFSTEDFS NCLYQDFRIP LSPVHKCSFY   540
KNNTKVSYGF LSPPQLNKNS SGIYSEALLT TNIVPMYQSF QVIWRYFHDT LLRKYAEERN   600
GVNVVSGPVF DFDYDGRCDS LENLRQKRHV IRNQEILIPT HFFIVLTSCK DTSQTPLHCE   660
NLDTLAFILP HRTDNSESCV HGKHDSSWVE ELLMLHRARI TDVEHITGLS FYQQRKEPVS   720
DILKLKTHLP TFSQEDLIND KTHTCPPCPA PELLGGPSVF LFPPKPKDTL YITREPEVTC   780
VVVDVSHEDP EVKFNWYVDG VEVHNAKTKP REEQYNSTYR VVSVLTVLHQ DWLNGKEYKC   840
KVSNKALPAP IEKTISKAKG QPREPQVYTL PPSREEMTKN QVSLTCLVKG FYPSDIAVEW   900
ESNGQPENNY KTTPPVLDSD GSFFLYSKLT VDKSRWQQGN VFSCSVMHEA LHNHYTQKSL   960
SLSPGK                                                              966

SEQ ID NO: 12           moltype = AA   length = 987
FEATURE                 Location/Qualifiers
REGION                  1..987
                        note = source = /note="Description of Artificial Sequence:
                         Synthetic polypeptide"
source                  1..987
                        mol_type = protein
                        organism = synthetic construct
SEQUENCE: 12
MTRLTVLALL AGLLASSRAK SWVEEPCESI NEPQCPAGFE TPPTLLFSLD GFRAEYLHTW   60
GGLLPVISKL KKCGTYTKNM RPVYPTKTFP NHYSIVTGLY PESHGIIDNK MYDPKMNASF   120
SLKSKEKFNP EWYKGEPIWV TAKYQGLKSG TFFWPGSDVE INGTFPDIYK MYNGSVPFEE   180
RILAVLQWLQ LPKDERPHFY TLYLEEPDSS GHSYGPVSSE VIKALQRVDG MVGMLMDGLK   240
ELNLHRCLNL ILISDHGMEQ GSCKKYIYLN KYLGDVKNIK VIYGPAARLR PSDVPDKYYS   300
FNYEGIARNL SCREPNQHFK PYLKHFLPKR LHFAKSDRIE PLTFYLDPQW QLALNPSERK   360
YCGSGFHGSD NVFSNMQALF VGYGPGFKHG IEADTFENIE VYNLMCDLLN LTPAPNNGTH   420
GSLNHLLKNP VYTPKHPKEV HPLVQCPFTR NPRDNLGCSC NPSILPIEDF QTQFNLTVAE   480
EKIIKHETLP YGRPRVLQKE NTICLLSQHQ FMSGYSQDIL MPLWTSYTVD RNDSFSTEDF   540
SNCLYQDFRI PLSPVHKCSF YKNNTKVSYG FLSPPQLNKN SSGIYSEALL TTNIVPMYQS   600
FQVIWRYFHD TLLRKYAEER NGVNVVSGPV FDFDYDGRCD SLENLRQKRH VIRNQEILIP   660
THFFIVLTSC KDTSQTPLHC ENLDTLAFIL PHRTDNSESC VHGKHDSSWV EELLMLHRAR   720
ITDVEHITGL SFYQQRKEPV SDILKLKTHL PTFSQEDLIN DKTHTCPPCP APELLGGPSV   780
FLFPPKPKDT LYITREPEVT CVVVDVSHED PEVKFNWYVD GVEVHNAKTK PREEQYNSTY   840
RVVSVLTVLH QDWLNGKEYK CKVSNKALPA PIEKTISKAK GQPREPQVYT LPPSREEMTK   900
NQVSLTCLVK GFYPSDIAVE WESNGQPENN YKTTPPVLDS DGSFFLYSKL TVDKSRWQQG   960
NVFSCSVMHE ALHNHYTQKS LSLSPGK                                       987

SEQ ID NO: 13           moltype = AA   length = 227
FEATURE                 Location/Qualifiers
source                  1..227
                        mol_type = protein
                        organism = Homo sapiens
SEQUENCE: 13
DKTHTCPPCP APELLGGPSV FLFPPKPKDT LYITREPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 14           moltype = DNA   length = 2985
FEATURE                 Location/Qualifiers
misc_feature            1..2985
                        note = source = /note="Description of Unknown: ENPP1-Fc
                         nucleotide sequence"
source                  1..2985
                        mol_type = other DNA
                        organism = unidentified
SEQUENCE: 14
ggtaccgcca ccatgacaag actgacagtg ctggctctgc tggccggact gttggcctct   60
tctagagcta agtcctgggt tgaagaaccc tgcgagtcca tcaacgagcc tcagtgtcct   120
gccggcttcg agacacctcc tactctgctg ttctccctgg atggcttcag agccgagtac   180
ctgcatactt ggggaggcct gctgccagtg atctccaagc tgaagaagtg cggcacctac   240
accaagaaca tgaggcctgt gtaccctacc aagacattcc ccaaccacta ctccatcgtg   300
accggcctga tcctgagag ccacggcatc atcgacaaca agatgtacga ccccaagatg   360
aacgcctcct tcagcctgaa gtccaaagag aagttcaacc ccgagtggta taagggcgag   420
cctatctggg tcaccgctaa gtaccaggga ctgaagtctg gcaccttctt ttggcctggc   480
tccgacgtgg aaatcaacgg caccttcccc gacatctata agatgtacaa cggctccgtg   540
cctttcgagg aacgcattct ggctgttctg cagtggctgc agctgcctaa ggatgagagg   600
cctcacttct acaccctgta cctggaagaa cctgactcct ccggccactc ttatggccct   660
gtgtcctctg aagtgatcaa ggccctgcag cgagtggacg gaatggtcgg aatgctgatg   720
gacggcctga agagctgaa cctgcacaga tgcctgaacc tgatcctgat ctccgaccac   780
ggcatggaac aggggagctg caagaagtac atctacctga caagtacct gggcgacgtg   840
aagaacatca agtgatcta cggcccagcc gccagactga ggcttctga tgtgcctgac   900
aagtactact ccttcaacta cgagggaatc gcccggaacc tgtcctgcag agagcctaac   960
cagcacttca gccctacct gaagcacttt ctgcctaagc gactggacgg cgtcccgg cagcagtct   1020
gacagaatcg agccctgac cttctatctg accctcagt ggcagctggc cctgaatcct   1080
agcgagagaa agtactgtgg ctccggcttc acggctccg acaacgtgtt ctctaatatg   1140
caggccctgt cgtcggcta cggccctggc tttaaacacg gcatcgaggc cgacaccttc   1200
gagaacatca aggtgtacaa tctgatgtgt gacctgctga atctgacccc tgctcctaac   1260
aacggcacc acgatctct gaaccatctg ctgaagaatc ccgtgtacac ccctaagcac   1320
```

-continued

```
cccaaagagg ttcaccctct ggtccagtgt cctttcacca gaaatcctcg ggacaacctg   1380
ggctgctctt gcaacccttc tatcctgcct atcgaggact ttcagaccca gttcaacctg   1440
accgtggccg aggaaaagat catcaagcac gagacactgc cctacggcag acctagagtg   1500
ctgcagaaag agaacaccat ctgcctgctg tcccagcacc agttcatgtc cggctactcc   1560
caggacatcc tgatgcctct gtggacctcc tacaccgtgg accggaacga tagcttctcc   1620
accgaggact tcagcaactg cctgtaccag gatttcagaa tccctctgag ccccgtgcac   1680
aagtgcagct tctacaagaa caacaccaag gtgtcctacg gcttcctgtc tcctccacag   1740
ctgaacaaga actccagcgg catctactct gaggccctgc tgaccaccaa catcgtgccc   1800
atgtaccagt ccttccaagt gatctggcgg tacttccaca caccctgct gaggaagtac   1860
gccgaagaaa gaaacggcgt gaacgtggtg tctggccccg tgttcgactt cgactacgac   1920
ggcagatgcg actctctgga aaacctgcgg cagaaaagac gagtgatccg gaatcaagag   1980
atcctgattc ctacacactt ctttatcgtg ctgaccagct gcaaggatac ctctcagacc   2040
cctctgcact gcgagaatct ggacaccctg gccttcattc tgcctcacag aaccgacaac   2100
tccgagtcct gtgtgcacgg caagcacgac tcctcttggg tcgaagaact gctgatgctg   2160
caccgggcca gaatcaccga tgtggaacac atcaccggcc tgagcttcta ccagcagcgg   2220
aaagaacctg tgtccgatat cctgaagctg aaaaaccatc tgccaacctt cagccaagag   2280
gacctgatca acgacaagac ccacacctgt cctccatgtc ctgctccaga actgctcgga   2340
ggcccctctg tgttcctgtt tccacctaag ccaaaggaca cactgtacat cactcgggag   2400
cctgaagtga cctgcgtggt ggtggatgtg tctcacgaag atcccgaagt caagttcaat   2460
tggtacgtgg acggcgtgga agtgcacaac gccaagacca gcctagaga ggaacagtac   2520
aactccacct acagagtggt gtccgtgctg actgtgctgc accaggattg gctgaacggc   2580
aaagagtaca agtgcaaagt gtccaacaag gctctgccg ctcctatcga aagaccatc    2640
tccaaggcta agggccagcc tcgggaacct caggtttaca ccctgcctcc atctcgggaa   2700
gagatgacca gaaccaggt gtccctgacc tgcctggtca agggcttcta cccttccgat   2760
atcgccgtga atgggagtc caatggccag cctgagaaca actacaagac aacccctcct   2820
gtgctggaca gcgacggctc attcttcctg tactctaagc tgacagtgga caagtcccgg   2880
tggcagcaag gcaatgtgtt ttcctgctct gtgatgcacg aggccctcca caatcactac   2940
acccagaagt ccctgtctct gtcccctggc aaatgatagc tcgag               2985
```

SEQ ID NO: 15          moltype = DNA   length = 2985
FEATURE                Location/Qualifiers
misc_feature           1..2985
                       note = source = /note="Description of Unknown: ENPP1-Fc
                        nucleotide sequence"
source                 1..2985
                       mol_type = other DNA
                       organism = unidentified
SEQUENCE: 15

```
ggtaccgcca ccatgacaag actgacagtg ctggctctgc tggccggact gttggcctct   60
tctagagcta agtcctgggt tgaagaaccc tgcgagtcca tcaacgagcc tcagtgtcct   120
gccggcttcg agacacctcc tactctgctg ttctccctgg atggcttcag agccgagtac   180
ctgcatactt ggggaggcct gctgccagtg atctccaagc tgaagaagtg cggcacctac   240
accaagaaca tgaggcctgt gtaccctacc aagacattcc ccaaccacta ctccatcgtg   300
accggcctgt atcctgagag ccacggcatc atcgacaaca agatgtacga ccccaagatg   360
aacgcctcct tcagcctgaa gtccaaagag aagttcaacc ccgagtggta taagggcgag   420
cctatctggg tcaccgctaa gtaccaggga ctgaagtctg gcaccttctt ttggcctggc   480
tccgacgtgg aaatcaacgg caccttcccc gacatctata agatgtacaa cggctccgtg   540
cctttcgagg aacgcattct ggctgttctg cagtggctgc agctgcctaa ggatgagagg   600
cctcacttct acaccctgta cctggaagaa cctgactcct ccggccactc ttatggccct   660
gtgtcctctg aagtgatcaa ggccctgcag cgagtggacg gaatggtcgg aatgctgatg   720
gacggcctga aagagctgaa cctgcacaga tgcctgaacc tgatcctgat ctccgaccac   780
ggcatggaac aggggagctg caagaagtac atctacctga acaagtacct gggcgacgtg   840
aagaacatca aagtgatcta cggcccagcc gccagactga ggccttctga tgtgcctgac   900
aagtactact ccttcaacta cgagggaatc gcccggaacc tgtcctgcag agagcctaac   960
cagcactca agccctacct gaagcacttt ctgcctaacg ggctgcactt cgccaagtct   1020
gacagaatcg agcccctgac cttctatctg gaccctcagt ggcagctggc cctgaatcct   1080
agcgagagaa agtactgtgg ctccggcttc cacggctccg acaacgtgtt ctctaatatg   1140
caggccctgt tcgtcggcta cggccctggc tttaaacacg gcatcgaggc cgacaccttc   1200
gagaacatcg aggtgtacaa tctgatgtgt gacctgctga tctgaccccc tgctcctaac   1260
aacggcaccc acggatctct gaaccatctg ctgaagaatc ccgtgtacac ccctaagcac   1320
cccaaagagg ttcaccctct ggtccagtgt cctttcacca gaaatcctcg ggacaacctg   1380
ggctgctctt gcaacccttc tatcctgcct atcgaggact ttcagaccca gttcaacctg   1440
accgtggccg aggaaaagat catcaagcac gagacactgc cctacggcag acctagagtg   1500
ctgcagaaag agaacaccat ctgcctgctg tcccagcacc agttcatgtc cggctactcc   1560
caggacatcc tgatgcctct gtggacctcc tacaccgtgg accggaacga tagcttctcc   1620
accgaggact tcagcaactg cctgtaccag gatttcagaa tccctctgag ccccgtgcac   1680
aagtgcagct tctacaagaa caacaccaag gtgtcctacg gcttcctgtc tcctccacag   1740
ctgaacaaga actccagcgg catctactct gaggccctgc tgaccaccaa catcgtgccc   1800
atgtaccagt ccttccaagt gatctggcgg tacttccaca cacccctgct gaggaagtac   1860
gccgaagaaa gaaacggcgt gaacgtggtg tctggccccg tgttcgactt cgactacgac   1920
ggcagatgcg actctctgga aaacctgcgg cagaaaagac acgtgatccg gaatcaagag   1980
atcctgattc ctacacactt ctttatcgtg ctgaccagct gcaaggatac ctctcagacc   2040
cctctgcact gcgagaatct ggacaccctg gccttcattc tgcctcacag aaccgacaac   2100
tccgagtcct gtgtgcacgg caagcacgac tcctcttggg tcgaagaact gctgatgctg   2160
caccgggcca gaatcaccga tgtggaacac atcaccggcc tgagcttcta ccagcagcgg   2220
aaagaacctg tgtccgatat cctgaagctg aaaaaccatc tgccaacctt cagccaagag   2280
gacctgatca acgacaagac ccacacctgt cctccatgtc ctgctccaga actgctcgga   2340
ggcccctctg tgttcctgtt tccacctaag ccaaaggaca cactgtacat cactcgggag   2400
cctgaagtga cctgcgtggt ggtggatgtg tctcacgaag atcccgaagt caagttcaat   2460
```

-continued

```
tggtacgtgg acggcgtgga agtgcacaac gccaagacca agcctagaga ggaacagtac    2520
aactccacct acagagtggt gtccgtgctg actgtgctgc accaggattg gctgaacggc    2580
aaagagtaca agtgcaaagt gtccaacaag gctctgcccg ctcctatcga aaagaccatc    2640
tccaaggcta agggccagcc tcgggaacct caggtttaca ccctgcctcc atctcgggaa    2700
gagatgacca agaaccaggt gtccctgacc tgcctggtca agggcttcta cccttccgat    2760
atcgccgtgg aatgggagtc caatggccag cctgagaaca actacaagac aaccccctcct   2820
gtgctggaca cgacggctc attcttcctg tactctaagc tgacagtgga caagtcccgg     2880
tggcagcaag gcaatgtgtt ttcctgctct gtgatgcacg aggccctcca caatcactac    2940
acccagaagt ccctgtctct gtccctggc aaatgatagc tcgag                     2985
```

```
SEQ ID NO: 16                moltype = AA   length = 227
FEATURE                      Location/Qualifiers
source                       1..227
                             mol_type = protein
                             organism = Homo sapiens
SEQUENCE: 16
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227
```

```
SEQ ID NO: 17                moltype = AA   length = 24
FEATURE                      Location/Qualifiers
VARIANT                      23
                             note = /replace=" "
VARIANT                      24
                             note = /replace=" "
SITE                         1..24
                             note = /note="Variant residues given in the sequence have
                              no preference with respect to those in the annotations for
                              variant positions"
REGION                       1..24
                             note = source = /note="See specification as filed for
                              detailed description of substitutions and preferred
                              embodiments"
source                       1..24
                             mol_type = protein
                             organism = Homo sapiens
SEQUENCE: 17
MTSKFLLVSF ILAALSLSTT FSLQ                                           24
```

```
SEQ ID NO: 18                moltype = AA   length = 22
FEATURE                      Location/Qualifiers
source                       1..22
                             mol_type = protein
                             organism = Homo sapiens
SEQUENCE: 18
MRGPAVLLTV ALATLLAPGA GA                                             22
```

```
SEQ ID NO: 19                moltype = AA   length = 20
FEATURE                      Location/Qualifiers
source                       1..20
                             mol_type = protein
                             organism = Homo sapiens
SEQUENCE: 19
MRGPAVLLTV ALATLLAPGA                                                20
```

```
SEQ ID NO: 20                moltype = AA   length = 19
FEATURE                      Location/Qualifiers
source                       1..19
                             mol_type = protein
                             organism = Homo sapiens
SEQUENCE: 20
IISLFTFAVG VNICLGFTA                                                 19
```

```
SEQ ID NO: 21                moltype =    length =
SEQUENCE: 21
000
```

```
SEQ ID NO: 22                moltype =    length =
SEQUENCE: 22
000
```

```
SEQ ID NO: 23                moltype =    length =
SEQUENCE: 23
000
```

```
SEQ ID NO: 24                moltype =    length =
SEQUENCE: 24
```

-continued

```
000

SEQ ID NO: 25             moltype =   length =
SEQUENCE: 25
000

SEQ ID NO: 26             moltype =   length =
SEQUENCE: 26
000

SEQ ID NO: 27             moltype = AA  length = 4
FEATURE                   Location/Qualifiers
REGION                    1..4
                          note = source = /note="Description of Artificial Sequence:
                           Synthetic peptide"
source                    1..4
                          mol_type = protein
                          organism = synthetic construct
SEQUENCE: 27
GGGA                                                                     4

SEQ ID NO: 28             moltype = AA  length = 4
FEATURE                   Location/Qualifiers
REGION                    1..4
                          note = source = /note="Description of Artificial Sequence:
                           Synthetic peptide"
source                    1..4
                          mol_type = protein
                          organism = synthetic construct
SEQUENCE: 28
GGGS                                                                     4

SEQ ID NO: 29             moltype = AA  length = 4
FEATURE                   Location/Qualifiers
REGION                    1..4
                          note = source = /note="Description of Artificial Sequence:
                           Synthetic peptide"
source                    1..4
                          mol_type = protein
                          organism = synthetic construct
SEQUENCE: 29
GGGG                                                                     4

SEQ ID NO: 30             moltype = AA  length = 5
FEATURE                   Location/Qualifiers
REGION                    1..5
                          note = source = /note="Description of Artificial Sequence:
                           Synthetic peptide"
source                    1..5
                          mol_type = protein
                          organism = synthetic construct
SEQUENCE: 30
GGGGA                                                                    5

SEQ ID NO: 31             moltype = AA  length = 5
FEATURE                   Location/Qualifiers
REGION                    1..5
                          note = source = /note="Description of Artificial Sequence:
                           Synthetic peptide"
source                    1..5
                          mol_type = protein
                          organism = synthetic construct
SEQUENCE: 31
GGGGS                                                                    5

SEQ ID NO: 32             moltype = AA  length = 5
FEATURE                   Location/Qualifiers
REGION                    1..5
                          note = source = /note="Description of Artificial Sequence:
                           Synthetic peptide"
source                    1..5
                          mol_type = protein
                          organism = synthetic construct
SEQUENCE: 32
GGGGG                                                                    5

SEQ ID NO: 33             moltype = AA  length = 4
FEATURE                   Location/Qualifiers
REGION                    1..4
```

```
                        note = source = /note="Description of Artificial Sequence:
                         Synthetic peptide"
source                  1..4
                        mol_type = protein
                        organism = synthetic construct
SEQUENCE: 33
GGAG                                                                           4

SEQ ID NO: 34           moltype = AA  length = 4
FEATURE                 Location/Qualifiers
REGION                  1..4
                        note = source = /note="Description of Artificial Sequence:
                         Synthetic peptide"
source                  1..4
                        mol_type = protein
                        organism = synthetic construct
SEQUENCE: 34
GGSG                                                                           4

SEQ ID NO: 35           moltype = AA  length = 4
FEATURE                 Location/Qualifiers
REGION                  1..4
                        note = source = /note="Description of Artificial Sequence:
                         Synthetic peptide"
source                  1..4
                        mol_type = protein
                        organism = synthetic construct
SEQUENCE: 35
AGGG                                                                           4

SEQ ID NO: 36           moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 36
SGGGG                                                                          5

SEQ ID NO: 37           moltype = AA  length = 4
FEATURE                 Location/Qualifiers
REGION                  1..4
                        note = source = /note="Description of Artificial Sequence:
                         Synthetic peptide"
source                  1..4
                        mol_type = protein
                        organism = synthetic construct
SEQUENCE: 37
SGGG                                                                           4

SEQ ID NO: 38           moltype = AA  length = 4
FEATURE                 Location/Qualifiers
REGION                  1..4
                        note = source = /note="Description of Artificial Sequence:
                         Synthetic peptide"
source                  1..4
                        mol_type = protein
                        organism = synthetic construct
SEQUENCE: 38
GAGA                                                                           4

SEQ ID NO: 39           moltype = AA  length = 4
FEATURE                 Location/Qualifiers
REGION                  1..4
                        note = source = /note="Description of Artificial Sequence:
                         Synthetic peptide"
source                  1..4
                        mol_type = protein
                        organism = synthetic construct
SEQUENCE: 39
GSGS                                                                           4

SEQ ID NO: 40           moltype = AA  length = 6
FEATURE                 Location/Qualifiers
REGION                  1..6
                        note = source = /note="Description of Artificial Sequence:
                         Synthetic peptide"
```

-continued

```
source                 1..6
                       mol_type = protein
                       organism = synthetic construct
SEQUENCE: 40
GAGAGA                                                              6

SEQ ID NO: 41          moltype = AA   length = 6
FEATURE                Location/Qualifiers
REGION                 1..6
                       note = source = /note="Description of Artificial Sequence:
                       Synthetic peptide"
source                 1..6
                       mol_type = protein
                       organism = synthetic construct
SEQUENCE: 41
GSGSGS                                                              6

SEQ ID NO: 42          moltype = AA   length = 8
FEATURE                Location/Qualifiers
REGION                 1..8
                       note = source = /note="Description of Artificial Sequence:
                       Synthetic peptide"
source                 1..8
                       mol_type = protein
                       organism = synthetic construct
SEQUENCE: 42
GAGAGAGA                                                            8

SEQ ID NO: 43          moltype = AA   length = 8
FEATURE                Location/Qualifiers
REGION                 1..8
                       note = source = /note="Description of Artificial Sequence:
                       Synthetic peptide"
source                 1..8
                       mol_type = protein
                       organism = synthetic construct
SEQUENCE: 43
GSGSGSGS                                                            8

SEQ ID NO: 44          moltype = AA   length = 10
FEATURE                Location/Qualifiers
REGION                 1..10
                       note = source = /note="Description of Artificial Sequence:
                       Synthetic peptide"
source                 1..10
                       mol_type = protein
                       organism = synthetic construct
SEQUENCE: 44
GAGAGAGAGA                                                          10

SEQ ID NO: 45          moltype = AA   length = 10
FEATURE                Location/Qualifiers
REGION                 1..10
                       note = source = /note="Description of Artificial Sequence:
                       Synthetic peptide"
source                 1..10
                       mol_type = protein
                       organism = synthetic construct
SEQUENCE: 45
GSGSGSGSGS                                                          10

SEQ ID NO: 46          moltype = AA   length = 12
FEATURE                Location/Qualifiers
REGION                 1..12
                       note = source = /note="Description of Artificial Sequence:
                       Synthetic peptide"
source                 1..12
                       mol_type = protein
                       organism = synthetic construct
SEQUENCE: 46
GAGAGAGAGA GA                                                       12

SEQ ID NO: 47          moltype = AA   length = 12
FEATURE                Location/Qualifiers
REGION                 1..12
                       note = source = /note="Description of Artificial Sequence:
                       Synthetic peptide"
source                 1..12
                       mol_type = protein
```

```
                         organism = synthetic construct
SEQUENCE: 47
GSGSGSGSGS GS                                                        12

SEQ ID NO: 48           moltype = AA   length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 48
GGAGGA                                                               6

SEQ ID NO: 49           moltype = AA   length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 49
GGSGGS                                                               6

SEQ ID NO: 50           moltype = AA   length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 50
GGAGGAGGA                                                            9

SEQ ID NO: 51           moltype = AA   length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 51
GGSGGSGGS                                                            9

SEQ ID NO: 52           moltype = AA   length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 52
GGAGGAGGAG GA                                                        12

SEQ ID NO: 53           moltype = AA   length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 53
GGSGGSGGSG GS                                                        12

SEQ ID NO: 54           moltype = AA   length = 4
FEATURE                 Location/Qualifiers
REGION                  1..4
                        note = source = /note="Description of Artificial Sequence:
                         Synthetic peptide"
source                  1..4
                        mol_type = protein
                        organism = synthetic construct
SEQUENCE: 54
```

-continued

```
GGAG                                                        4

SEQ ID NO: 55         moltype = AA  length = 4
FEATURE               Location/Qualifiers
REGION                1..4
                      note = source = /note="Description of Artificial Sequence:
                       Synthetic peptide"
source                1..4
                      mol_type = protein
                      organism = synthetic construct
SEQUENCE: 55
GGSG                                                        4

SEQ ID NO: 56         moltype = AA  length = 4
FEATURE               Location/Qualifiers
REGION                1..4
                      note = source = /note="Description of Artificial Sequence:
                       Synthetic peptide"
source                1..4
                      mol_type = protein
                      organism = synthetic construct
SEQUENCE: 56
GGAG                                                        4

SEQ ID NO: 57         moltype = AA  length = 4
FEATURE               Location/Qualifiers
REGION                1..4
                      note = source = /note="Description of Artificial Sequence:
                       Synthetic peptide"
source                1..4
                      mol_type = protein
                      organism = synthetic construct
SEQUENCE: 57
GGSG                                                        4

SEQ ID NO: 58         moltype = AA  length = 8
FEATURE               Location/Qualifiers
REGION                1..8
                      note = source = /note="Description of Artificial Sequence:
                       Synthetic peptide"
source                1..8
                      mol_type = protein
                      organism = synthetic construct
SEQUENCE: 58
GGAGGGAG                                                    8

SEQ ID NO: 59         moltype = AA  length = 8
FEATURE               Location/Qualifiers
REGION                1..8
                      note = source = /note="Description of Artificial Sequence:
                       Synthetic peptide"
source                1..8
                      mol_type = protein
                      organism = synthetic construct
SEQUENCE: 59
GGSGGGSG                                                    8

SEQ ID NO: 60         moltype = AA  length = 12
FEATURE               Location/Qualifiers
REGION                1..12
                      note = source = /note="Description of Artificial Sequence:
                       Synthetic peptide"
source                1..12
                      mol_type = protein
                      organism = synthetic construct
SEQUENCE: 60
GGAGGGAGGG AG                                              12

SEQ ID NO: 61         moltype = AA  length = 12
FEATURE               Location/Qualifiers
REGION                1..12
                      note = source = /note="Description of Artificial Sequence:
                       Synthetic peptide"
source                1..12
                      mol_type = protein
                      organism = synthetic construct
SEQUENCE: 61
GGSGGGSGGG SG                                              12
```

-continued

```
SEQ ID NO: 62          moltype = AA   length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 62
GGGGA                                                                   5

SEQ ID NO: 63          moltype = AA   length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 63
GGGGS                                                                   5

SEQ ID NO: 64          moltype = AA   length = 15
FEATURE                Location/Qualifiers
REGION                 1..15
                       note = source = /note="Description of Artificial Sequence:
                        Synthetic peptide"
source                 1..15
                       mol_type = protein
                       organism = synthetic construct
SEQUENCE: 64
GGGGAGGGGA GGGGA                                                        15

SEQ ID NO: 65          moltype = AA   length = 15
FEATURE                Location/Qualifiers
REGION                 1..15
                       note = source = /note="Description of Artificial Sequence:
                        Synthetic peptide"
source                 1..15
                       mol_type = protein
                       organism = synthetic construct
SEQUENCE: 65
GGGGSGGGGS GGGGS                                                        15

SEQ ID NO: 66          moltype = AA   length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 66
GGGAG                                                                   5

SEQ ID NO: 67          moltype = AA   length = 6
FEATURE                Location/Qualifiers
REGION                 1..6
                       note = source = /note="Description of Artificial Sequence:
                        Synthetic peptide"
source                 1..6
                       mol_type = protein
                       organism = synthetic construct
SEQUENCE: 67
GGGAGG                                                                  6

SEQ ID NO: 68          moltype = AA   length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 68
GGGAGGG                                                                 7

SEQ ID NO: 69          moltype =    length =
SEQUENCE: 69
```

-continued

```
000

SEQ ID NO: 70          moltype = AA  length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 70
TGGGG                                                                       5

SEQ ID NO: 71          moltype = AA  length = 4
FEATURE                Location/Qualifiers
REGION                 1..4
                       note = source = /note="Description of Artificial Sequence:
                        Synthetic peptide"
source                 1..4
                       mol_type = protein
                       organism = synthetic construct
SEQUENCE: 71
AAAL                                                                        4

SEQ ID NO: 72          moltype = AA  length = 4
FEATURE                Location/Qualifiers
REGION                 1..4
                       note = source = /note="Description of Artificial Sequence:
                        Synthetic peptide"
source                 1..4
                       mol_type = protein
                       organism = synthetic construct
SEQUENCE: 72
AAAK                                                                        4

SEQ ID NO: 73          moltype = AA  length = 4
FEATURE                Location/Qualifiers
REGION                 1..4
                       note = source = /note="Description of Artificial Sequence:
                        Synthetic peptide"
source                 1..4
                       mol_type = protein
                       organism = synthetic construct
SEQUENCE: 73
AAAR                                                                        4

SEQ ID NO: 74          moltype = AA  length = 14
FEATURE                Location/Qualifiers
REGION                 1..14
                       note = source = /note="Description of Artificial Sequence:
                        Synthetic peptide"
source                 1..14
                       mol_type = protein
                       organism = synthetic construct
SEQUENCE: 74
EGKSSGSGSE SKST                                                            14

SEQ ID NO: 75          moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 75
GSAGSAAGSG EF                                                              12

SEQ ID NO: 76          moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 76
AEAAAKEAAA KA                                                              12
```

-continued

```
SEQ ID NO: 77          moltype = AA  length = 18
FEATURE                Location/Qualifiers
REGION                 1..18
                       note = source = /note="Description of Artificial Sequence:
                        Synthetic peptide"
source                 1..18
                       mol_type = protein
                       organism = synthetic construct
SEQUENCE: 77
KESGSVSSEQ LAQFRSLD                                                   18

SEQ ID NO: 78          moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 78
GENLYFQSGG                                                            10

SEQ ID NO: 79          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 79
SACYCELS                                                              8

SEQ ID NO: 80          moltype = AA  length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 80
RSIAT                                                                 5

SEQ ID NO: 81          moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 81
RPACKIPNDL KQKVMNH                                                    17

SEQ ID NO: 82          moltype = AA  length = 36
FEATURE                Location/Qualifiers
REGION                 1..36
                       note = source = /note="Description of Artificial Sequence:
                        Synthetic polypeptide"
source                 1..36
                       mol_type = protein
                       organism = synthetic construct
SEQUENCE: 82
GGSAGGSGSG SSGGSSGASG TGTAGGTGSG SGTGSG                               36

SEQ ID NO: 83          moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 83
AAANSSIDLI SVPVDSR                                                    17

SEQ ID NO: 84          moltype = AA  length = 36
FEATURE                Location/Qualifiers
```

```
REGION                  1..36
                        note = source = /note="Description of Artificial Sequence:
                         Synthetic polypeptide"
source                  1..36
                        mol_type = protein
                        organism = synthetic construct
SEQUENCE: 84
GGSGGGSEGG GSEGGGSEGG GSEGGGSEGG GSGGGS                                    36

SEQ ID NO: 85           moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 85
EAAAK                                                                      5

SEQ ID NO: 86           moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 86
PAPAP                                                                      5

SEQ ID NO: 87           moltype =   length =
SEQUENCE: 87
000

SEQ ID NO: 88           moltype =   length =
SEQUENCE: 88
000

SEQ ID NO: 89           moltype =   length =
SEQUENCE: 89
000

SEQ ID NO: 90           moltype =   length =
SEQUENCE: 90
000

SEQ ID NO: 91           moltype = AA  length = 15
FEATURE                 Location/Qualifiers
SITE                    1..15
                        note = /note="This sequence may encompass 0-15 residues"
REGION                  1..15
                        note = source = /note="Description of Artificial Sequence:
                         Synthetic peptide"
source                  1..15
                        mol_type = protein
                        organism = synthetic construct
SEQUENCE: 91
RRRRRRRRRR RRRRR                                                          15

SEQ ID NO: 92           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 92
DSSSEEKFLR RIGRFG                                                         16

SEQ ID NO: 93           moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
```

```
SEQUENCE: 93
EEEEEEEPRG DT                                                               12

SEQ ID NO: 94          moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 94
APWHLSSQYS RT                                                               12

SEQ ID NO: 95          moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 95
STLPIPHEFS RE                                                               12

SEQ ID NO: 96          moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 96
VTKHLNQISQ SY                                                               12

SEQ ID NO: 97          moltype = AA  length = 15
FEATURE                Location/Qualifiers
SITE                   1..15
                       note = /note="This sequence may encompass 1-15 residues"
REGION                 1..15
                       note = source = /note="Description of Artificial Sequence:
                        Synthetic peptide"
source                 1..15
                       mol_type = protein
                       organism = synthetic construct
SEQUENCE: 97
EEEEEEEEEE EEEEE                                                            15

SEQ ID NO: 98          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 98
RSGSGGS                                                                     7

SEQ ID NO: 99          moltype = AA  length = 15
FEATURE                Location/Qualifiers
SITE                   1..15
                       note = /note="This sequence may encompass 1-15 residues"
REGION                 1..15
                       note = source = /note="Description of Artificial Sequence:
                        Synthetic peptide"
source                 1..15
                       mol_type = protein
                       organism = synthetic construct
SEQUENCE: 99
DDDDDDDDDD DDDDD                                                            15

SEQ ID NO: 100         moltype = AA  length = 16
FEATURE                Location/Qualifiers
REGION                 1..16
                       note = source = /note="Description of Artificial Sequence:
                        Synthetic peptide"
source                 1..16
```

-continued

```
                        mol_type = protein
                        organism = synthetic construct
SEQUENCE: 100
LVIMSLGLGL GLGLRK                                                    16

SEQ ID NO: 101          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 101
VIMSLGLGLG LGLRK                                                     15

SEQ ID NO: 102          moltype = AA  length = 14
FEATURE                 Location/Qualifiers
REGION                  1..14
                        note = source = /note="Description of Artificial Sequence:
                         Synthetic peptide"
source                  1..14
                        mol_type = protein
                        organism = synthetic construct
SEQUENCE: 102
IMSLGLGLGL GLRK                                                      14

SEQ ID NO: 103          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 103
MSLGLGLGLG LRK                                                       13

SEQ ID NO: 104          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 104
SLGLGLGLGL RK                                                        12

SEQ ID NO: 105          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 105
LGLGLGLGLR K                                                         11

SEQ ID NO: 106          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 106
GLGLGLGLRK                                                           10

SEQ ID NO: 107          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
```

-continued

```
SEQUENCE: 107
LGLGLGLRK                                                                   9

SEQ ID NO: 108        moltype = AA   length = 8
FEATURE               Location/Qualifiers
REGION                1..8
                      note = source = /note="Description of Artificial Sequence:
                       Synthetic peptide"
source                1..8
                      mol_type = protein
                      organism = synthetic construct
SEQUENCE: 108
GLGLGLRK                                                                    8

SEQ ID NO: 109        moltype = AA   length = 7
FEATURE               Location/Qualifiers
REGION                1..7
                      note = source = /note="Description of Artificial Sequence:
                       Synthetic peptide"
source                1..7
                      mol_type = protein
                      organism = synthetic construct
SEQUENCE: 109
LGLGLRK                                                                     7

SEQ ID NO: 110        moltype = AA   length = 6
FEATURE               Location/Qualifiers
REGION                1..6
                      note = source = /note="Description of Artificial Sequence:
                       Synthetic peptide"
source                1..6
                      mol_type = protein
                      organism = synthetic construct
SEQUENCE: 110
GLGLRK                                                                      6

SEQ ID NO: 111        moltype = AA   length = 5
FEATURE               Location/Qualifiers
REGION                1..5
                      note = source = /note="Description of Artificial Sequence:
                       Synthetic peptide"
source                1..5
                      mol_type = protein
                      organism = synthetic construct
SEQUENCE: 111
LGLRK                                                                       5

SEQ ID NO: 112        moltype = AA   length = 4
FEATURE               Location/Qualifiers
REGION                1..4
                      note = source = /note="Description of Artificial Sequence:
                       Synthetic peptide"
source                1..4
                      mol_type = protein
                      organism = synthetic construct
SEQUENCE: 112
GLRK                                                                        4

SEQ ID NO: 113        moltype =    length =
SEQUENCE: 113
000

SEQ ID NO: 114        moltype =    length =
SEQUENCE: 114
000

SEQ ID NO: 115        moltype = AA   length = 15
FEATURE               Location/Qualifiers
SITE                  1..15
                      note = /note="This sequence may encompass 1-15 residues"
REGION                1..15
                      note = source = /note="Description of Artificial Sequence:
                       Synthetic peptide"
source                1..15
                      mol_type = protein
                      organism = synthetic construct
SEQUENCE: 115
KKKKKKKKKK KKKKK                                                           15
```

```
SEQ ID NO: 116          moltype = AA  length = 875
FEATURE                 Location/Qualifiers
source                  1..875
                        mol_type = protein
                        organism = Homo sapiens
SEQUENCE: 116
MESTLTLATE QPVKKNTLKK YKIACIVLLA LLVIMSLGLG LGLGLRKLEK QGSCRKKCFD   60
ASFRGLENCR CDVACKDRGD CCWDFEDTCV ESTRIWMCNK FRCGETRLEA SLCSCSDDCL  120
QRKDCCADYK SVCQGETSWL EENCDTAQQS QCPEGFDLPP VILFSMDGFR AEYLYTWDTL  180
MPNINKLKTC GIHSKYMRAM YPTKTFPNHY TIVTGLYPES HGIIDNNMYD VNLNKNFSLS  240
SKEQNNPAWW HGQPMWLTAM YQGLKAATYF WPGSEVAING SFPSIYMPYN GSVPFEERIS  300
TLLKWLDLPK AERPRFYTMY FEEPDSSGHA GGPVSARVIK ALQVVDHAFG MLMEGLKQRN  360
LHNCVNIILL ADHGMDQTYC NKMEYMTDYF PRINFFYMYE GPAPRIRAHN IPHDFFSFNS  420
EEIVRNLSCR KPDQHFKPYL TPDLPKRLHY AKNVRIDKVH LFVDQQWLAV RSKSNTNCGG  480
GNHGYNNEFR SMEAIFLAHG PSFKEKTEVE PFENIEVYNL MCDLLRIQPA PNNGTHGSLN  540
HLLKVPFYEP SHAEEVSKFS VCGFANPLPT ESLDCFCPHL QNSTQLEQVN QMLNLTQEEI  600
TATVKVNLPF GRPRVLQKNV DHCLLYHREY VSGFGKAMRM PMWSSYTVPQ LGDTSPLPPT  660
VPDCLRADVR VPPSESQKCS FYLADKNITH GFLYPPASNR TSDSQYDALI TSNLVPMYEE  720
FRKMWDYFHS VLLIKHATER NGVNVVSGPI FDYNYDGHFD APDEITKHLA NTDVPIPTHY  780
FVVLTSCKNK SHTPENCPGW LDVLPFIIPH RPTNVESCPE GKPEALWVEE RFTAHIARVR  840
DVELLTGLDF YQDKVQPVSE ILQLKTYLPT FETTI                            875

SEQ ID NO: 117          moltype = AA  length = 1057
FEATURE                 Location/Qualifiers
REGION                  1..1057
                        note = source = /note="Description of Artificial Sequence:
                         Synthetic polypeptide"
source                  1..1057
                        mol_type = protein
                        organism = synthetic construct
SEQUENCE: 117
PSCAKEVKSC KGRCFERTFG NCRCDAACVE LGNCCLDYQE TCIEPEHIWT CNKFRCGEKR   60
LTRSLCACSD DCKDKGDCCI NYSSVCQGEK SWVEEPCESI NEPQCPAGFE TPPTLLFSLD  120
GFRAEYLHTW GGLLPVISKL KKCGTYTKNM RPVYPTKTFP NHYSIVTGLY PESHGIIDNK  180
MYDPKMNASF SLKSKEKFNP EWYKGEPIWV TAKYQGLKSG TFFWPGSDVE INGIFPDIYK  240
MYNGSVPFEE RILAVLQWLQ LPKDERPHFY TLYLEEPDSS GHSYGPVSSE VIKALQRVDN  300
MVGMLMDGLK ELNLHRCLNL ILVSDHGMEQ GSCKKYIYLN KYLGDVKNIK VIYGPAARLR  360
PSDVPDKYYS FNYEGIARNL SCREPNQHFK PYLKHFLPKR LHFAKSDRIE PLTFYLDPQW  420
QLALNPSERK YCGSGFHGSD NIFSNMQALF VGYGPGFKHG IEVDTFENIE VYNLMCDLLN  480
LTPAPNNGTH GSLNHLLKNP VYTPKHPKEV HPLIQCPFTR NPRDNLGCSC NPSILPIEDF  540
QTQFNLTVAE EKNIKHETLP YGRPRVLQKE NTICLLSQHQ FMSGYSQDIL MPLWTSYTVD  600
RNDSFSTEDF SNCLYQDFRI PLSPVHKCSF YKNNTKVSYG FLSPPQLNKN SSGIYSEALL  660
TTNIVPMYQS FQVIWRYFHD TLLRKYAEER NGVNVVSGPV FDFDYDGRCD SLENLRQKRR  720
VIRNQEILIP THFFIVLTSC KDTSQTPLHC ENLDTLAFIL PHRTDNSESC VHGKHDSSWV  780
EELLMLHRAR ITDVEHITGL SFYQQRKEPV SDILKLKTHL PTFSQEDLIN DKTHTCPPCP  840
APELLGGPSV FLFPPKPKDT LMISRTPEVT CVVVDVSHED PEVKFNWYVD GVEVHNAKTK  900
PREEQYNSTY RVVSVLTVLH QDWLNGKEYK CKVSNKALPA PIEKTISKAK GQPREPQVYT  960
LPPSREEMTK NQVSLTCLVK GFYPSDIAVE WESNGQPENN YKTTPPVLDS DGSFFLYSKL 1020
TVDKSRWQQG NVFSCSVMHE ALHNHYTQKS LSLSPGK                         1057

SEQ ID NO: 118          moltype = AA  length = 1057
FEATURE                 Location/Qualifiers
REGION                  1..1057
                        note = source = /note="Description of Artificial Sequence:
                         Synthetic polypeptide"
source                  1..1057
                        mol_type = protein
                        organism = synthetic construct
SEQUENCE: 118
PSCAKEVKSC KGRCFERTFG NCRCDAACVE LGNCCLDYQE TCIEPEHIWT CNKFRCGEKR   60
LTRSLCACSD DCKDKGDCCI NYSSVCQGEK SWVEEPCESI NEPQCPAGFE TPPTLLFSLD  120
GFRAEYLHTW GGLLPVISKL KKCGTYTKNM RPVYPTKTFP NHYSIVTGLY PESHGIIDNK  180
MYDPKMNASF SLKSKEKFNP EWYKGEPIWV TAKYQGLKSG TFFWPGSDVE INGIFPDIYK  240
MYNGSVPFEE RILAVLQWLQ LPKDERPHFY TLYLEEPDSS GHSYGPVSSE VIKALQRVDG  300
MVGMLMDGLK ELNLHRCLNL ILISDHGMEQ GSCKKYIYLN KYLGDVKNIK VIYGPAARLR  360
PSDVPDKYYS FNYEGIARNL SCREPNQHFK PYLKHFLPKR LHFAKSDRIE PLTFYLDPQW  420
QLALNPSERK YCGSGFHGSD NVFSNMQALF VGYGPGFKHG IEADTFENIE VYNLMCDLLN  480
LTPAPNNGTH GSLNHLLKNP VYTPKHPKEV HPLVQCPFTR NPRDNLGCSC NPSILPIEDF  540
QTQFNLTVAE EKIIKHETLP YGRPRVLQKK NTICLLSQHQ FMSGYSQDIL MPLWTSYTVD  600
RNDSFSTEDF SNCLYQDFRI SLSPVHKCSF YKNNTKVSYG FLSPPQLNKN SSGIYSEALL  660
TTNIVPMYQS FQVIWRYFHD TLLRKYAEER NGVNVVSGPV FDFDYDGRYD SLEILRQKRR  720
VIRNQEILIP THFFIVLTSC KDASQTPLHC ENLDTLAFIL PHRTDNSESC VHGKHESSWV  780
EELLMLHRAR ITDVEHITGL SFYQQRKEPV SDILKLKTHL PTFSQEDLIN DKTHTCPPCP  840
APELLGGPSV FLFPPKPKDT LMISRTPEVT CVVVDVSHED PEVKFNWYVD GVEVHNAKTK  900
PREEQYNSTY RVVSVLTVLH QDWLNGKEYK CKVSNKALPA PIEKTISKAK GQPREPQVYT  960
LPPSREEMTK NQVSLTCLVK GFYPSDIAVE WESNGQPENN YKTTPPVLDS DGSFFLYSKL 1020
TVDKSRWQQG NVFSCSVMHE ALHNHYTQKS LSLSPGK                         1057

SEQ ID NO: 119          moltype = AA  length = 1059
```

```
FEATURE                  Location/Qualifiers
REGION                   1..1059
                         note = source = /note="Description of Artificial Sequence:
                         Synthetic polypeptide"
source                   1..1059
                         mol_type = protein
                         organism = synthetic construct
SEQUENCE: 119
PSCAKEVKSC KGRCFERTFG NCRCDAACVE LGNCCLDYQE TCIEPEHIWT CNKFRCGEKR   60
LTRSLCACSD DCKDKGDCCI NYSSVCQGEK SWVEEPCESI NEPQCPAGFE TPPTLLFSLD  120
GFRAEYLHTW GGLLPVISKL KKCGTYTKNM RPVYPTKTFP NHYSIVTGLY PESHGIIDNK  180
MYDPKMNASF SLKSKEKFNP EWYKGEPIWV TAKYQGLKSG TFFWPGSDVE INGIFPDIYK  240
MYNGSVPFEE RILAVLQWLQ LPKDERPHFY TLYLEEPDSS GHSYGPVSSE VIKALQRVDG  300
MVGMLMDGLK ELNLHRCLNL ILISDHGMEQ GSCKKYIYLN KYLGDVKNIK VIYGPAARLR  360
PSDVPDKYYS FNYEGIARNL SCREPNQHFK PYLKHFLPKR LHFAKSDRIE PLTFYLDPQW  420
QLALNPSERK YCGSGFHGSD NVFSNMQALF VGYGPGFKHG IEADTFENIE VYNLMCDLLN  480
LTPAPNNGTH GSLNHLLKNP VYTPKHPKEV HPLVQCPFTR NPRDNLGCSC NPSILPIEDF  540
QTQFNLTVAE EKIIKHETLP YGRPRVLQKE NTICLLSQHQ FMSGYSQDIL MPLWTSYTVD  600
RNDSFSTEDF SNCLYQDFRI PLSPVHKCSF YKNNTKVSYG FLSPPQLNKN SSGIYSEALL  660
TTNIVPMYQS FQVIWRYFHD TLLRKYAEER NGVNVVSGPV FDFDYDGRCD SLENLRQKRR  720
VIRNQEILIP THFFIVLTSC KDTSQTPLHC ENLDTLAFIL PHRTDNSESC VHGKHDSSWV  780
EELLMLHRAR ITDVEHITGL SFYQQRKEPV SDILKLKTHL PTFSQEDGGG GSDKTHTCPP  840
CPAPELLGGP SVFLFPPKPK DTLMISRTPE VTCVVVDVSH EDPEVKFNWY VDGVEVHNAK  900
TKPREEQYNS TYRVVSVLTV LHQDWLNGKE YKCKVSNKAL PAPIEKTISK AKGQPREPQV  960
YTLPPSREEM TKNQVSLTCL VKGFYPSDIA VEWESNGQPE NNYKTTPPVL DSDGSFFLYS 1020
KLTVDKSRWQ QGNVFSCSVM HEALHNHYTQ KSLSLSPGK                        1059

SEQ ID NO: 120           moltype = AA  length = 1059
FEATURE                  Location/Qualifiers
REGION                   1..1059
                         note = source = /note="Description of Artificial Sequence:
                         Synthetic polypeptide"
source                   1..1059
                         mol_type = protein
                         organism = synthetic construct
SEQUENCE: 120
PSCAKEVKSC KGRCFERTFG NCRCDAACVE LGNCCLDYQE TCIEPEHIWT CNKFRCGEKR   60
LTRSLCACSD DCKDKGDCCI NYSSVCQGEK SWVEEPCESI NEPQCPAGFE TPPTLLFSLD  120
GFRAEYLHTW GGLLPVISKL KKCGTYTKNM RPVYPTKTFP NHYSIVTGLY PESHGIIDNK  180
MYDPKMNASF SLKSKEKFNP EWYKGEPIWV TAKYQGLKSG TFFWPGSDVE INGTFPDIYK  240
MYNGSVPFEE RILAVLQWLQ LPKDERPHFY TLYLEEPDSS GHSYGPVSSE VIKALQRVDG  300
MVGMLMDGLK ELNLHRCLNL ILISDHGMEQ GSCKKYIYLN KYLGDVKNIK VIYGPAARLR  360
PSDVPDKYYS FNYEGIARNL SCREPNQHFK PYLKHFLPKR LHFAKSDRIE PLTFYLDPQW  420
QLALNPSERK YCGSGFHGSD NVFSNMQALF VGYGPGFKHG IEADTFENIE VYNLMCDLLN  480
LTPAPNNGTH GSLNHLLKNP VYTPKHPKEV HPLVQCPFTR NPRDNLGCSC NPSILPIEDF  540
QTQFNLTVAE EKIIKHETLP YGRPRVLQKE NTICLLSQHQ FMSGYSQDIL MPLWTSYTVD  600
RNDSFSTEDF SNCLYQDFRI PLSPVHKCSF YKNNTKVSYG FLSPPQLNKN SSGIYSEALL  660
TTNIVPMYQS FQVIWRYFHD TLLRKYAEER NGVNVVSGPV FDFDYDGRCD SLENLRQKRR  720
VIRNQEILIP THFFIVLTSC KDTSQTPLHC ENLDTLAFIL PHRTDNSESC VHGKHDSSWV  780
EELLMLHRAR ITDVEHITGL SFYQQRKEPV SDILKLKTHL PTFSQEDGGG GSDKTHTCPP  840
CPAPELLGGP SVFLFPPKPK DTLYITREPE VTCVVVDVSH EDPEVKFNWY VDGVEVHNAK  900
TKPREEQYNS TYRVVSVLTV LHQDWLNGKE YKCKVSNKAL PAPIEKTISK AKGQPREPQV  960
YTLPPSREEM TKNQVSLTCL VKGFYPSDIA VEWESNGQPE NNYKTTPPVL DSDGSFFLYS 1020
KLTVDKSRWQ QGNVFSCSVM HEALHNHYTQ KSLSLSPGK                        1059

SEQ ID NO: 121           moltype = AA  length = 968
FEATURE                  Location/Qualifiers
REGION                   1..968
                         note = source = /note="Description of Artificial Sequence:
                         Synthetic polypeptide"
source                   1..968
                         mol_type = protein
                         organism = synthetic construct
SEQUENCE: 121
WVEEPCESIN EPQCPAGFET PPTLLFSLDG FRAEYLHTWG GLLPVISKLK KCGTYTKNMR   60
PVYPTKTFPN HYSIVTGLYP ESHGIIDNKM YDPKMNASFS LKSKEKFNPE WYKGEPIWVT  120
AKYQGLKSGT FFWPGSDVEI NGTFPDIYKM YNGSVPFEER ILAVLQWLQL PKDERPHFYT  180
LYLEEPDSSG HSYGPVSSEV IKALQRVDGM VGMLMDGLKL NLHRCLNLI LISDHGMEQG  240
SCKKYIYLNK YLGDVKNIKV IYGPAARLRP SDVPDKYYSF NYEGIARNLS CREPNQHFKP  300
YLKHFLPKRL HFAKSDRIEP LTFYLDPQWQ LALNPSERKY CGSGFHGSDN VFSNMQALFV  360
GYGPGFKHGI EADTFENIEV YNLMCDLLNL TPAPNNGTHG SLNHLLKNPV YTPKHPKEVH  420
PLVQCPFTRN PRDNLGCSCN PSILPIEDFQ TQFNLTVAEE KIIKHETLPY GRPRVLQKEN  480
TICLLSQHQF MSGYSQDILM PLWTSYTVDR NDSFSTEDFS NCLYQDFRIP LSPVHKCSFY  540
KNNTKVSYGF LSPPQLNKNS SGIYSEALLT NIVPMYQSF QVIWRYFHDT LLRKYAEERN  600
GVNVVSGPVF DFDYDGRCDS LENLRQKRRV IRNQEILIPT HFFIVLTSCK DTSQTPLHCE  660
NLDTLAFILP HRTDNSESCV HGKHDSSWVE ELLMLHRARI TDVEHITGLS FYQQRKEPVS  720
DILKLKTHLP TFSQEDGGGG SDKTHTCPPC PAPELLGGPS VFLFPPKPKD TLYITREPEV  780
TCVVVDVSHE DPEVKFNWYV DGVEVHNAKT KPREEQYNST YRVVSVLTVL HQDWLNGKEY  840
KCKVSNKALP APIEKTISKA KGQPREPQVY TLPPSREEMT KNQVSLTCLV KGFYPSDIAV  900
```

```
EWESNGQPEN NYKTTPPVLD SDGSFFLYSK LTVDKSRWQQ GNVFSCSVMH EALHNHYTQK    960
SLSLSPGK                                                              968

SEQ ID NO: 122          moltype = AA  length = 966
FEATURE                 Location/Qualifiers
REGION                  1..966
                        note = source = /note="Description of Artificial Sequence:
                        Synthetic polypeptide"
source                  1..966
                        mol_type = protein
                        organism = synthetic construct
SEQUENCE: 122
WVEEPCESIN EPQCPAGFET PPTLLFSLDG FRAEYLHTWG GLLPVISKLK KCGTYTKNMR     60
PVYPTKTFPN HYSIVTGLYP ESHGIIDNKM YDPKMNASFS LKSKEKFNPE WYKGEPIWVT    120
AKYQGLKSGT FFWPGSDVEI NGIFPDIYKM YNGSVPFEER ILAVLQWLQL PKDERPHFYT    180
LYLEEPDSSG HSYGPVSSEV IKALQRVDGM VGMLMDGLKE LNLHRCLNLI LISDHGMEQG    240
SCKKYIYLNK YLGDVKNIKV IYGPAARLRP SDVPDKYYSF NYEGIARNLS CREPNQHFKP    300
YLKHFLPKRL HFAKSDRIEP LTFYLDPQWQ LALNPSERKY CGSGFHGSDN VFSNMQALFV    360
GYGPGFKHGI EADTFENIEV YNLMCDLLNL TPAPNNGTHG SLNHLLKNPV YTPKHPKEVH    420
PLVQCPFTRN PRDNLGCSCN PSILPIEDFQ TQFNLTVAEE KIIKHETLPY GRPRVLQKEN    480
TICLLSQHQF MSGYSQDILM PLWTSYTVDR NDSFSTEDFS NCLYQDFRIP LSPVHKCSFY    540
KNNTKVSYGF LSPPQLNKNS SGIYSEALLT TNIVPMYQSF QVIWRYFHDT LLRKYAEERN    600
GVNVVSGPVF DFDYDGRCDS LENLRQKRRV IRNQEILIPT HFFIVLTSCK DTSQTPLHCE    660
NLDTLAFILP HRTDNSESCV HGKHDSSWVE ELLMLHRARI TDVEHITGLS FYQQRKEPVS    720
DILKLKTHLP TFSQEDLIND KTHTCPPCPA PELLGGPSVF LFPPKPKDTL MISRTPEVTC    780
VVVDVSHEDP EVKFNWYVDG VEVHNAKTKP REEQYNSTYR VVSVLTVLHQ DWLNGKEYKC    840
KVSNKALPAP IEKTISKAKG QPREPQVYTL PPSREEMTKN QVSLTCLVKG FYPSDIAVEW    900
ESNGQPENNY KTTPPVLDSD GSFFLYSKLT VDKSRWQQGN VFSCSVMHEA LHNHYTQKSL    960
SLSPGK                                                               966

SEQ ID NO: 123          moltype = AA  length = 1076
FEATURE                 Location/Qualifiers
REGION                  1..1076
                        note = source = /note="Description of Artificial Sequence:
                        Synthetic polypeptide"
source                  1..1076
                        mol_type = protein
                        organism = synthetic construct
SEQUENCE: 123
MTRLTVLALL AGLLASSRAP SCAKEVKSCK GRCFERTFGN CRCDAACVEL GNCCLDYQET     60
CIEPEHIWTC NKFRCGEKRL TRSLCACSDD CKDKGDCCIN YSSVCQGEKS WVEEPCESIN    120
EPQCPAGFET PPTLLFSLDG FRAEYLHTWG GLLPVISKLK KCGTYTKNMR PVYPTKTFPN    180
HYSIVTGLYP ESHGIIDNKM YDPKMNASFS LKSKEKFNPE WYKGEPIWVT AKYQGLKSGT    240
FFWPGSDVEI NGIFPDIYKM YNGSVPFEER ILAVLQWLQL PKDERPHFYT LYLEEPDSSG    300
HSYGPVSSEV IKALQRVDNM VGMLMDGLKE LNLHRCLNLI LVSDHGMEQG SCKKYIYLNK    360
YLGDVKNIKV IYGPAARLRP SDVPDKYYSF NYEGIARNLS CREPNQHFKP YLKHFLPKRL    420
HFAKSDRIEP LTFYLDPQWQ LALNPSERKY CGSGFHGSDN IFSNMQALFV GYGPGFKHGI    480
EVDTFENIEV YNLMCDLLNL TPAPNNGTHG SLNHLLKNPV YTPKHPKEVH PLIQCPFTRN    540
PRDNLGCSCN PSILPIEDFQ TQFNLTVAEE KNIKHETLPY GRPRVLQKEN TICLLSQHQF    600
MSGYSQDILM PLWTSYTVDR NDSFSTEDFS NCLYQDFRIP LSPVHKCSFY KNNTKVSYGF    660
LSPPQLNKNS SGIYSEALLT TNIVPMYQSF QVIWRYFHDT LLRKYAEERN GVNVVSGPVF    720
DFDYDGRCDS LENLRQKRRV IRNQEILIPT HFFIVLTSCK DTSQTPLHCE NLDTLAFILP    780
HRTDNSESCV HGKHDSSWVE ELLMLHRARI TDVEHITGLS FYQQRKEPVS DILKLKTHLP    840
TFSQEDLIND KTHTCPPCPA PELLGGPSVF LFPPKPKDTL MISRTPEVTC VVVDVSHEDP    900
EVKFNWYVDG VEVHNAKTKP REEQYNSTYR VVSVLTVLHQ DWLNGKEYKC KVSNKALPAP    960
IEKTISKAKG QPREPQVYTL PPSREEMTKN QVSLTCLVKG FYPSDIAVEW ESNGQPENNY   1020
KTTPPVLDSD GSFFLYSKLT VDKSRWQQGN VFSCSVMHEA LHNHYTQKSL SLSPGK       1076

SEQ ID NO: 124          moltype = AA  length = 1076
FEATURE                 Location/Qualifiers
REGION                  1..1076
                        note = source = /note="Description of Artificial Sequence:
                        Synthetic polypeptide"
source                  1..1076
                        mol_type = protein
                        organism = synthetic construct
SEQUENCE: 124
MTRLTVLALL AGLLASSRAP SCAKEVKSCK GRCFERTFGN CRCDAACVEL GNCCLDYQET     60
CIEPEHIWTC NKFRCGEKRL TRSLCACSDD CKDKGDCCIN YSSVCQGEKS WVEEPCESIN    120
EPQCPAGFET PPTLLFSLDG FRAEYLHTWG GLLPVISKLK KCGTYTKNMR PVYPTKTFPN    180
HYSIVTGLYP ESHGIIDNKM YDPKMNASFS LKSKEKFNPE WYKGEPIWVT AKYQGLKSGT    240
FFWPGSDVEI NGIFPDIYKM YNGSVPFEER ILAVLQWLQL PKDERPHFYT LYLEEPDSSG    300
HSYGPVSSEV IKALQRVDGM VGMLMDGLKE LNLHRCLNLI LISDHGMEQG SCKKYIYLNK    360
YLGDVKNIKV IYGPAARLRP SDVPDKYYSF NYEGIARNLS CREPNQHFKP YLKHFLPKRL    420
HFAKSDRIEP LTFYLDPQWQ LALNPSERKY CGSGFHGSDN VFSNMQALFV GYGPGFKHGI    480
EADTFENIEV YNLMCDLLNL TPAPNNGTHG SLNHLLKNPV YTPKHPKEVH PLVQCPFTRN    540
PRDNLGCSCN PSILPIEDFQ TQFNLTVAEE KIIKHETLPY GRPRVLQKKN TICLLSQHQF    600
MSGYSQDILM PLWTSYTVDR NDSFSTEDFS NCLYQDFRIS LSPVHKCSFY KNNTKVSYGF    660
LSPPQLNKNS SGIYSEALLT TNIVPMYQSF QVIWRYFHDT LLRKYAEERN GVNVVSGPVF    720
```

```
DFDYDGRYDS LEILRQKRRV IRNQEILIPT HFFIVLTSCK DASQTPLHCE NLDTLAFILP  780
HRTDNSESCV HGKHESSWVE ELLMLHRARI TDVEHITGLS FYQQRKEPVS DILKLKTHLP  840
TFSQEDLIND KTHTCPPCPA PELLGGPSVF LFPPKPKDTL MISRTPEVTC VVVDVSHEDP  900
EVKFNWYVDG VEVHNAKTKP REEQYNSTYR VVSVLTVLHQ DWLNGKEYKC KVSNKALPAP  960
IEKTISKAKG QPREPQVYTL PPSREEMTKN QVSLTCLVKG FYPSDIAVEW ESNGQPENNY  1020
KTTPPVLDSD GSFFLYSKLT VDKSRWQQGN VFSCSVMHEA LHNHYTQKSL SLSPGK      1076
```

```
SEQ ID NO: 125              moltype = AA  length = 1078
FEATURE                     Location/Qualifiers
REGION                      1..1078
                            note = source = /note="Description of Artificial Sequence:
                             Synthetic polypeptide"
source                      1..1078
                            mol_type = protein
                            organism = synthetic construct
SEQUENCE: 125
MTRLTVLALL AGLLASSRAP SCAKEVKSCK GRCFERTFGN CRCDAACVEL GNCCLDYQET  60
CIEPEHIWTC NKFRCGEKRL TRSLCACSDD CKDKGDCCIN YSSVCQGEKS WVEEPCESIN  120
EPQCPAGFET PPTLLFSLDG FRAEYLHTWG GLLPVISKLK KCGTYTKNMR PVYPTKTFPN  180
HYSIVTGLYP ESHGIIDNKM YDPKMNASFS LKSKEKFNPE WYKGEPIWVT AKYQGLKSGT  240
FFWPGSDVEI NGIFPDIYKM YNGSVPFEER ILAVLQWLQL PKDERPHFYT LYLEEPDSSG  300
HSYGPVSSEV IKALQRVDGM VGMLMDGLKE LNLHRCLNLI LISDHGMEQG SCKKYIYLNK  360
YLGDVKNIKV IYGPAARLRP SDVPDKYYSF NYEGIARNLS CREPNQHFKP YLKHFLPKRL  420
HFAKSDRIEP LTFYLDPQWQ LALNPSERKY CGSGFHGSDN VFSNMQALFV GYGPGFKHGI  480
EADTFENIEV YNLMCDLLNL TPAPNNGTHG SLNHLLKNPV YTPKHPKEVH PLVQCPFTRN  540
PRDNLGCSCN PSILPIEDFQ TQFNLTVAEE KIIKHETLPY GRPRVLQKEN TICLLSQHQF  600
MSGYSQDILM PLWTSYTVDR NDSFSTEDFS NCLYQDFRIP LSPVHKCSFY KNNTKVSYGF  660
LSPPQLNKNS SGIYSEALLT TNIVPMYQSF QVIWRYFHDT LLRKYAEERN GVNVVSGPVF  720
DFDYDGRCDS LENLRQKRRV IRNQEILIPT HFFIVLTSCK DTSQTPLHCE NLDTLAFILP  780
HRTDNSESCV HGKHDSSWVE ELLMLHRARI TDVEHITGLS FYQQRKEPVS DILKLKTHLP  840
TFSQEDGGGG SDKTHTCPPC PAPELLGGPS VFLFPPKPKD TLMISRTPEV TCVVVDVSHE  900
DPEVKFNWYV DGVEVHNAKT KPREEQYNST YRVVSVLTVL HQDWLNGKEY KCKVSNKALP  960
APIEKTISKA KGQPREPQVY TLPPSREEMT KNQVSLTCLV KGFYPSDIAV EWESNGQPEN  1020
NYKTTPPVLD SDGSFFLYSK LTVDKSRWQQ GNVFSCSVMH EALHNHYTQK SLSLSPGK   1078
```

```
SEQ ID NO: 126              moltype = AA  length = 1078
FEATURE                     Location/Qualifiers
REGION                      1..1078
                            note = source = /note="Description of Artificial Sequence:
                             Synthetic polypeptide"
source                      1..1078
                            mol_type = protein
                            organism = synthetic construct
SEQUENCE: 126
MTRLTVLALL AGLLASSRAP SCAKEVKSCK GRCFERTFGN CRCDAACVEL GNCCLDYQET  60
CIEPEHIWTC NKFRCGEKRL TRSLCACSDD CKDKGDCCIN YSSVCQGEKS WVEEPCESIN  120
EPQCPAGFET PPTLLFSLDG FRAEYLHTWG GLLPVISKLK KCGTYTKNMR PVYPTKTFPN  180
HYSIVTGLYP ESHGIIDNKM YDPKMNASFS LKSKEKFNPE WYKGEPIWVT AKYQGLKSGT  240
FFWPGSDVEI NGTFPDIYKM YNGSVPFEER ILAVLQWLQL PKDERPHFYT LYLEEPDSSG  300
HSYGPVSSEV IKALQRVDGM VGMLMDGLKE LNLHRCLNLI LISDHGMEQG SCKKYIYLNK  360
YLGDVKNIKV IYGPAARLRP SDVPDKYYSF NYEGIARNLS CREPNQHFKP YLKHFLPKRL  420
HFAKSDRIEP LTFYLDPQWQ LALNPSERKY CGSGFHGSDN VFSNMQALFV GYGPGFKHGI  480
EADTFENIEV YNLMCDLLNL TPAPNNGTHG SLNHLLKNPV YTPKHPKEVH PLVQCPFTRN  540
PRDNLGCSCN PSILPIEDFQ TQFNLTVAEE KIIKHETLPY GRPRVLQKEN TICLLSQHQF  600
MSGYSQDILM PLWTSYTVDR NDSFSTEDFS NCLYQDFRIP LSPVHKCSFY KNNTKVSYGF  660
LSPPQLNKNS SGIYSEALLT TNIVPMYQSF QVIWRYFHDT LLRKYAEERN GVNVVSGPVF  720
DFDYDGRCDS LENLRQKRRV IRNQEILIPT HFFIVLTSCK DTSQTPLHCE NLDTLAFILP  780
HRTDNSESCV HGKHDSSWVE ELLMLHRARI TDVEHITGLS FYQQRKEPVS DILKLKTHLP  840
TFSQEDGGGG SDKTHTCPPC PAPELLGGPS VFLFPPKPKD TLYITREPEV TCVVVDVSHE  900
DPEVKFNWYV DGVEVHNAKT KPREEQYNST YRVVSVLTVL HQDWLNGKEY KCKVSNKALP  960
APIEKTISKA KGQPREPQVY TLPPSREEMT KNQVSLTCLV KGFYPSDIAV EWESNGQPEN  1020
NYKTTPPVLD SDGSFFLYSK LTVDKSRWQQ GNVFSCSVMH EALHNHYTQK SLSLSPGK   1078
```

```
SEQ ID NO: 127              moltype = AA  length = 989
FEATURE                     Location/Qualifiers
REGION                      1..989
                            note = source = /note="Description of Artificial Sequence:
                             Synthetic polypeptide"
source                      1..989
                            mol_type = protein
                            organism = synthetic construct
SEQUENCE: 127
MTRLTVLALL AGLLASSRAK SWVEEPCESI NEPQCPAGFE TPPTLLFSLD GFRAEYLHTW  60
GGLLPVISKL KKCGTYTKNM RPVYPTKTFP NHYSIVTGLY PESHGIIDNK MYDPKMNASF  120
SLKSKEKFNP EWYKGEPIWV TAKYQGLKSG TFFWPGSDVE INGTFPDIYK MYNGSVPFEE  180
RILAVLQWLQ LPKDERPHFY TLYLEEPDSS GHSYGPVSSE VIKALQRVDG MVGMLMDGLK  240
ELNLHRCLNL ILISDHGMEQ GSCKKYIYLN KYLGDVKNIK VIYGPAARLR PSDVPDKYYS  300
FNYEGIARNL SCREPNQHFK PYLKHFLPKR LHFAKSDRIE PLTFYLDPQW QLALNPSERK  360
YCGSGFHGSD NVFSNMQALF VGYGPGFKHG IEADTFENIE VYNLMCDLLN LTPAPNNGTH  420
```

```
GSLNHLLKNP VYTPKHPKEV HPLVQCPFTR NPRDNLGCSC NPSILPIEDF QTQFNLTVAE   480
EKIIKHETLP YGRPRVLQKE NTICLLSQHQ FMSGYSQDIL MPLWTSYTVD RNDSFSTEDF   540
SNCLYQDFRI PLSPVHKCSF YKNNTKVSYG FLSPPQLNKN SSGIYSEALL TTNIVPMYQS   600
FQVIWRYFHD TLLRKYAEER NGVNVVSGPV FDFDYDGRCD SLENLRQKRR VIRNQEILIP   660
THFFIVLTSC KDTSQTPLHC ENLDTLAFIL PHRTDNSESC VHGKHDSSWV EELLMLHRAR   720
ITDVEHITGL SFYQQRKEPV SDILKLKTHL PTFSQEDGGG GSDKTHTCPP CPAPELLGGP   780
SVFLFPPKPK DTLYITREPE VTCVVVDVSH EDPEVKFNWY VDGVEVHNAK TKPREEQYNS   840
TYRVVSVLTV LHQDWLNGKE YKCKVSNKAL PAPIEKTISK AKGQPREPQV YTLPPSREEM   900
TKNQVSLTCL VKGFYPSDIA VEWESNGQPE NNYKTTPPVL DSDGSFFLYS KLTVDKSRWQ   960
QGNVFSCSVM HEALHNHYTQ KSLSLSPGK                                     989

SEQ ID NO: 128          moltype = AA  length = 987
FEATURE                 Location/Qualifiers
REGION                  1..987
                        note = source = /note="Description of Artificial Sequence:
                         Synthetic polypeptide"
source                  1..987
                        mol_type = protein
                        organism = synthetic construct SEQUENCE: 128
MTRLTVLALL AGLLASSRAK SWVEEPCESI NEPQCPAGFE TPPTLLFSLD GFRAEYLHTW   60
GGLLPVISKL KKCGTYTKNM RPVYPTKTFP NHYSIVTGLY PESHGIIDNK MYDPKMNASF   120
SLKSKEKFNP EWYKGEPIWV TAKYQGLKSG TFFWPGSDVE INGIFPDIYK MYNGSVPFEE   180
RILAVLQWLQ LPKDERPHFY TLYLEEPDSS GHSYGPVSSE VIKALQRVDG MVGMLMDGLK   240
ELNLHRCLNL ILISDHGMEQ GSCKKYIYLN KYLGDVKNIK VIYGPAARLR PSDVPDKYYS   300
FNYEGIARNL SCREPNQHFK PYLKHFLPKR LHFAKSDRIE PLTFYLDPQW QLALNPSERK   360
YCGSGFHGSD NVFSNMQALF VGYGPGFKHG IEADTFENIE VYNLMCDLLN LTPAPNNGTH   420
GSLNHLLKNP VYTPKHPKEV HPLVQCPFTR NPRDNLGCSC NPSILPIEDF QTQFNLTVAE   480
EKIIKHETLP YGRPRVLQKE NTICLLSQHQ FMSGYSQDIL MPLWTSYTVD RNDSFSTEDF   540
SNCLYQDFRI PLSPVHKCSF YKNNTKVSYG FLSPPQLNKN SSGIYSEALL TTNIVPMYQS   600
FQVIWRYFHD TLLRKYAEER NGVNVVSGPV FDFDYDGRCD SLENLRQKRR VIRNQEILIP   660
THFFIVLTSC KDTSQTPLHC ENLDTLAFIL PHRTDNSESC VHGKHDSSWV EELLMLHRAR   720
ITDVEHITGL SFYQQRKEPV SDILKLKTHL PTFSQEDLIN DKTHTCPPCP APELLGGPSV   780
FLFPPKPKDT LMISRTPEVT CVVVDVSHED PEVKFNWYVD GVEVHNAKTK PREEQYNSTY   840
RVVSVLTVLH QDWLNGKEYK CKVSNKALPA PIEKTISKAK GQPREPQVYT LPPSREEMTK   900
NQVSLTCLVK GFYPSDIAVE WESNGQPENN YKTTPPVLDS DGSFFLYSKL TVDKSRWQQG   960
NVFSCSVMHE ALHNHYTQKS LSLSPGK                                       987

SEQ ID NO: 129          moltype = AA  length = 19
FEATURE                 Location/Qualifiers
REGION                  1..19
                        note = source = /note="Description of Unknown: N-terminal
                         leader sequence"
source                  1..19
                        mol_type = protein
                        organism = unidentified SEQUENCE: 129
MTRLTVLALL AGLLASSRA                                                19

SEQ ID NO: 130          moltype = AA  length = 6
FEATURE                 Location/Qualifiers
REGION                  1..6
                        note = source = /note="Description of Artificial Sequence:
                         Synthetic 6xHis tag"
source                  1..6
                        mol_type = protein
                        organism = synthetic construct SEQUENCE: 130
HHHHHH                                                              6

SEQ ID NO: 131          moltype = DNA  length = 10
FEATURE                 Location/Qualifiers
misc_feature            1..10
                        note = source = /note="Description of Unknown: Kozak
                         sequence"
source                  1..10
                        mol_type = other DNA
                        organism = unidentified SEQUENCE: 131
gccaccatgg                                                          10

SEQ ID NO: 132          moltype = AA  length = 6
FEATURE                 Location/Qualifiers
source                  1..6
                        mol_type = protein
                        organism = Homo sapiens SEQUENCE: 132
WVEEPC                                                              6
```

```
SEQ ID NO: 133        moltype = AA   length = 5
FEATURE               Location/Qualifiers
REGION                1..5
                      note = source = /note="Description of Artificial Sequence:
                       Synthetic peptide"
source                1..5
                      mol_type = protein
                      organism = synthetic construct
SEQUENCE: 133
SRAKS                                                             5

SEQ ID NO: 134        moltype = AA   length = 10
FEATURE               Location/Qualifiers
VARIANT               1
                      note = Any amino acid
VARIANT               3
                      note = Any amino acid
VARIANT               5
                      note = Any amino acid
VARIANT               7
                      note = Any amino acid
VARIANT               9
                      note = Any amino acid
SITE                  1..10
                      note = /note="This sequence may encompass 1-5 'Xaa Pro'
                       repeating units"
REGION                1..10
                      note = source = /note="Description of Artificial Sequence:
                       Synthetic peptide"
REGION                1..10
                      note = source = /note="See specification as filed for
                       detailed description of substitutions and preferred
                       embodiments"
source                1..10
                      mol_type = protein
                      organism = synthetic construct
SEQUENCE: 134
XPXPXPXPXP                                                        10
```